US009212230B2

(12) United States Patent
Schuurman et al.

(10) Patent No.: US 9,212,230 B2
(45) Date of Patent: Dec. 15, 2015

(54) BISPECIFIC ANTIBODIES AND METHODS FOR PRODUCTION THEREOF

(75) Inventors: Janine Schuurman, Utrecht (NL); Tom Vink, Utrecht (NL); Jan Van De Winkel, Utrecht (NL); Aran Frank Labrijn, Utrecht (NL); Rob Aalberse, Duivendrecht (NL); Marijn Van Der Neut Kolfschote, Amsterdam (NL); Paul Parren, Utrecht (NL)

(73) Assignee: GENMAB A/S, Copenhagen (DK)

( * ) Notice: Subject to any disclaimer, the term of this patent is extended or adjusted under 35 U.S.C. 154(b) by 1427 days.

(21) Appl. No.: 12/593,759

(22) PCT Filed: Mar. 28, 2008

(86) PCT No.: PCT/DK2008/000124
§ 371 (c)(1),
(2), (4) Date: Jan. 6, 2010

(87) PCT Pub. No.: WO2008/119353
PCT Pub. Date: Oct. 9, 2008

(65) Prior Publication Data
US 2010/0105874 A1    Apr. 29, 2010

Related U.S. Application Data

(60) Provisional application No. 60/920,840, filed on Mar. 29, 2007.

(30) Foreign Application Priority Data

Mar. 29, 2007    (DK) .................................. 2007 00491

(51) Int. Cl.
*C07K 16/00* (2006.01)
*C07K 16/46* (2006.01)
*C07K 16/28* (2006.01)

(52) U.S. Cl.
CPC ............... *C07K 16/468* (2013.01); *C07K 16/00* (2013.01); *C07K 16/2863* (2013.01); *C07K 16/2887* (2013.01); *C07K 2317/24* (2013.01); *C07K 2317/31* (2013.01); *C07K 2317/526* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 5,292,668 A * | 3/1994 | Paulus | 436/547 |
| 5,807,706 A | 9/1998 | Carter et al. | |
| 6,737,056 B1 | 5/2004 | Presta | |
| 2004/0038894 A1* | 2/2004 | Daeron et al. | 514/12 |
| 2005/0208519 A1* | 9/2005 | Liew et al. | 435/6 |
| 2008/0051469 A1 | 2/2008 | Brahmbhatt et al. | |
| 2010/0015133 A1 | 1/2010 | Igawa et al. | |

FOREIGN PATENT DOCUMENTS

| | | |
|---|---|---|
| DE | 19859115 A1 | 3/2000 |
| EP | 1693386 A1 | 8/2006 |
| EP | 1870459 A1 | 12/2007 |
| WO | 96/27011 A1 | 9/1996 |
| WO | 98/04592 A1 | 2/1998 |
| WO | 98/50431 A2 | 11/1998 |
| WO | 02/100348 A2 | 12/2002 |
| WO | 04/035607 A2 | 4/2004 |
| WO | 2005/000899 A2 | 1/2005 |
| WO | 2005/062916 A2 | 7/2005 |
| WO | 2006/047340 A2 | 5/2006 |
| WO | 2006/106905 A1 | 10/2006 |
| WO | 2007/059782 A1 | 5/2007 |
| WO | 2007/103112 A2 | 9/2007 |
| WO | 2007/110205 A2 | 10/2007 |
| WO | 2007/147901 A1 | 12/2007 |
| WO | 2008/119353 A1 | 10/2008 |
| WO | 2008/145140 A2 | 12/2008 |
| WO | 2008/145142 A1 | 12/2008 |
| WO | 2009/089004 A1 | 7/2009 |
| WO | 2010/063785 A2 | 6/2010 |
| WO | 2010/129304 A2 | 11/2010 |
| WO | 2011/131746 A2 | 10/2011 |
| WO | 2011/133886 A2 | 10/2011 |
| WO | 2011/143545 A1 | 11/2011 |

(Continued)

OTHER PUBLICATIONS

Tao et al. (Journal of Experimental Medicine, 1993. vol. 178, pp. 661-667).*
Aalberse, Rob C. et al., "IgG4 breaking the rules," Immunology, vol. 105:9-19 (2002).
Aalberse, Rob C. et al., "Serologic Aspects of IgG4 Antibodies. I. Prolonged Immunization Results in an IgG4-Restricted Response," The Journal of Immunology, vol. 130(2):722-726 (1983).
Aalberse, Rob C. et al., "The Apparent Monovalency of Human IgG4 Is Due to Bispecificity," Int. Arch. Allergy Immunol., vol. 118:187-189 (1999).
Angal, S. et al., "A Single Amino Acid Substitution Abolishes the Heterogeneity of Chimeric Mouse/Human (IgG4) Antibody," Molecular Immunology, vol. 30(1):105-108 (1993).

(Continued)

*Primary Examiner* — Brad Duffy
(74) *Attorney, Agent, or Firm* — Nelson Mullins Riley & Scarborough LLP; Jane E. Remillard, Esq.; Christopher L. Frank

(57) ABSTRACT

The invention relates to an ex vivo method for the generation of a bispecific antibody, comprising the steps of: a) providing a first antibody having a first binding specificity, wherein said first antibody comprises an IgG4-like CH3 region, b) providing a second antibody having a second binding specificity which differs from said first binding specificity, wherein said second antibody comprises an IgG4-like CH3 region, c) incubating said first and second antibodies together under reducing conditions which allow the cysteines in the core hinge region to undergo disulfidebond isomerization, and d) obtaining a bispecific antibody. The invention furthermore relates to bispecific antibodies obtainable by the method of the invention.

29 Claims, 37 Drawing Sheets

(56) References Cited

FOREIGN PATENT DOCUMENTS

| WO | 2012/058768 A1 | 5/2012 |
|---|---|---|
| WO | 2012/116453 A1 | 9/2012 |

OTHER PUBLICATIONS

Bloom, James W. et al., "Interchain disulfide bond in the core hinge region of human IgG4," Protein Science, vol. 6:407-415 (1997).
Deng, Liang et al., "Detection and quantification of the human IgG4 half-molecule, HL, from unpurified cell-culture supernatants," Biotechnol. Appl. Biochem., vol. 40:261-269 (2004).
Labrijn, Aran F. et al., "Therapeutic IgG4 antibodies engage in Fab-arm exchange with endogenous human IgG4 in vivo," Nature Biotechnology, vol. 27:767-771 (2009).
Merchant, A. Margaret et al., "An efficient route to human bispecific IgG," Nature Biotechnology, vol. 16:677-681 (1998).
Schuurman, J. et al., "Normal human immunoglobulin G4 is bispecific: it has two different antigen-combining sites," Immunology, vol. 97:693-698 (1999).
Schuurman, Janine et al., "The inter-heavy chain disulfide bonds of IgG4 are in equilibrium with intra-chain disulfide bonds," Molecular Immunology, vol. 38:1-8 (2001).
van der Neut Kolfschoten, Marijn et al., "Anti-Inflammatory Activity of Human IgG4 Antibodies by Dynamic Fab Arm Exchange," Science, vol. 317:1554-1557 (2007).
Van Der Zee, Jaring S. et al., "Serologic Aspects of IgGr Antibodies. II. IgG4 Antibodies Form Small, Nonprecipitating Immune Complexes Due to Functional Monovalency," The Journal of Immunology, vol. 137(11):3566-3571 (1986).
Lewis, Kenneth B. et al., "Comparison of the ability of wild type and stabilized human IgG4 to undergo Fab arm exchange with endogenous IgG4 in vitro and in vivo," Molecular Immunology, vol. 46:3488-3494 (2009).
Stubenrauch, Kay et al., "Impact of Molecular Processing in the Hinge Region of Therapeutic IgG4 Antibodies on Disposition Profiles in Cynomolgus Monkeys," Drug Metabolism and Disposition, vol. 38(1):84-91 (2010).
U.S. Appl. No. 13/642,253, filed Oct. 24, 2012, Aran Frank Labrijn.
U.S. Appl. No. 14/353,962, filed Apr. 24, 2014, Michael Gramer.
U.S. Appl. No. 13/642,253, Apr. 23, 2014, Julie Zhen Qin Wu.
U.S. Appl. No. 13/642,253, filed Oct. 24, 2012, Aran Frank Labrijn, Sep. 11, 2014, Jessica H. Roark.
Aalberse, Rob C., "Physiological Fab arm exchange of IgG4 generates an anti-inflammatory antibody," Genmab, European Antibody Congress, 36 pages (2008).
Carlring, Jennifer et al., "A Novel Redox Method for Rapid Production of Functional Bi-Specific Antibodies For Use in Early Pilot Studies," PLoS One, vol. 6(7):e22533, pp. 1-6 (2011).
Dall'Acqua, William et al., "Contribution of Domain Interface Residues to the Stability of Antibody CH3 Domain Homodimers," Biochemistry, vol. 37:9266-9273 (1998).
Genmab, "Better Antibodies by Design," www.genmab.com, 2 pages (2011).
Genmab, "Building for a Commercial Future: Research, Development and Business Update," slideshow, 65 pages (2006).
Genmab, "DuoBody platform, Genmab's proprietary bispecific antibody platform," slideshow, 15 pages, (2011).
Genmab, "DuoBody, Genmab's proprietary bispecifiic antibody platform," slideshow, 13 pages (2011).
Genmab, "DuoBody, The next generation of therapeutic antibodies," www.genmab.com, 2 pages (2011).
Genmab, "DuoBody: Innovative Bispecific Antibody Platform," Poster for R&D Day, 1 page (2011).
Genmab, "Genmab, Beter Antibodies by Design," slideshow, 18 page (2011).
Genmab, "The physiological generation of bispecific IgG4 antibodies," Sanquin Spring Symposium, slideshow, 54 pages (2007).
Genmab, "Therapeutic IgG4 antibodies engage in Fab-arm exchange with patients' IgG4 in vivo," Antibodies as Drugs, Poster #214, 14 pages (2009).
Labrijn, Aran F. et al., "Species-Specific Determinants in the IgG CH3 Comain Enable Fab-Arm Exchange by Affecting the Noncovalent CH3-CH3 Interaction Strength," The Journal of Immunology, vol. 187, 9 pages (2011).
Labrijn, Aran F. et al., "Species-specific determinants in the immunoglobulin CH3 domain enable Fab-arm exchange by affecting the non-covalent CH3-CH3 interaction strength," Keystone Symposium, Antibodies as Drugs Poster Presentation, 1 page (2011).
Marvin, Jonathan S. et al., "Recombinant approaches to IgG-like bispecific antibodies," Acta Pharmacologica Sinica, vol. 26(6):649-658 (2005).
Mori, Katsuhiro et al., "Non-fucosylated therapeutic antibodies: the next generation of therapeutic antibodies," Cytotechnology, vol. 55:109-114 (2007).
Ooijevaar-De Heer, Pleuni G. et al., "Fc binding activity of IgG4 is a confounding factor in the measurement of IgG4 bispecificity," Sanquin Spring Symposium, 1 page (2007).
Parren, Paul, "UniBody, a novel nonactivating antibody format," Beyond Antibodies, slideshow, 35 pages (2009).
Rispens, Theo et al., "Human IgG4 Binds to IgG4 and Conformationally Altered IgG1 via Fc-Fc Interactions," The Journal of Immunology, vol. 182:4275-4281 (2009).
Rispens, Theo, "IgG4: an odd antibody, Fc interactions and the relation to half-molecule exchange," Sanquin, slideshow, 41 pages (2009).
Schuurman, Janine et al., "Anti-Inflammatory Activity of Human IgG4 Antibodies by Dynamic Fab Arm Exchange," World BioPharm Forum, Poster, 1 page (2009).
Schuurman, Janine, "IgG4 therapeutic antibodies," World BioPharm Forum, slideshow, 26 pages (2009).
Schuurman, Janine, "Post-Transcriptional Modifications," Genmab, slideshow, 43 pages (2008).
Schuurman, Janine, "The impact of Fab-arm exchange on the development of antibody therapeutics," Antibody Discovery & Development Forum, slideshow, 30 pages (2011).
Schuurman, Janine, "The impact of Fab-arm exchange on the development of antibody therapeutics," Antibody Engineering and Design, slideshow, 29 pages (2011).
Schuurman, Janine, "The impact of Fab-arm exchange on the development of antibody therapeutics," Genmab, slideshow, 26 pages (2010).
Van Berkel, Patrick H.C., "Development of a production process for DuoBody: a novel human bispecific platform," Informa/IBC Life Sciences' Bioproduction Conference, Poster, 1 page (2011).
Van De Winkel, Jan et al., "Better Antibodies by Design, 2011 R&D Day," slideshow, 109 pages (2011).
Van Der Zee, J.S. et al., "Inhibition of complement activation by IgG4 antibodies," Clin. exp. Immunol., vol. 64:415-422 (1986).
International Preliminary Report on Patentability and Written Opinion for Application No. PCT/EP2012/071294, 14 pages, dated Apr. 29, 2014.
International Search Report for Application No. PCT/EP2012/071294, 5 pages, dated Apr. 26, 2013.

* cited by examiner

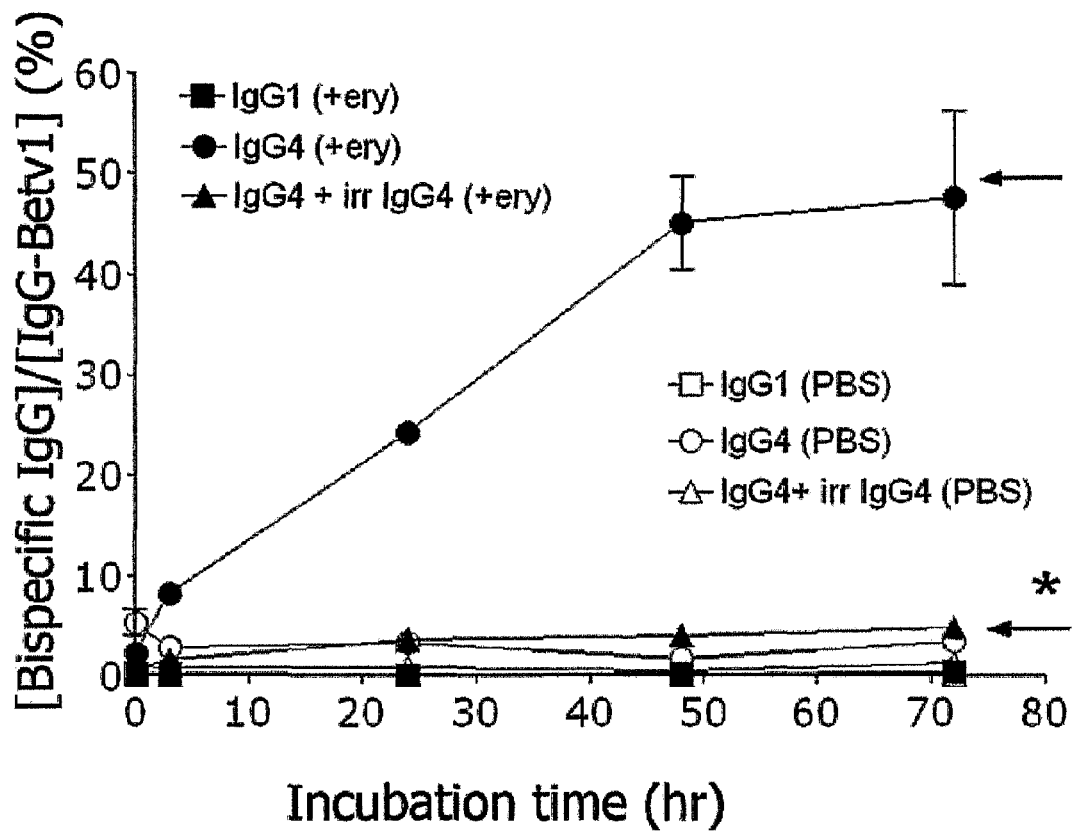

FIGURE 18

SEQ ID NO: 19: aa sequence of IgG1 constant region (accession # P01857)

```
  1 astkgpsvfp lapSskstsg gtaalgclvk dyfpepvtvs wnsgaltsgv
 51 htfpavlqss glyslssvvt vpssslgtqt yicnvnhkps ntkvdkkvep
101 kscdkthtcp pcpapellgg psvflfppkp kdtlmisrtp evtcvvvdvs
151 hedpevkfnw yvdgvevhna ktkpreeqyn styrvvsvlt vlhqdwlngk
201 eykckvsnka lpapiektis kakgqprepq vytlppsRX4e X5tknqvsltc
251 lvkgfypsdi avewesngqp ennykttppv ldsdgsffly sKltvdksrw
301 qQgnvfscsv mhealhnhyt qkslslsPgk
``` wherein X₄ is D or E and X₅ is L or M

SEQ ID NO: 20: aa sequence of the IgG2 constant region (accession # P01859)

```
  1 astkgpsvfp lapcsrstse staalgclvk dyfpepvtvs wnsgaltsgv
 51 htfpavlqss glyslssvvt vpssnfgtqt ytcnvdhkps ntkvdktver
101 kccvecppcp appvagpsvf lfppkpkdtl misrtpevtc vvvdvshedp
151 evqfnwyvdg vevhnaktkp reeqfnstfr vvsvltvvhq dwlngkeykc
201 kvsnkglpap iektisktkg qprepqvytl ppsReemtkn qvsltclvkg
251 fypsdiavew esngqpenny kttppMldsd gsfflysKlt vdksrwqQgn
301 vfscsvmhea lhnhytqksl slsPgk
```

SEQ ID NO: 21: aa sequence of the IgG3 constant region (accession # A23511)

```
  1 astkgpsvfp lapcsrstsg gtaalgclvk dyfpepvtvs wnsgaltsgv
 51 htfpavlqss glyslssvvt vpssslgtqt ytcnvnhkps ntkvdkrvel
101 ktplgdttht cprcpepksc dtpppcprcp epkscdtppp cprcpepksc
151 dtpppcprcp apellggpsv flfppkpkdt lmisrtpevt cvvvdvshed
201 pevqfkwyvd gvevhnaktk preeqynstf rvvsvltvlh qdwlngkeyk
251 ckvsnkalpa piektisktk ggprepqvyt lppsReemtk nqvsltclvk
301 gfypsdiave wesSgqpenn yNttppMlds dgsfflysKl tvdksrwqQg
351 nIfscsvmhe alhnRFtqks lslsPgk
```

SEQ ID No: 22: aa sequence of the IgG4 constant region

```
  1 ASTKGPSVFP LAPCSRSTSE STAALGCLVK DYFPEPVTVS WNSGALTSGV
 51 HTFPAVLQSS GLYSLSSVVT VPSSSLGTKT YTCNVDHKPS NTKVDKRVES
101 KYGPPCPSCP APEFLGGPSV FLFPPKPKDT LMISRTPEVT CVVVDVSQED
151 PEVQFNWYVD GVEVHNAKTK PREEQFNSTY RVVSVLTVLH QDWLNGKEYK
201 CKVSNKGLPS SIEKTISKAK GQPREPQVYT LPPSQEEMTK NQVSLTCLVK
251 GFYPSDIAVE WESNGQPENN YKTTPPVLDS DGSFFLYSRL TVDKSRWQEG
301 NVFSCSVMHE ALHNHYTQKS LSLSLGK
```

BISPECIFIC ANTIBODIES AND METHODS FOR PRODUCTION THEREOF

RELATED APPLICATIONS

This application is a 35 U.S.C. 371 national stage filing of International Application No. PCT/DK/2008/000124 filed Mar. 28, 2008, which claims priority to Denmark Patent Application No. PA 2007-00491 filed Mar. 29, 2007 and U.S. Provisional Patent Application No. 60/920,840 filed Mar. 29, 2007. The contents of the aforementioned applications are hereby incorporated in their entirety by this reference.

FIELD OF THE INVENTION

The present invention relates to novel methods for the production of bispecific antibodies and to bispecific antibodies obtainable by these methods.

BACKGROUND OF THE INVENTION

Human immunoglobulin G (IgG) antibodies exist in four subclasses with distinct structural and functional properties. IgGs are composed of two heavy chain-light chains pairs (half-molecules), which are connected via inter-heavy chain disulfide bonds situated in the hinge region. Human IgG4 molecules exist in various molecular forms which differ by the absence or presence of the inter-heavy chain disulfide bonds located in the hinge region. IgG4 molecules exist in forms in which either both or none of the inter-heavy chain disulfide bonds have been formed (6, 7). However, irrespective of the absence or presence of these inter-chain disulfide bonds (6, 8), human IgG4s exist as tetramers in solution consisting of two Ig heavy and two light chains, as common for immunoglobulin G molecules, due to relatively strong non-covalent interactions between the CH3-domains and between the CH1 and CH2 domains (4). Only upon denaturation under non-reducing conditions, the two non-covalently associated half molecules dissociate as demonstrated by size-determination analysis such as SDS-PAGE (6, 9).

It has been known for several years that human IgG4 antibodies, unlike other IgG subclasses, behave as monovalent molecules in interactions with antigen. It was found that serum-derived human IgG4 cannot precipitate purified antigen, because it cannot crosslink. While such serum-derived IgG4 is functionally monovalent (1, 2), recombinantly produced IgG4, in contrast, is behaving bivalently in interactions with antigens (3). On the basis of these observations, it has been proposed that IgG4 molecules in serum can exchange half-molecules (i.e. a molecule consisting of one heavy chain and one light chain), resulting in the generation of bispecific molecules, which cannot crosslink identical antigens (3-5). This process of half-molecule exchange is also termed "Fab-arm exchange" herein.

Bispecific antibodies have interesting potential as therapeutic drugs, since they can be used, for example, as mediators to retarget effector mechanisms to disease-associated sites. However, one of the major obstacles in the development of bispecific antibodies has been the difficulty of producing the materials in sufficient quality and quantity by traditional technologies, such as the hybrid hybridoma and chemical conjugation methods (10).

WO 2005/062916 describes methods for the formation of multimeric molecules on the basis of IgG4 in vivo in mice. Furthermore, WO 2005/062916 describes that co-incubation of two IgG4 antibodies having different antigen-binding specificities in vitro in a saline buffer leads to the formation of products that are capable of reacting with both antigens. However, it has not been demonstrated in WO 2005/062916 whether these products are aggregates or bispecific antibodies, and the yield of the reaction was low under the conditions used.

SUMMARY OF THE INVENTION

It has now surprisingly been found that under reducing conditions, two IgG4- or IgG4-like antibodies having different antigen-binding specificities can perform highly efficient half-molecule exchange and thus form bispecific antibodies without concomitant formation of aggregates.

Accordingly, in a first main aspect, the invention relates to an ex vivo method for the generation of a bispecific antibody, said method comprising the steps of:

a) providing a first antibody having a first binding specificity, wherein said first antibody comprises an IgG4-like CH3 region, b) providing a second antibody having a second binding specificity which differs from said first binding specificity, wherein said second antibody comprises an IgG4-like CH3 region, c) incubating said first and second antibodies together under reducing conditions which allow the cysteines in the core hinge region to undergo disulfide-bond isomerization, and d) obtaining a bispecific antibody.

Without being bound by any specific theory, it is believed that two regions of an antibody have an important impact on its ability to undergo half-molecule exchange.

Firstly, the ability for half-molecule exchange may be influenced by sequence differences in the core-hinge region of the molecule, since antibodies having a CPSC sequence (SEQ ID NO: 27) in the core hinge region, such as IgG4, exchange more readily than antibodies having a CPPC (SEQ ID NO: 28) core hinge sequence, such as IgG1. Without being bound by any theory, it is hypothesized that the CPSC sequence (SEQ ID NO: 29) results in a more flexible core-hinge and the possibility to form intra-chain disulfide bonds. Remarkably, the structure of the core hinge is similar to the active domain of protein-disulfide-isomerase (PDI), CXXC. These CXXC motifs of different isoforms of PDI catalyze the formation, reduction and rearrangement of disulfide bonds in proteins. Thus, without being bound by any specific theory, it is believed that antibodies having an IgG4-like core hinge sequence may have an intrinsic activity for rearrangement of disulfide bonds, which is stimulated by the conditions used in the methods of the invention.

Secondly, again without being bound by any theory, the results show that to allow the exchange reaction to take place, the sequence of the CH3 region should be IgG4-like, i.e. such that it does not form strong inter-half-molecule interactions.

In another main aspect, the invention relates to an isolated bispecific antibody obtained or obtainable by the method of the invention and to a pharmaceutical composition comprising such an antibody.

In a further aspect, the invention relates to an isolated bispecific antibody comprising two IgG4-like CH3 regions and to a pharmaceutical composition comprising such an antibody.

In an even further aspect, the invention relates to a method for the selection of a bispecific antibody having a desired property, said method comprising the steps of:

a) providing a set of antibodies, wherein each antibody has a different target specificity and wherein each antibody comprises an IgG4-like CH3 region, b) incubating each antibody of said set of antibodies with another antibody of said set under reducing conditions, thus generating a set of antibody mixtures, wherein each mixture contains a different bispecific antibody, c) assaying the resulting set of antibody mixtures for a given desired property, and d) selecting a bispecific antibody mixture having the desired property.

Plasma (10 μl) drawn at t=24 h from a mouse dosed with an IgG4 mix was fractionated on a Superdex200 column. The mouse was dosed with a mix containing 300 μg of Bet v 1 binding IgG4 and 300 μg of Fel d 1 binding IgG4. In the fractions the concentration of Fel d 1 specific IgG (■) was measured in the antigen binding test and the concentration of bispecific IgG Bet v 1-Fel d 1 (●) was determined in the Bet v 1-Fel d 1 cross-linking assay. Calibration of this column using IVIg has revealed that monomeric, dimeric and aggregated IgG elute at 12.9, 11.0 and 8.4 ml, respectively (data not shown).

FIG. 5. Exchange of IgG in whole blood components

Exchange of IgG4 and IgG1 was evaluated by incubating chimeric IgG mixtures in whole blood, blood cells, plasma and serum for 24 h at 37° C., after which bispecific activity in the heterologous cross-linking assay (Fel d 1-Bet v 1) was measured. Blood was obtained from two donors: A (black bars) and B (grey bars). Bispecific activities were determined in mixtures supplemented with chimeric IgG4 (panel A), chimeric IgG1 (panel B) or without the addition of IgG (panel C). All presented data were measured after 24 h of incubation at 37° C.

Figure 6:
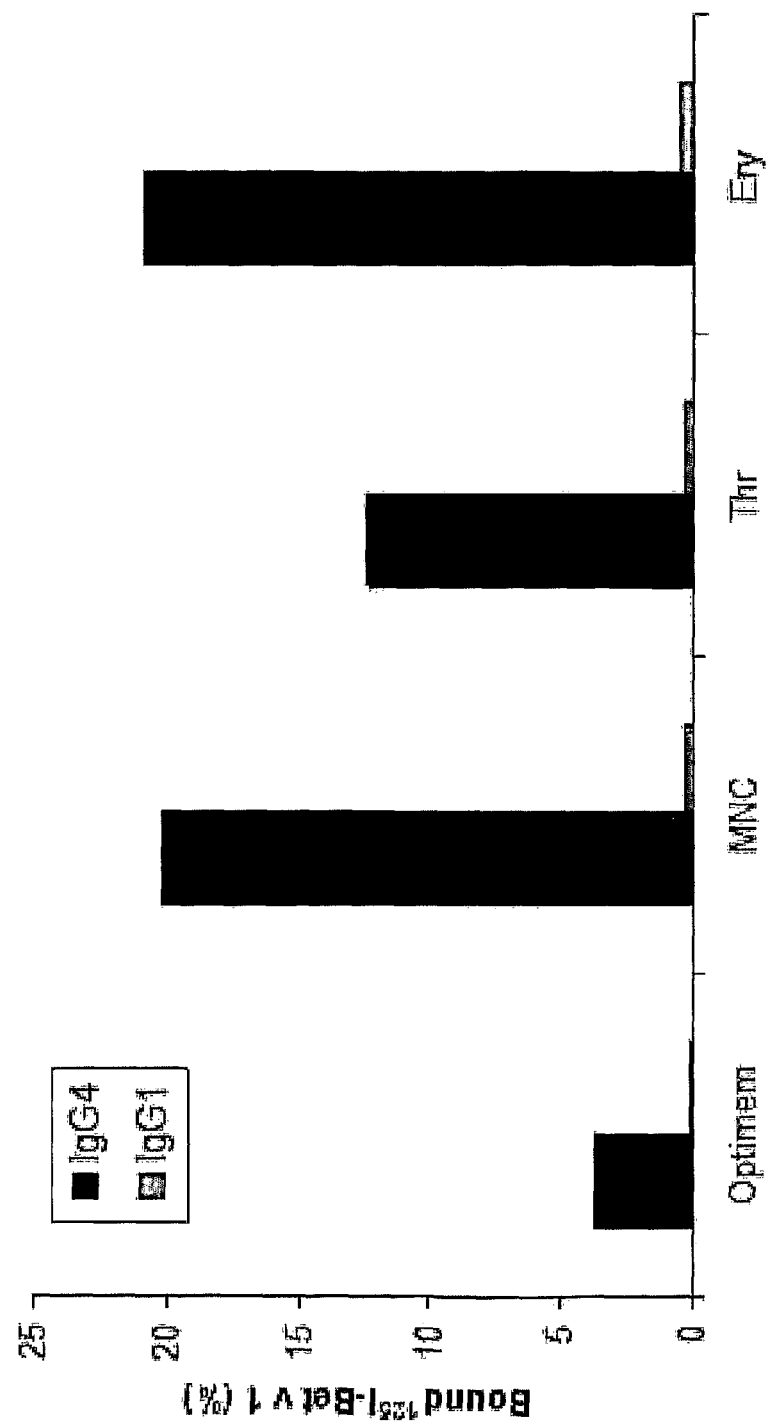

FIG. 6. Exchange of IgG by human blood cells

Exchange of IgG4 (black bars) and IgG1 (grey bars) was evaluated by incubating chimeric IgG mixtures with mononuclear cells (MNC), thrombocytes (Thr) and erythrocytes (Ery) for 48 h at 37° C., after which bispecific activity in the heterologous cross-linking assay (Fel d 1-Bet v 1) was measured. As a control the antibody mixtures were also incubated in serum free culture medium (SFC). Bispecificity is expressed as percentage $^{125}$I-Bet v 1 bound relative to amount added.

Figure 7:
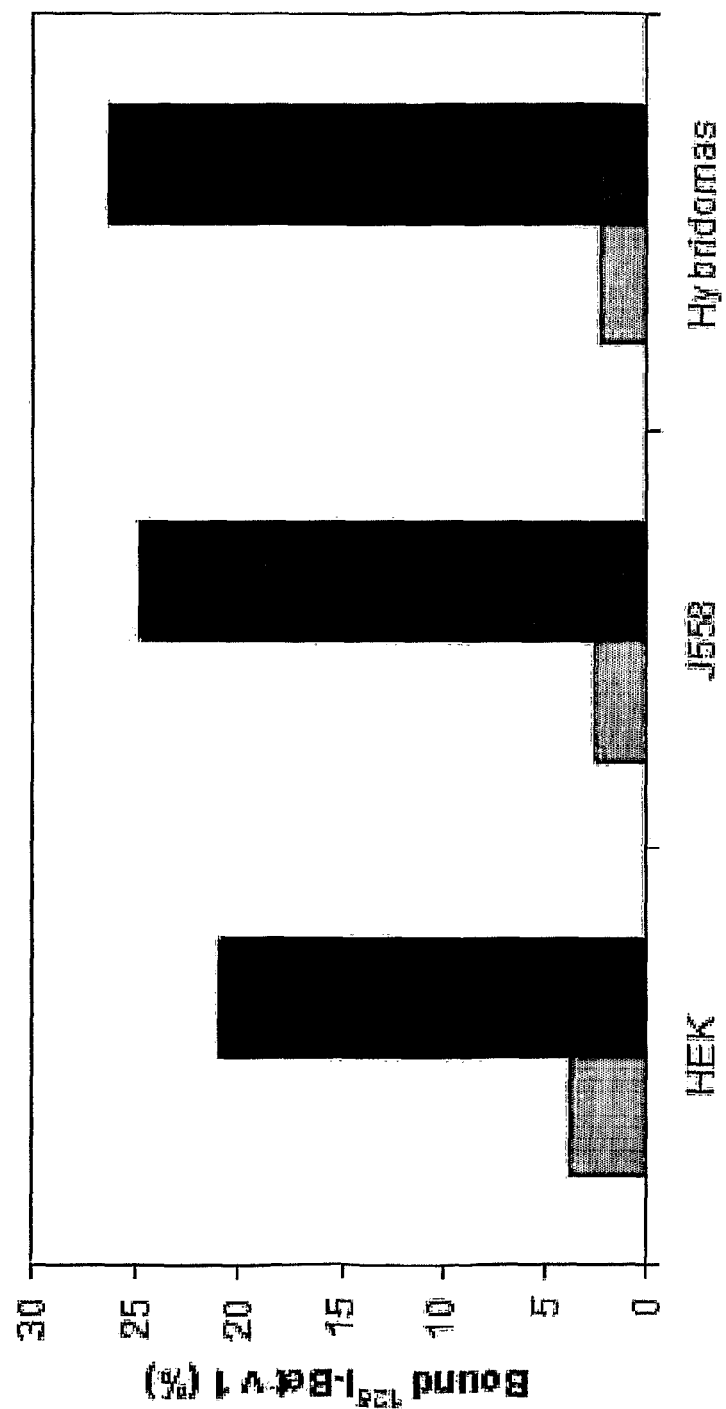

FIG. 7. Exchange of IgG4 by HEK and murine cell lines

Exchange of IgG4 half molecules was evaluated by incubating a chimeric IgG4 mixture with HEK cells, murine B cells (J558) or hybridoma cells at 37° C. Bispecific activity in the heterologous cross-linking assay (Fel d 1-Bet v 1) was measured in samples of 1 μl drawn at t=0 h (grey bars) and at t=24 h (black bars). Bispecificity is expressed as percentage $^{125}$I-Bet v 1 bound relative to amount added.

FIG. 8. Erythrocyte-mediated exchange of IgG4

Incubation of IgG4-Betv1/IgG4-Feld1 mixtures with freshly purified erythrocytes (ery, closed symbols) resulted in the generation of bispecific antibodies, whereas no bispecificity was observed for the mixture of the IgG1 isotypes. As control, antibody mixtures were incubated in PBS without erythrocytes (open symbols). The arrow indicates the maximal expected percentage of bispecific IgG (50%). Error bars represent range of duplicate measurements.

Figure 9A:
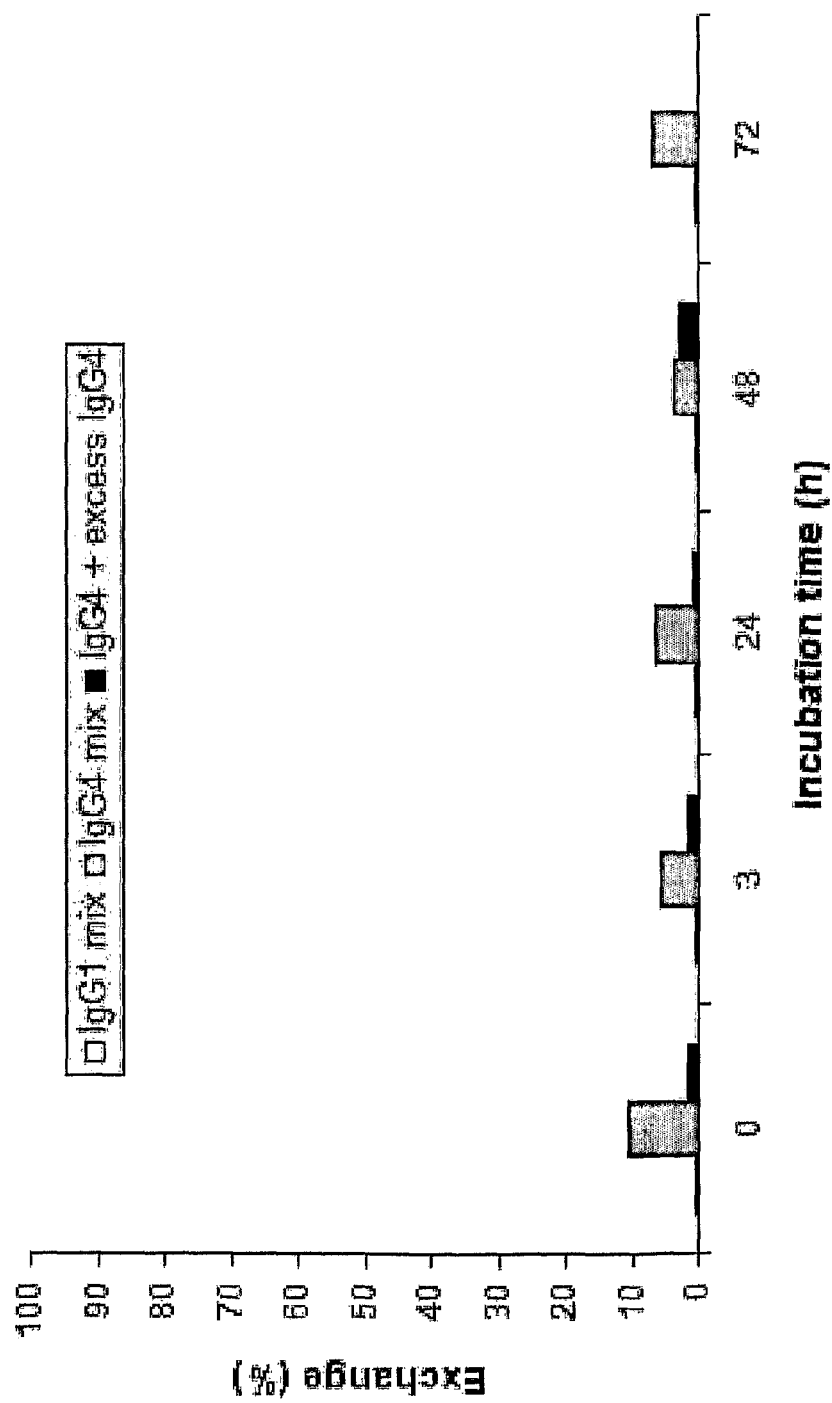

FIG. 9. Exchange of IgG4 in PBS

Exchange in PBS of IgG1 (white bars), IgG4 (grey bars) and IgG4 in the presence of excess irrelevant IgG4 (black bars) was evaluated by measuring bispecific activity (panel A), bivalency and antigen binding. The exchange of IgG half molecules in panel A was calculated from the concentration of bispecific IgG (as determined in the heterologous cross-linking assay) and the maximal expected concentration of bispecific IgG if the exchange of IgG half molecules is random and complete. The exchange was expressed as percentage of the maximal exchange, being 100%. In panel B Fel d 1 bivalency in time is depicted, which was measured in the homologous cross-linking assay. The concentration of bivalent IgG was normalized by setting the concentration of bivalent IgG at t=0 at 100%.

Figure 10:
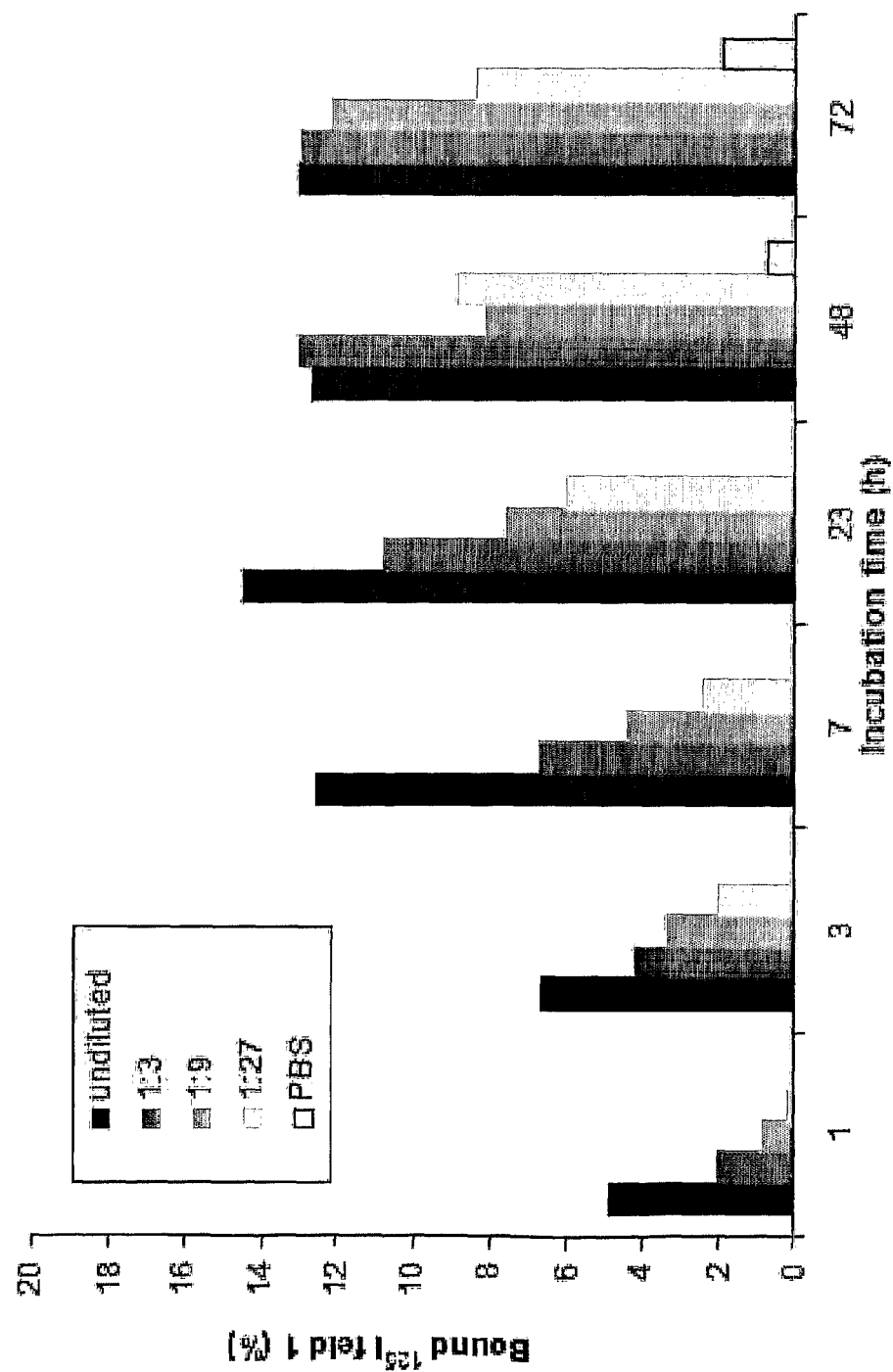

FIG. 10. Exchange of IgG4 by erythrocyte lysate

Exchange of IgG4 half molecules was evaluated by incubating a chimeric IgG4 mixture in lysate from erythrocytes at 37° C. IgG4 was incubated with increasing dilutions of lysate. Bispecific activity in the heterologous cross-linking assay (Bet v 1-Fel d 1) was measured in samples drawn at indicated time points. Bispecificity is expressed as percentage $^{125}$I-Bet v 1 bound relative to amount added.

Figure 11:
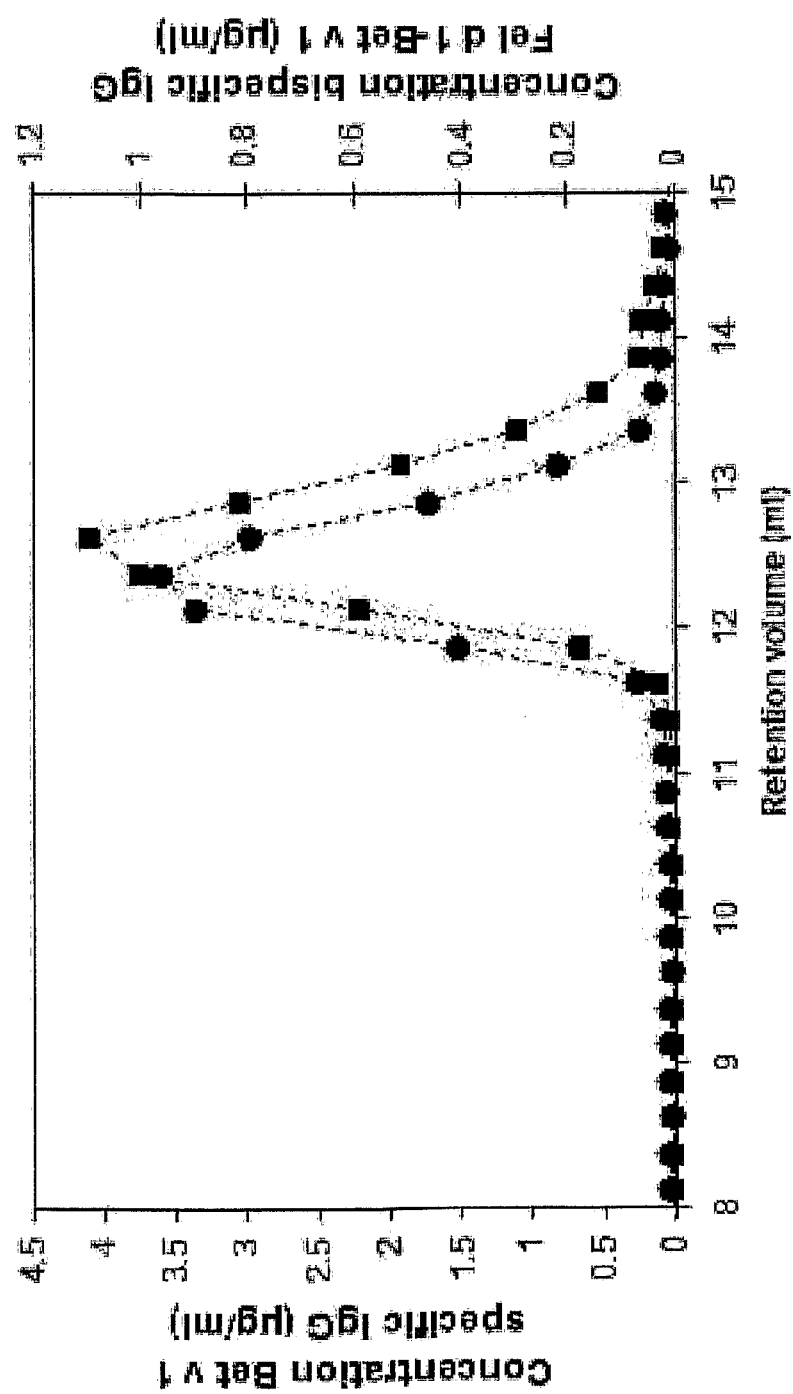

FIG. 11. SEC analysis of bispecific activity induced by erythrocyte lysate

IgG4 was incubated with freshly prepared erythrocyte lysate at 37° C. for 24 h and subsequently fractionated on a Superdex200 column, which was run at 0.5 ml/min on an ÄKTA HPLC unit (Amersham Biosciences, Uppsala, Sweden). In the fractions the concentration of Bet v 1 specific IgG (■) was measured in the antigen binding test and the concentration of bispecific IgG Fel d 1-Bet v 1 (●) was determined in the Bet v 1-Fel d 1 cross-linking assay. Calibration of this column has revealed that monomeric, dimeric and aggregated IgG elute at 12.1, 10.3 and 8.3 ml, respectively (data not shown).

Figure 12:
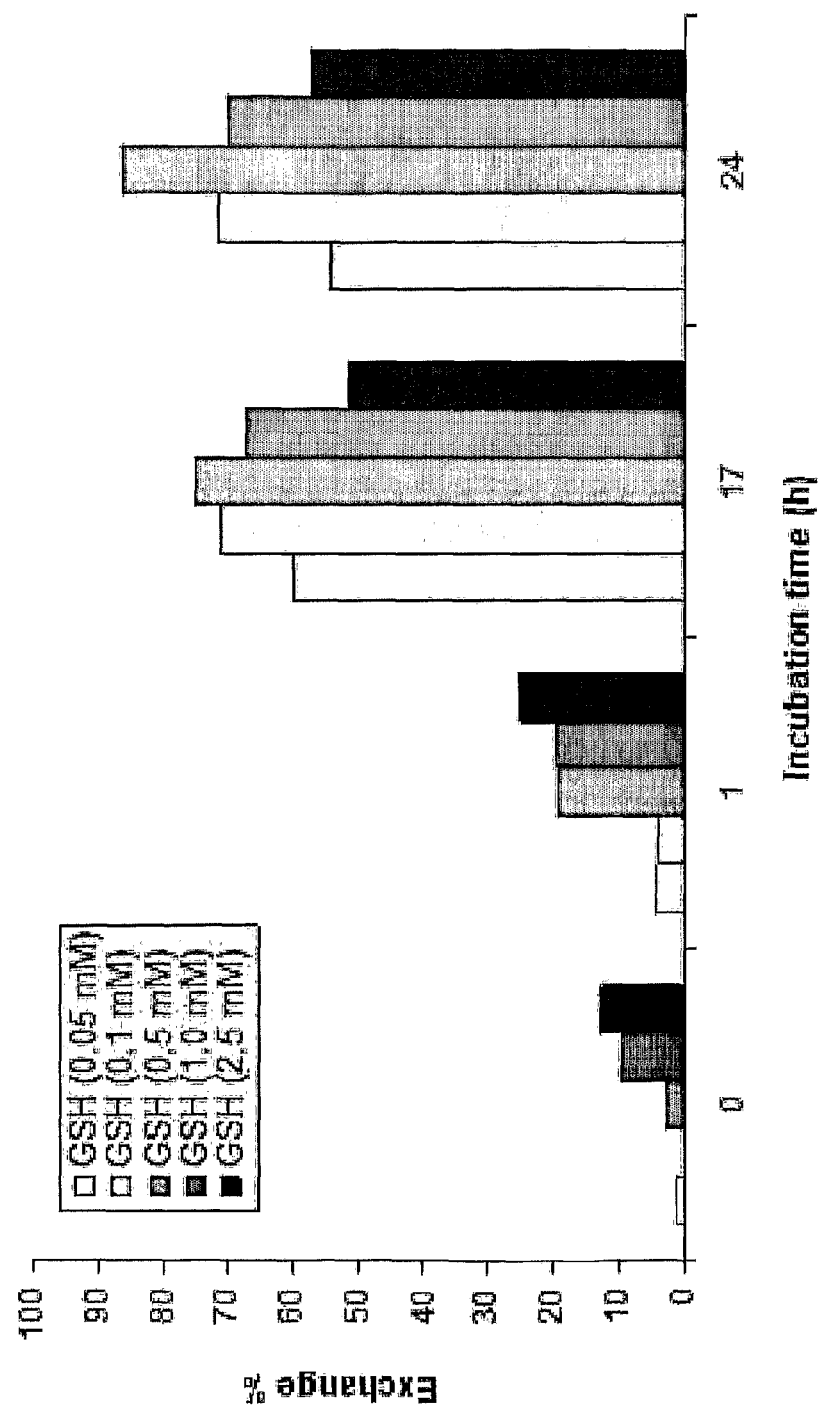

FIG. 12. GSH mediated exchange of IgG4

GSH mediated exchange of IgG4 half molecules was evaluated by incubating IgG4 in the presence of increasing concentrations of GSH in PBS/Azide. At indicated time points samples were drawn in which antigen binding and bispecific activity was measured. The exchange of IgG4 half molecules was calculated from the measured concentration of bispecific IgG (as determined in the heterologous cross-linking assay) and the maximal expected concentration of bispecific IgG4 if the exchange of IgG4 half molecules is random and complete. The exchange was expressed as percentage of the maximal exchange, set at 100%.

Figure 13:
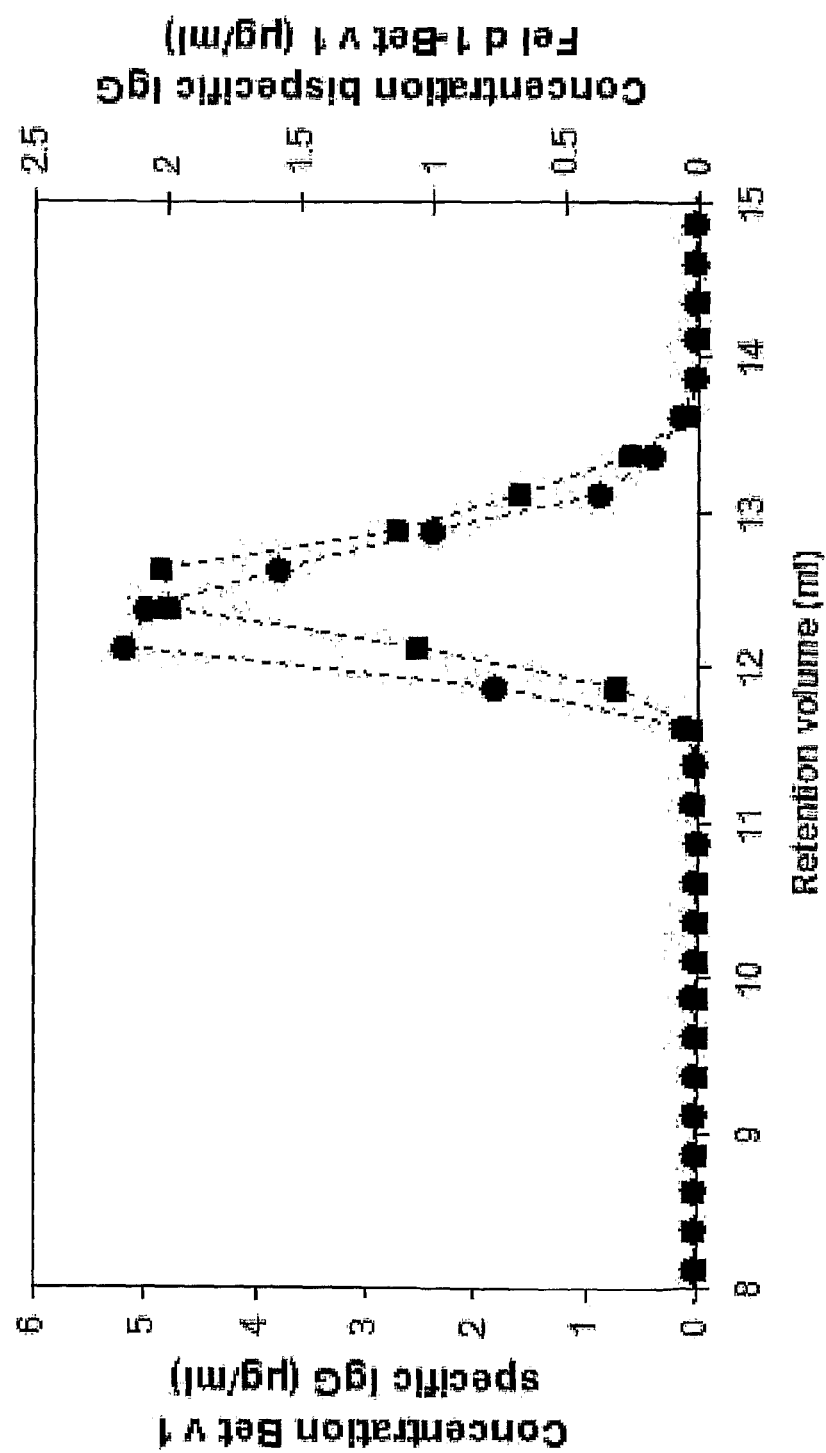

FIG. 13. SEC of GSH mediated exchange of IgG4 half molecules

IgG4 was incubated with GSH (0.5 mM) and subsequently fractionated on a Superdex200 column, which was run at 0.5 ml/min on an ÄKTA HPLC unit (Amersham Biosciences, Uppsala, Sweden). In the fractions the concentration of Bet v 1 specific IgG (■) was measured in the antigen binding test and the concentration of bispecific IgG Fel d 1-Bet v 1 (●) was determined in the Bet v 1-Fel d 1 cross-linking assay. Calibration of this column has revealed that monomeric, dimeric and aggregated IgG elute at 12.1, 10.3 and 8.3 ml, respectively (data not shown).

Figure 14:
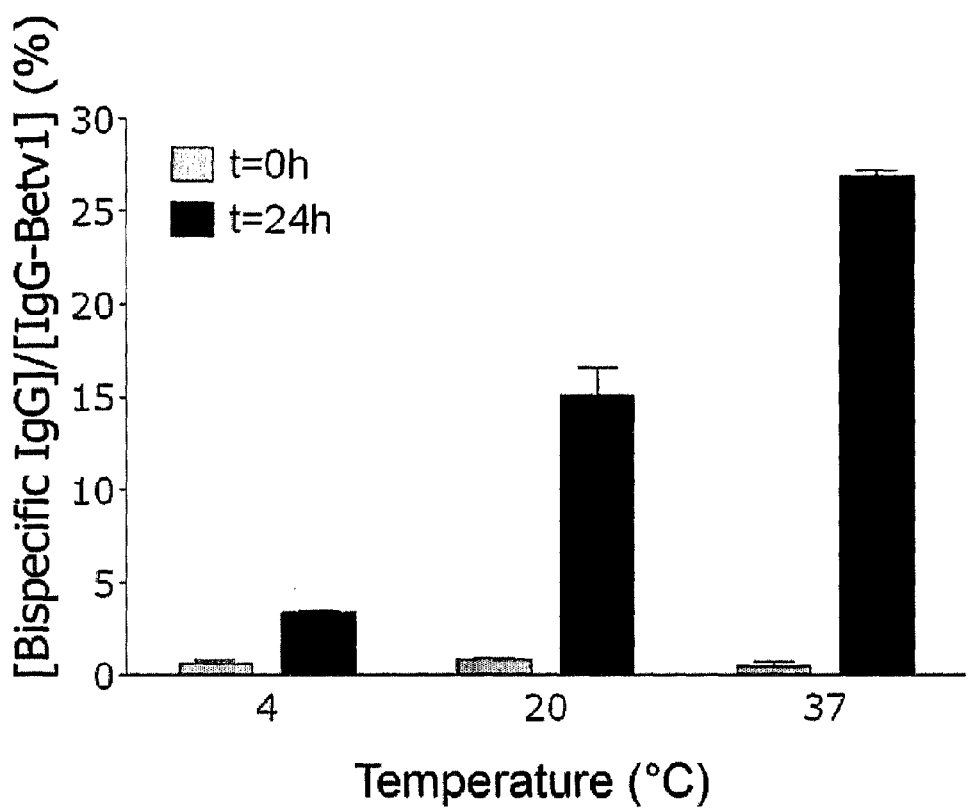

FIG. 14. Temperature dependence of GSH mediated exchange of IgG4. IgG4-Betv1 and IgG4-Feld1 mixtures were incubated in PBS with GSH at indicated temperatures. At t=0 h (grey bars) and t=24 h (black bars) concentrations of bispecific IgG4 were assessed. From these data the fraction of bispecific IgG relative to the IgG4 Betv1 concentration was calculated and expressed as percentage. Error bars represent range of duplicate measurements.

Figure 15:
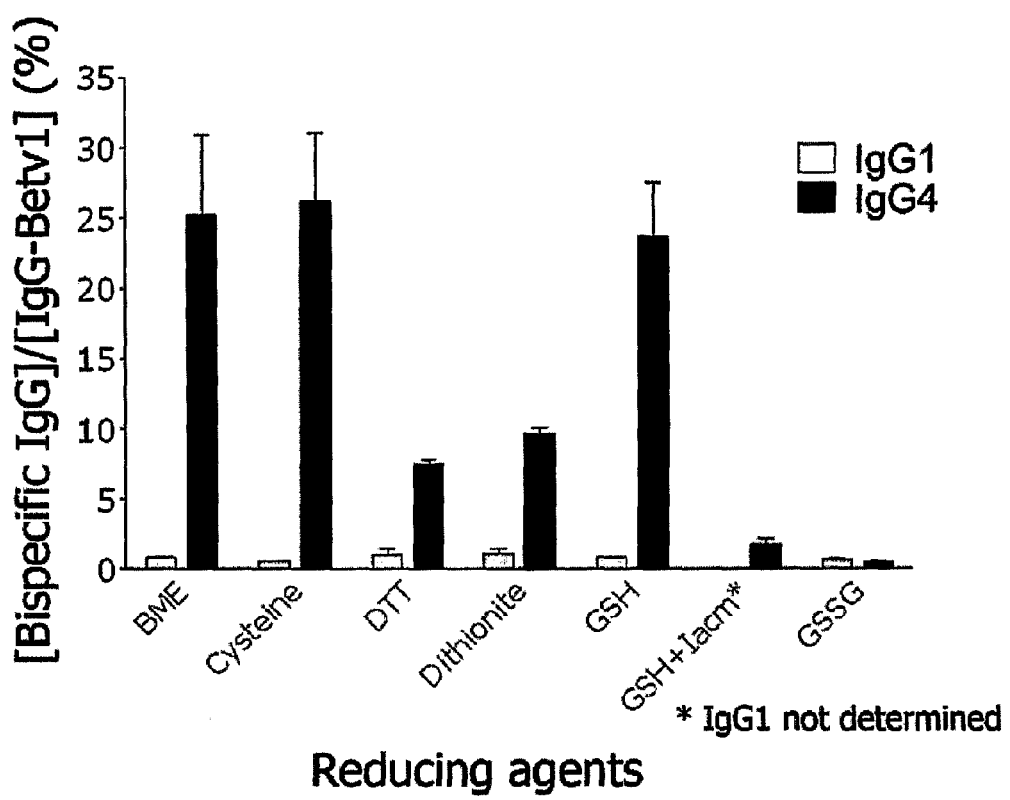

FIG. 15. IgG4 exchange mediated by a panel of reducing agents. IgG4-Betv1 and IgG4-Feld1 in PBS were incubated in the presence of different agents (all reducing, except GSSG) for 24 h at 37° C. The concentration of Bet v 1 specific IgG was measured in the Bet v 1 binding assay and the concentration of bispecific IgG was measured in the heterologous cross-linking assay (Fel d 1-Bet v 1). The percentage of bispecific IgG relative to the IgG-Betv1 concentration was calculated. Standard error bars represent SEM calculated from three measurements.

FIG. 16. Exchange of fully human IgG4 antibodies using GSH.

(A) IgG4-CD20/IgG4-EGFr or IgG1-CD20/IgG1-EGFr mixtures were incubated at 37° C. with or without 0.5 mM GSH. Samples were taken at indicated time points. The formation of bispecific antibodies was measured in a sandwich ELISA. Y-axis indicates the optical density at 405 nm as a measurement of the formation of bispecific CD20/EGFR antibodies.

(B) GSH-dose dependent exchange of IgG4. A mixture of IgG4-CD20 and IgG4-EGFr was incubated for 24 h at 37° C. with concentrations of GSH as indicated. The formation of bispecific antibodies was measured in a sandwich ELISA. The optical density at 405 nm is plotted on the Y-axis as a measurement of the formation of bispecific CD20/EGFR antibodies.

(C) GSH-mediated exchange of IgG4 half molecules is influenced by the components used in the reaction, and occurs in culture medium (Freestyle 293) at lower GSH concentrations.

(D) GSH-mediated exchange of IgG4 half molecules is higher at 0.5 mM GSH than at 5 mM GSH.

(E/F) Detection of Fab arm exchange between IgG4-EGFR and IgG4-CD20 by ESI-TOF mass spectrometry. An IgG4 mixture was incubated for 24 hours in the absence (E) or presence (F) of 0.5 mM GSH, after which the antibodies were deglycosylated with PNGase F and the molecular weights of the resulting antibodies were determined by ESI-TOF mass spectrometry. Shown are the deconvoluted ESI-TOF spectra. Data are representative of 2 experiments.

FIG. 17. Rhesus monkey IVIg participates in Fab arm exchange of recombinant human IgG4 antibodies.

A) Mixtures of two recombinant human IgG4 antibodies (IgG4-CD20 and IgG4-EGFr) were incubated with GSH for 24 h at 37° C., in the presence or absence of purified rhesus monkey immunoglobulins or human IVIg. The formation of bispecific antibodies through Fab arm exchange was measured in a sandwich ELISA.

B) Mixtures of two recombinant human IgG4 antibodies (IgG4-CD20 and IgG4-EGFr) were incubated with GSH for 24 h at 37° C., in the presence or absence of an excess (indicated in parentheses) of purified rhesus monkey immunoglobulins from several animals (source also indicated in parentheses) or human IVIg. The formation of bispecific antibodies through Fab arm exchange was measured in a sandwich ELISA.

C) Mixtures of two recombinant human IgG4 antibodies (IgG4-CD20 and IgG4-EGFr) were incubated with GSH for 24 h at 37° C., in the presence or absence of an excess (indicated in parentheses) of purified chimpanzee, baboon, cynomolgus monkey, horse and swine immunoglobulins (source also indicated in parentheses) or human IVIg. The formation of bispecific antibodies through Fab arm exchange was measured in a sandwich ELISA.

FIG. 18. Constant region sequences Underlined sequences represent the CH3 region.

Figure 19A:
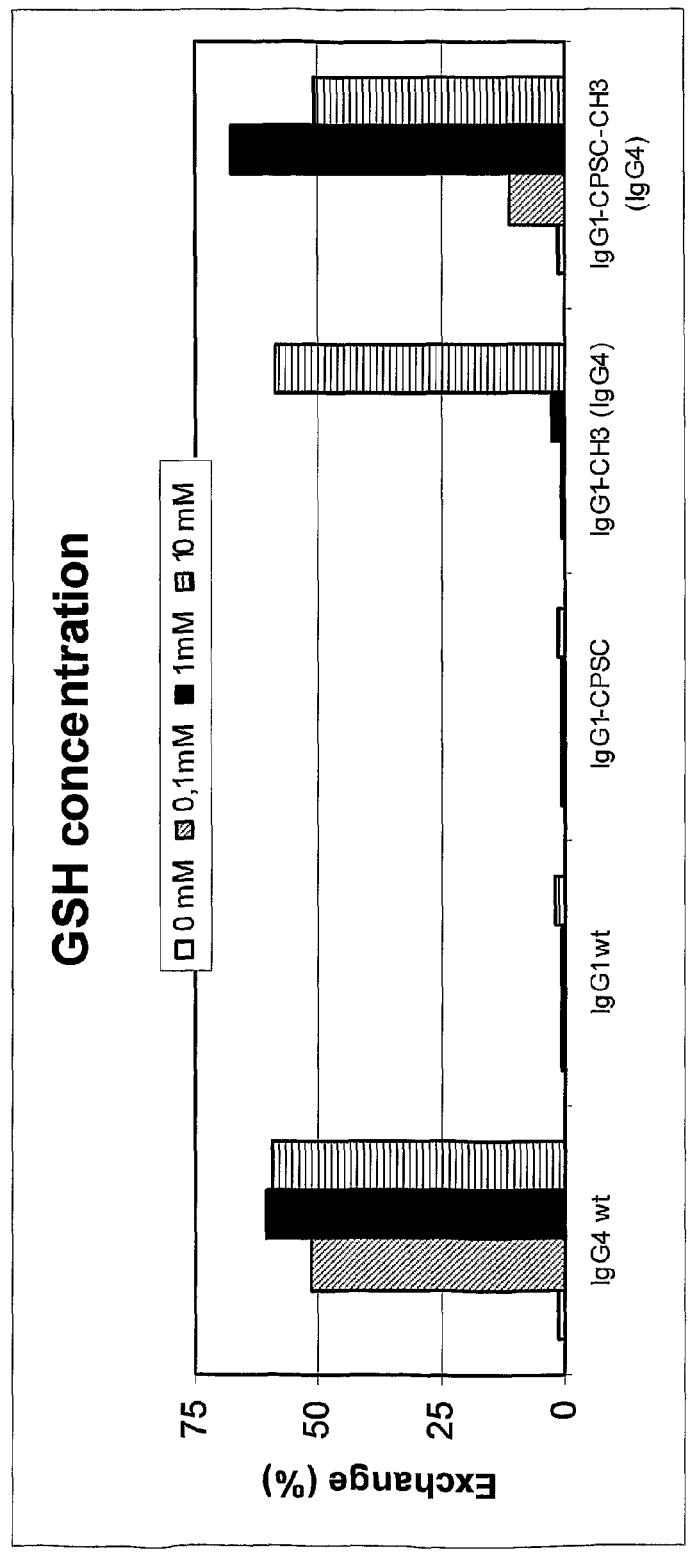

FIG. 19. GSH mediated half molecule exchange of IgG1 mutants (A) The effect of GSH concentration on the half molecule exchange from different IgG1 mutants was tested using 0, 0.1, 1 and 10 mM GSH. Exchange was tested using the following mixtures:

IgG4 a-feld1 wt with IgG4 a-betv1 wt (indicated as IgG4 wt in the figure)
IgG1 a-feld1 wt with IgG4 a-betv1 wt (indicated as IgG1 wt)
IgG1 a-feld1 CPSC with IgG1 a-betv1 CPSC (indicates as IgG1-CPSC)
IgG1 a-feld1 CH3(IgG4) with IgG1 a-betv1 CH3(IgG4) (indicated as IgG1-CH3 (IgG4))
IgG1 a-feld1 CPSC-CH3(IgG4) with a-betv1 IgG1 CPSC-CH3(IgG4)) (indicated as IgG1-CPSC-CH3(IgG4))

(B) The effect of GSH concentration on the half molecule exchange from different IgG1 mutants with IgG4 wt molecules was tested using 0.5 and 5 mM GSH. Exchange was tested using the following mixtures:

IgG1 a-feld1 wt with IgG4 a-betv1 wt (indicated as IgG1)
IgG1 a-feld1 CPSC with IgG4 a-betv1 wt (indicated as IgG1-CPSC)
IgG1 a-feld1 CH3(IgG4) with IgG4 a-betv1 wt (indicated as IgG1-CH3(IgG4))
IgG1 a-feld1 CPSC-CH3(IgG4) with IgG4 a-betv1 wt (indicated as IgG1-CPSC-CH3(G4))
IgG1 a-feld1 R238Q with IgG4 a-betv1 wt (indicated as IgG1-R238Q)
IgG1 a-feld1 K292R with IgG4 a-betv1 wt (indicated as IgG1-K292R)
IgG1 a-feld1 Q302E with IgG4 a-betv1 wt (indicated as IgG1-Q302E)
IgG1 a-feld1 P328L with IgG4 a-betv1 wt (indicated as IgG1-P328L)

IgG1 a-feld1 CPSC-K292R with IgG4 a-betv1 wt (indicated as IgG1-CPSC-K292R)
IgG4 a-feld1 wt with IgG4 a-betv1 wt (indicated as IgG4)

(C) The effect of GSH concentration on the half molecule exchange from different IgG1 mutants was tested using 0.5 and 5 mM GSH. Exchange was tested using the following mixtures:

IgG1 a-feld1 wt with IgG1 a-betv1 wt (indicated as IgG1)
IgG1 a-feld1 CPSC with IgG1 a-betv1 CPSC (indicated as IgG1-CPSC)
IgG1 a-feld1 CH3(IgG4) with IgG1 a-betv1 CH3(IgG4) (indicated as IgG1-CH3(IgG4))
IgG1 a-feld1 CPSC-CH3(IgG4) with IgG1 a-betv1 CPSC-CH3(IgG4) (indicated as IgG1-CPSC-CH3(IgG4))
IgG1 a-feld1 R238Q with IgG1 a-betv1 R238Q (indicated as IgG1-R238Q)
IgG1 a-feld1 K292R with IgG1 a-betv1 K292R (indicated as IgG1-K292R)
IgG1 a-feld1 Q302E with IgG1 a-betv1 Q302E (indicated as IgG1-Q302E)
IgG1 a-feld1 P328L with IgG1 a-betv1 P328L (indicated as IgG1-P328L)
IgG1 a-feld1 CPSC-K292R with IgG1 a-betv1 CPSC-K292R (indicated as IgG1-CPSC-K292R)
IgG4 a-feld1 wt with IgG4 a-betv1 wt (indicated as IgG4)

FIG. 20. At 0.5 mM GSH, IgG4 molecules with a wild-type (IgG4) core hinge participate in Fab arm exchange of recombinant human IgG4 antibodies, whereas molecules with a IgG1 core hinge do not. (A) Mixtures of two recombinant human IgG4 antibodies (IgG4-CD20 and IgG4-EGFr, as described above) were incubated with 0.5 mM GSH for 24 h at 37° C., in the presence or absence of an excess (50 and 100 micrograms/ml) of Tysabri. The formation of bispecific antibodies through Fab arm exchange was measured in a sandwich ELISA. (B) Mixtures of two recombinant human IgG4 antibodies (IgG4-CD20 and IgG4-EGFr, as described above) were incubated with 0.5 mM GSH for 24 h at 37° C., in the presence or absence of equimolar amounts (10 micrograms/ml) of Tysabri or Mylotarg. The formation of bispecific antibodies through Fab arm exchange was measured in a sandwich ELISA FIG. 21. Half molecule exchange of IgG1-CPSC constructs with additional mutations at position 292. Half molecule exchange from different IgG1 mutants was tested using 0.5 mM GSH. Exchange was tested using the following mixtures:

IgG1-2F8 wt with IgG1-7D8 wt (indicated as IgG1)
IgG1-2F8-CPSC with IgG1-7D8-CPSC (indicated as IgG1-CPSC)
IgG1-2F8-CH3(IgG4) with IgG1-7D8-CH3(IgG4) (indicated as IgG1-CH3(IgG4))
IgG1-2F8-CPSC-CH3(IgG4) with IgG1-7D8-CPSC-CH3(IgG4) (indicated as IgG1-CPSC-CH3(IgG4))
IgG1-2F8-CPSC-R238Q with IgG1-7D8-CPSC-R238Q (indicated as IgG1-CPSC-R238Q)
IgG1-2F8-CPSC-K292R with IgG1-7D8-CPSC-K292R (indicated as IgG1-CPSC-K292R)
IgG1-2F8-CPSC-K292Y with IgG1-7D8-CPSC-K292Y (indicated as IgG1-CPSC-K292Y)
IgG1-2F8-CPSC-K292F with IgG1-7D8-CPSC-K292F (indicated as IgG1-CPSC-K292F)
IgG1-2F8-CPSC-K292W with IgG1-7D8-CPSC-K292W (indicated as IgG1-CPSC-K292W)
IgG1-2F8-CPSC-Q302E with IgG1-7D8-CPSC-Q302E (indicated as IgG1-CPSC-Q302E)
IgG1-2F8-CPSC-P328L with IgG1-7D8-CPSC-P328L (indicated as IgG1-CPSC-P328L)
IgG4-2F8 wt with IgG4-7D8 wt (indicated as IgG4)

The formation of bispecific antibodies through Fab arm exchange was measured in a sandwich ELISA.

FIG. 22. Core-hinge stabilization protects IgG4 antibody therapeutics from Fab-arm exchange in vivo. (A) Detection of Fab-arm exchange between IgG4-EGFR-CPPC and IgG4-CD20 by ESI-TOF mass spectrometry. An IgG4-EGFR-CPPC/IgG4-CD20 mixture was incubated for 24 hours in the presence (F) of 5 mM GSH, after which the antibodies were deglycosylated with PNGase F and the molecular weights of the resulting antibodies were determined by ESI-TOF mass spectrometry. Shown are the deconvoluted ESI-TOF spectra. Bispecific EGFR/CD20 antibodies could be detected when 5 mM GSH was used (incubation without GSH or in the presence of 0.5 mM GSH did not result in bispecific antibodies (data not shown)).

(B) Groups (n=4) of SCID mice were injected with antibody mixtures (300 µg of each) of IgG4-CD20/IgG4-EGFR (open circles), IgG4-CD20/IgG1-EGFR and IgG4-CD20/IgG4-EGFR-CPPC. The generation of bispecific antibodies was followed over time and quantified by ELISA. Bispecific antibodies were quantified using an in vitro exchanged antibody mixture as reference. Data points represent mean±SEM values of four mice, measured at least twice in separate experiments. No bispecific antibodies could be detected in the IgG4-CD20/IgG1-EGFR and IgG4-CD20/IgG4-EGFR-CPPC mixtures. The detection limit of the assays is indicated (dotted line) and represents serum levels of 2000 ng/ml.

Figure 23:
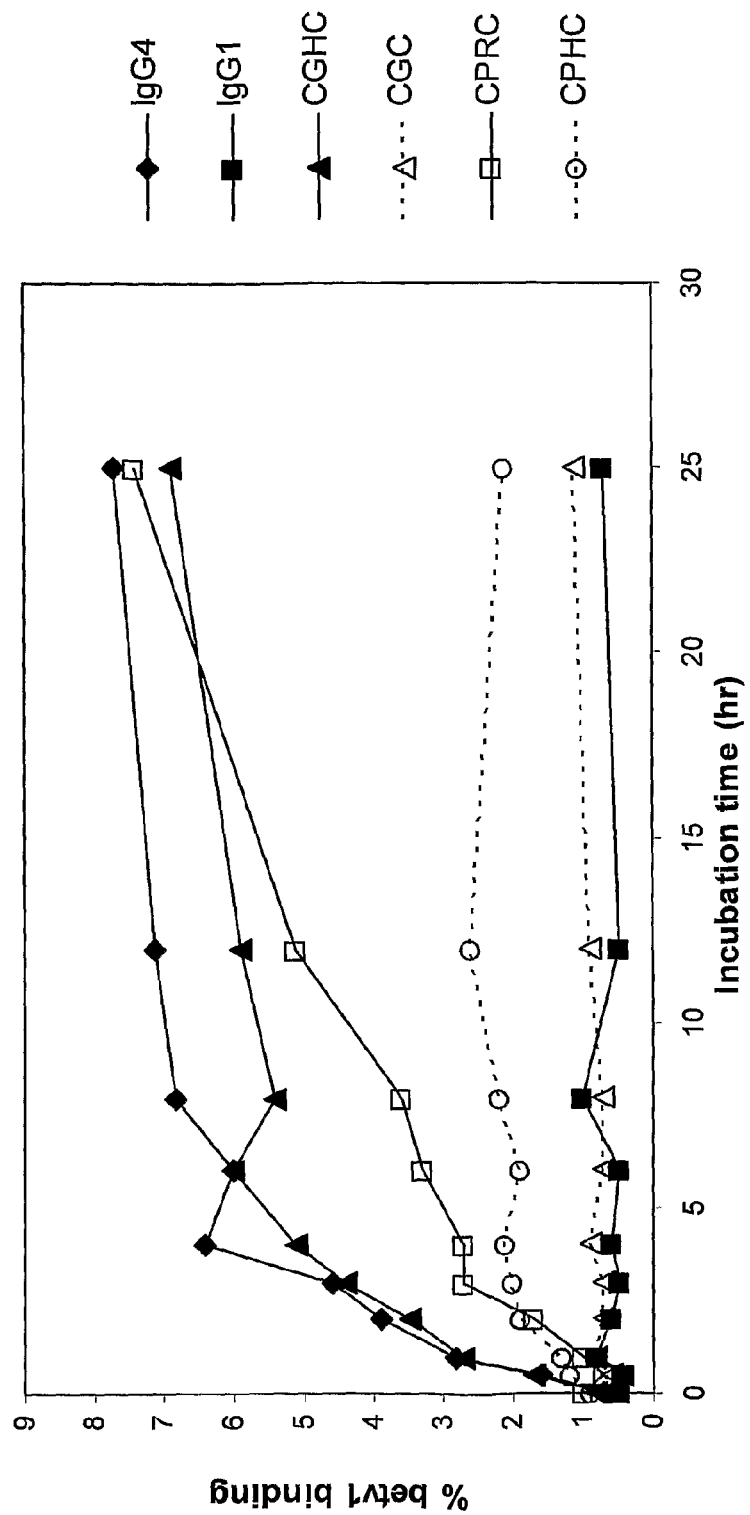

FIG. 23: Fab arm exchange of CXXC-mutants over time.

Mixtures of CXXC-mutant antibodies were incubated at 37° C. with 0.5 mM GSH. Samples were taken at indicated time points. The formation of bispecific antibodies was measured. Exchange was tested using the following mixtures:

IgG1 a-feld1 wt with IgG1 a-betv1 wt (indicated as IgG1)
IgG4 a-feld1 wt with IgG4 a-betv1 wt (indicated as IgG4)
IgG4 a-feld1 CGHC with IgG4 a-betv1 CGHC (indicated as CGHC)
IgG4 a-feld1 CGC with IgG4 a-betv1 CGC (indicated as CGC)
IgG4 a-feld1 CPRC with IgG4 a-betv1 CPRC (indicated as CPRC)
IgG4 a-feld1 CPHC with IgG4 a-betv1 CPHC (indicated as CPHC)

Figure 24:
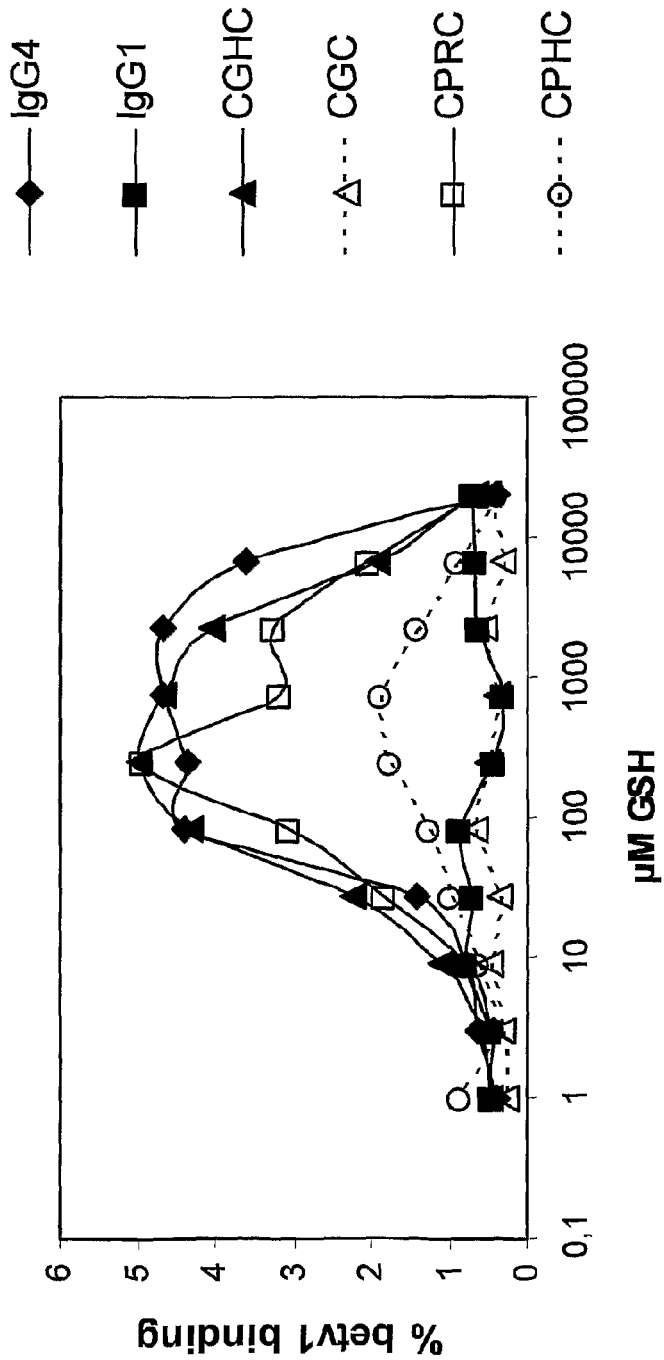

FIG. 24: GSH mediated Fab arm exchange of CXXC-mutants

The effect of GSH concentration on the Fab arm exchange from CXXC-mutants was tested using 1 to 20,000 µM GSH. Exchange was tested using the following mixtures:

IgG1 a-feld1 wt with IgG1 a-betv1 wt (indicated as IgG1)
IgG4 a-feld1 wt with IgG4 a-betv1 wt (indicated as IgG4)
IgG4 a-feld1 CGHC with IgG4 a-betv1 CGHC (indicated as CGHC)
IgG4 a-feld1 CGC with IgG4 a-betv1 CGC (indicated as CGC)
IgG4 a-feld1 CPRC with IgG4 a-betv1 CPRC (indicated as CPRC)
IgG4 a-feld1 CPHC with IgG4 a-betv1 CPHC (indicated as CPHC)

DETAILED DESCRIPTION OF THE INVENTION

Definitions

The term "immunoglobulin" refers to a class of structurally related glycoproteins consisting of two pairs of polypeptide chains, one pair of light (L) low molecular weight chains and one pair of heavy (H) chains, all four inter-connected by disulfide bonds. The structure of immunoglobulins has been well characterized. See for instance Fundamental Immunology Ch. 7 (Paul, W., ed., 2nd ed. Raven Press, N.Y. (1989)) (11). Briefly, each heavy chain typically is comprised of a heavy chain variable region (abbreviated herein as $V_H$ or VH) and a heavy chain constant region. The heavy chain constant region typically is comprised of three domains, CH1, CH2, and CH3. Each light chain typically is comprised of a light chain variable region (abbreviated herein as $V_L$ or VL) and a light chain constant region. The light chain constant region typically is comprised of one domain, $C_L$. The $V_H$ and $V_L$ regions may be further subdivided into regions of hypervariability (or hypervariable regions which may be hypervariable in sequence and/or form of structurally defined loops), also termed complementarity determining regions (CDRs), interspersed with regions that are more conserved, termed framework regions (FRs). Each $V_H$ and $V_L$ is typically composed of three CDRs and four FRs, arranged from amino-terminus to carboxy-terminus in the following order: FR1, CDR1, FR2, CDR2, FR3, CDR3, FR4 (see also (12)). Typically, the numbering of amino acid residues in this region is performed by the method described in Kabat (13). Using this numbering system, the actual linear amino acid sequence of a peptide may contain fewer or additional amino acids corresponding to a shortening of, or insertion into, a FR or CDR of the variable domain. For example, a heavy chain variable domain may include a single amino acid insert (residue 52a according to Kabat) after residue 52 of $V_H$ CDR2 and inserted residues (for instance residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

The term "antibody" (Ab) in the context of the present invention refers to an immunoglobulin molecule, a fragment of an immunoglobulin molecule, or a derivative of either thereof, which has the ability to specifically bind to an antigen under typical physiological conditions with a half life of significant periods of time, such as at least about 30 minutes, at least about 45 minutes, at least about one hour, at least about two hours, at least about four hours, at least about 8 hours, at least about 12 hours, about 24 hours or more, about 48 hours or more, about 3, 4, 5, 6, 7 or more days, etc., or any other relevant functionally-defined period (such as a time sufficient to induce, promote, enhance, and/or modulate a physiological response associated with antibody binding to the antigen and/or time sufficient for the antibody to recruit an Fc-mediated effector activity). The variable regions of the heavy and light chains of the immunoglobulin molecule contain a binding domain that interacts with an antigen. The constant regions of the antibodies (Abs) may mediate the binding of the immunoglobulin to host tissues or factors, including various cells of the immune system (such as effector cells) and components of the complement system such as C1q, the first component in the classical pathway of complement activation. As indicated above, the term antibody herein, unless otherwise stated or clearly contradicted by context, includes fragments of an antibody that comprise a mutated or wildtype core hinge region and retain the ability to specifically bind to the antigen.

It has been shown that the antigen-binding function of an antibody may be performed by fragments of a full-length antibody. Examples of binding fragments encompassed within the term "antibody" include, e.g. F(ab')$_2$ fragments, which are bivalent fragments comprising two Fab fragments linked by a disulfide bridge at the hinge region. Although such fragments are generally included within the meaning of antibody, they collectively and each independently are unique features of the present invention, exhibiting different biological properties and utility. It also should be understood that the term antibody, unless specified otherwise, also includes polyclonal antibodies, monoclonal antibodies (mAbs), antibody-like polypeptides, such as chimeric antibodies and humanized antibodies, and antibody fragments retaining the ability to specifically bind to the antigen (antigen-binding fragments) provided by any known technique, such as enzymatic cleavage, peptide synthesis, and recombinant techniques. An antibody as generated can possess any isotype.

The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

An "isolated antibody," as used herein, is intended to refer to an antibody which is substantially free of other antibodies having different antigenic specificities. An isolated antibody that specifically binds to an epitope, isoform or variant of a particular human target antigen may, however, have cross-reactivity to other related antigens, for instance from other species (such as species homologs). Moreover, an isolated antibody may be substantially free of other cellular material and/or chemicals. In one embodiment of the present invention, a combination of "isolated" monoclonal antibodies having different specificities are combined in a well-defined composition.

The terms "monoclonal antibody" or "monoclonal antibody composition" as used herein refer to a preparation of antibody molecules of single molecular composition. A monoclonal antibody composition displays a single binding specificity and affinity for a particular epitope. Accordingly, the term "human monoclonal antibody" refers to antibodies displaying a single binding specificity which have variable and constant regions derived from human germline immunoglobulin sequences. The human monoclonal antibodies may be generated by a hybridoma which includes a B cell obtained from a transgenic or transchromosomal nonhuman animal, such as a transgenic mouse, having a genome comprising a human heavy chain transgene and a light chain transgene, fused to an immortalized cell.

As used herein, the term "binding" in the context of the binding of an antibody to a predetermined antigen typically is a binding with an affinity corresponding to a $K_D$ of about $10^{-7}$ M or less, such as about $10^{-8}$ M or less, such as about $10^{-9}$ M or less, about $10^{-10}$ M or less, or about $10^{-11}$ M or even less when determined by for instance surface plasmon resonance (SPR) technology in a BIAcore 3000 instrument using the antigen as the ligand and the antibody as the analyte, and binds to the predetermined antigen with an affinity corresponding to a $K_D$ that is at least ten-fold lower, such as at least 100 fold lower, for instance at least 1000 fold lower, such as at least 10,000 fold lower, for instance at least 100,000 fold lower than its affinity for binding to a non-specific antigen (e.g., BSA, casein) other than the predetermined antigen or a closely-related antigen. The amount with which the affinity is lower is dependent on the $K_D$ of the antibody, so that when the $K_D$ of the antibody is very low (that is, the antibody is highly specific), then the amount with which the affinity for the antigen is lower than the affinity for a non-specific antigen may be at least 10,000 fold.

The term "$k_d$" ($sec^{-1}$), as used herein, refers to the dissociation rate constant of a particular antibody-antigen interaction. Said value is also referred to as the $k_{off}$ value.

The term "$k_a$" ($M^{-1} \times sec^{-1}$), as used herein, refers to the association rate constant of a particular antibody-antigen interaction.

The term "$K_D$" (M), as used herein, refers to the dissociation equilibrium constant of a particular antibody-antigen interaction.

The term "$K_A$" ($M^{-1}$), as used herein, refers to the association equilibrium constant of a particular antibody-antigen interaction and is obtained by dividing the $k_a$ by the $k_d$.

As used herein, "isotype" refers to the immunoglobulin class (for instance IgG1, IgG2, IgG3, IgG4, IgD, IgA, IgE, or IgM) that is encoded by heavy chain constant region genes.

The term "epitope" means a protein determinant capable of specific binding to an antibody. Epitopes usually consist of surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents. The epitope may comprise amino acid residues directly involved in the binding (also called immunodominant component of the epitope) and other amino acid residues, which are not directly involved in the binding, such as amino acid residues which are effectively blocked by the specifically antigen binding peptide (in other words, the amino acid residue is within the footprint of the specifically antigen binding peptide).

As used herein, a human antibody is "derived from" a particular germline sequence if the antibody is obtained from a system using human immunoglobulin sequences, for instance by immunizing a transgenic mouse carrying human immunoglobulin genes or by screening a human immunoglobulin gene library, and wherein the selected human antibody is at least 90%, such as at least 95%, for instance at least 96%, such as at least 97%, for instance at least 98%, or such as at least 99% identical in amino acid sequence to the amino acid sequence encoded by the germline immunoglobulin gene. Typically, outside the heavy chain CDR3, a human antibody derived from a particular human germline sequence will display no more than 20 amino acid differences, e.g. no more than 10 amino acid differences, such as no more than 5, for instance no more than 4, 3, 2, or 1 amino acid difference from the amino acid sequence encoded by the germline immunoglobulin gene.

The term "bispecific antibody" is intended to include any antibody, which has two different binding specificities, i.e. the antibody binds two different epitopes, which may be located on the same target antigen or, more commonly, on different target antigens.

As used herein, the term "effector cell" refers to an immune cell which is involved in the effector phase of an immune response, as opposed to the cognitive and activation phases of an immune response. Exemplary immune cells include a cell of a myeloid or lymphoid origin, for instance lymphocytes (such as B cells and T cells including cytolytic T cells (CTLs)), killer cells, natural killer cells, macrophages, monocytes, eosinophils, polymorphonuclear cells, such as neutrophils, granulocytes, mast cells, and basophils. Some effector cells express specific Fc receptors and carry out specific immune functions. In some embodiments, an effector cell is capable of inducing antibody-dependent cellular cytotoxicity (ADCC), such as a natural killer cell, capable of inducing ADCC. For example, monocytes, macrophages, which express FcR are involved in specific killing of target cells and presenting antigens to other components of the immune system, or binding to cells that present antigens. In some embodiments, an effector cell may phagocytose a target antigen or target cell. The expression of a particular FcR on an effector cell may be regulated by humoral factors such as cytokines. For example, expression of FcγRI has been found to be up-regulated by interferon γ (IFN-γ) and/or G-CSF. This enhanced expression increases the cytotoxic activity of FcγRI-bearing cells against targets. An effector cell can phagocytose or lyse a target antigen or a target cell.

"Treatment" refers to the administration of an effective amount of a therapeutically active compound of the present invention with the purpose of easing, ameliorating, arresting or eradicating (curing) symptoms or disease states.

An "effective amount" refers to an amount effective, at dosages and for periods of time necessary, to achieve a desired therapeutic result. A therapeutically effective amount of an antibody may vary according to factors such as the disease state, age, sex, and weight of the individual, and the ability of the antibody to elicit a desired response in the individual. A therapeutically effective amount is also one in which any toxic or detrimental effects of the antibody or antibody portion are outweighed by the therapeutically beneficial effects.

The term "IgG4-like core hinge region" refers to a core hinge region in which the cysteine residues are significantly more susceptible to reduction and/or disulfide bond isomerization than other cysteines/disulfide bridges in the antibody molecule. Thus, for antibodies having an IgG4-like core hinge region, reducing conditions can be found under which the cysteine residues/disulfide bridges in the core region can be reduced and subsequently form a disulfide bridge with core hinge cysteines in another half-molecule, while keeping other disulfide bridges in the antibody and the general antibody structure intact. For example, an IgG4-like core hinge region may be an IgG4 core hinge region or a core hinge sequence of an antibody of another isotype in which one of the prolines of the CPPC sequence (SEQ ID NO: 28) in the core region has been mutated, e.g. to a serine, such as a mutation of CPPC (SEQ ID NO: 28) to CPSC (SEQ ID NO: 27).

The term "IgG4-like CH3 region" in the context of the present application refers to a CH3 region which is identical to the CH3 of IgG4, e.g. human IgG4, or a CH3 region which is functionally equivalent to a IgG4 CH3 region. Functionally equivalent, in this context, means that the CH3 region, similar to the CH3 region of IgG4, does not form stable inter-half-molecule interactions. The formation of stable inter-half-molecules by a given CH3 region can e.g. be tested by replacing the CH3 of an IgG4 with that CH3 region and test for exchange under the conditions given in Examples 31 or 32. If exchange is observed, then no stable inter-half-molecule interactions are formed. For example, an IgG4-like CH3 region may be a CH3 region which is equally efficient in allowing half-molecule exchange as a CH3 region from IgG4. Accordingly, an IgG4-like CH3 region may be structurally similar to the CH3 region of IgG4, e.g. more than 75%, such as more than 90% identical to the sequence of the CH3 region of IgG4. However, an IgG4-like CH3 region in the present context may in addition or alternatively be a CH3 region which structurally is not close to the CH3 region of IgG4, but has similar functional characteristics in that it does not comprise any amino acid residues which participate in the formation of disulfide bonds or covalent or stable non-covalent inter-heavy chain bonds, such as salt bridges, with other peptides comprising an identical amino acid sequence of the CH3 region. For example, an IgG4-like CH3 region can be a mutated IgG1 CH3 region in which one or more amino acid residues that are involved in inter-half-molecule CH3-CH3 interactions have been changed or deleted.

The term "reducing conditions" or "reducing environment" refers to a condition or an environment in which a substrate, here a cysteine residue in the core-region of an antibody, is more likely to become reduced than oxidized.

The term "reducing agent" refers to a compound which reduces molecules in its environment, i.e., which changes molecules in its environment to become more reduced and more reducing. A reducing agent acts by donating electrons, thereby becoming itself oxidized after having reduced a substrate. Thus, a reducing agent is an agent which donates electrons. Examples of reducing agents include dithiothreitol (DTT), mercaptoethanol, cysteine, thioglycolate, cysteamine, glutathione, and sodium borohydride. In one embodiment, the reducing agent does not comprise an enzyme.

"Disulfide bond formation" refers to the process of forming a covalent bond between two cysteines present in one or two polypeptides, which is schematized as "—S—S—".

"Disulfide bond reduction" refers to the process of cleaving a disulfide bond, thereby resulting in two thiol groups (—SH groups).

The term "disulfide bond isomerization" refers to an exchange of disulfide bonds between different cysteines, i.e., the shuffling of disulfide bonds.

"Protein disulfide bond isomerases" refer to proteins which catalyze the isomerization of disulfide bonds in proteins.

"No significant reduction" when used in the context of reduction of disulfide bridges means that generally less than 10%, such as less than 5%, e.g. less than 2% or less than 1% of the specified disulfide bridges in the solution undergo reduction.

Aspects and Embodiments of the Invention

As described above, in a first main aspect, the invention relates to an ex vivo method for the generation of a bispecific antibody, said method comprising the steps of:

a) providing a first antibody having a first binding specificity, wherein said first antibody comprises an IgG4-like CH3 region, b) providing a second antibody having a second binding specificity which differs from said first binding specificity, wherein said second antibody comprises an IgG4-like CH3 region, c) incubating said first and second antibodies together under reducing conditions which allow the cysteines in the core hinge region to undergo disulfide-bond isomerization, and d) obtaining a bispecific antibody.

In a preferred embodiment, the first and second antibodies used in the methods of the invention are monoclonal antibodies. Monoclonal antibodies may e.g. be produced by the hybridoma method first described by Kohler et al. (14), or may be produced by recombinant DNA methods. Monoclonal antibodies may also be isolated from phage antibody libraries using the techniques described in, for example, Clackson et al. (15) and Marks et al. (16). Monoclonal antibodies may be obtained from any suitable source. Thus, for example, monoclonal antibodies may be obtained from hybridomas prepared from murine splenic B cells obtained from mice immunized with an antigen of interest, for instance in form of cells expressing the antigen on the surface, or a nucleic acid encoding an antigen of interest. Monoclonal antibodies may also be obtained from hybridomas derived from antibody-expressing cells of immunized humans or non-human mammals such as rats, dogs, primates, etc.

In one embodiment, the antibody of the invention is a human antibody. Human monoclonal antibodies directed may be generated using transgenic or transchromosomal mice carrying parts of the human immune system rather than the mouse system. Such transgenic and transchromosomic mice include mice referred to herein as HuMAb mice and KM mice, respectively, and are collectively referred to herein as "transgenic mice".

The HuMAb mouse contains a human immunoglobulin gene miniloci that encodes unrearranged human heavy (μ and γ) and κ light chain immunoglobulin sequences, together with targeted mutations that inactivate the endogenous μ and κ chain loci (17). Accordingly, the mice exhibit reduced expression of mouse IgM or κ and in response to immunization, the introduced human heavy and light chain transgenes, undergo class switching and somatic mutation to generate high affinity human IgG,κ monoclonal antibodies (17-20). The preparation of HuMAb mice is described in detail in ref. 21-25. See also U.S. Pat. Nos. 5,545,806, 5,569,825, 5,625,126, 5,633,425, 5,789,650, 5,877,397, 5,661,016, 5,814,318, 5,874,299, 5,770,429, 5,545,807, WO 98/24884, WO 94/25585, WO 93/1227, WO 92/22645, WO 92/03918 and WO 01/09187.

The HCo7 mice have a JKD disruption in their endogenous light chain (kappa) genes (as described in Chen et al. (26)), a CMD disruption in their endogenous heavy chain genes (as described in Example 1 of WO 01/14424), a KCo5 human kappa light chain transgene (as described in Fishwild et al. (25)), and a HCo7 human heavy chain transgene (as described in U.S. Pat. No. 5,770,429).

The HCo12 mice have a JKD disruption in their endogenous light chain (kappa) genes (as described in Chen et al. (26)), a CMD disruption in their endogenous heavy chain genes (as described in Example 1 of WO 01/14424), a KCo5 human kappa light chain transgene (as described in Fishwild et al. (25)), and a HCo12 human heavy chain transgene (as described in Example 2 of WO 01/14424).

In the KM mouse strain, the endogenous mouse kappa light chain gene has been homozygously disrupted as described in Chen et al. (26) and the endogenous mouse heavy chain gene has been homozygously disrupted as described in Example 1 of WO 01/09187. This mouse strain carries a human kappa light chain transgene, KCo5, as described in Fishwild et al. (25). This mouse strain also carries a human heavy chain transchromosome composed of chromosome 14 fragment hCF (SC20) as described in WO 02/43478.

Splenocytes from these transgenic mice may be used to generate hybridomas that secrete human monoclonal antibodies according to well known techniques. Such transgenic non-human animals, non-human animals comprising an operable nucleic acid sequence coding for expression of antibody used in the invention, non-human animals stably transfected with one or more target-encoding nucleic acid sequences, and the like, are additional features of the present invention.

Human monoclonal or polyclonal antibodies to be used in the present invention, or antibodies used in the present invention originating from other species may also be generated transgenically through the generation of another non-human mammal or plant that is transgenic for the immunoglobulin heavy and light chain sequences of interest and production of the antibody in a recoverable form therefrom. In connection with the transgenic production in mammals, antibodies may be produced in, and recovered from, the milk of goats, cows, or other mammals. See for instance U.S. Pat. Nos. 5,827,690, 5,756,687, 5,750,172 and 5,741,957.

Further, human or other antibodies to be used in the present invention may be generated through display-type technologies, including, without limitation, phage display, retroviral display, ribosomal display, and other techniques, using techniques well known in the art and the resulting molecules may be subjected to additional maturation, such as affinity maturation, as such techniques are well known in the art (see for instance ref. 27, 28 and 30 (phage display), 29 (ribosomal display), 31-35 and U.S. Pat. No. 5,733,743). If display technologies are utilized to produce antibodies that are not human, such antibodies may be humanized.

As explained above, in some embodiments, the first and/or second antibody used in the method of the invention is an IgG4 antibody. However, the antibody used in the invention may in principle be of any isotype, provided that the sequences in the CH3 region allow half-molecule exchange. For example, the antibodies used or obtained in the method of the invention may comprise any of the constant region sequences shown in SEQ ID NO:19-22 (outside any specified mutated positions).

Thus, in one embodiment of the method of the invention, the first and/or second antibody comprises a CPPC sequence (SEQ ID NO: 28) in the core hinge region. In another embodiment, the first and/or second antibody comprises an IgG4-like core hinge region. For example, in some embodiments, said first and/or second antibody is an antibody which comprises a $CX_1X_2C$ sequence in the core hinge region, wherein $X_1$ and $X_2$ can be any amino acid, provided that $X_1$ and $X_2$ are not both proline. In another embodiment, said first and/or second antibody is an antibody which comprises a $CX_3PC$ or $CPX_3C$ sequence in the core hinge region, wherein $X_3$ can be any amino acid except for proline. In a further embodiment, said first and/or second antibody is an antibody which comprises a CSPC (SEQ ID NO: 30), CPSC (SEQ ID NO: 27), CRPC (SEQ ID NO: 31), CPRC (SEQ ID NO: 32), CGHC (SEQ ID NO: 33) or CPHC (SEQ ID NO: 34) sequence in the core hinge region. The above-described mutations may for example be introduced by site-directed mutagenesis well known in the art.

The choice of isotype typically will be guided by the desired effector functions, such as CDC induction, or activity in ADCC. Exemplary isotypes are IgG1, IgG2, IgG3, and IgG4 (see e.g. SEQ ID NO:19-22). Either of the human light chain constant regions, kappa or lambda, may be used. If desired, the class of an antibody for use in the present invention may be switched by known methods. For example, an antibody to be used in the present invention that was originally IgM, IgG1 or IgG2 may be class switched to an IgG4 antibody of the present invention. Thus, the effector function of the antibodies of the present invention may be changed by isotype switching to, e.g., an IgG1, IgG2, IgG3, IgG4, IgD, IgA, IgE, or IgM antibody for various therapeutic uses.

In one embodiment, the first and/or second antibody used in the invention is a full-length antibody. In another embodiment, the first and/or second antibody of the invention used is an antibody fragment.

In one embodiment of the method of the invention, the first and/or second antibody comprises an IgG4 CH3 region, such as the IgG4 CH3 region having the sequence shown in FIG. 18 (SEQ ID NO:22).

However, in another embodiments of the method of the invention, the first and/or second antibody comprises a CH3 region of a non-IgG4 isotype, wherein the CH3 sequence is such, or has been modified such, that it does not comprise any amino acid residues which participate in the formation of disulfide bonds or covalent or stable non-covalent inter-heavy chain bonds with other peptides comprising an identical amino acid sequence of the CH3 region.

For example, in one further embodiment hereof, the first and/or second antibody comprises a CH3 region having the sequence as shown in FIG. 18 (SEQ ID NO: 19), wherein the CH3 region has been modified so that one or more of the following amino acid substitutions have been made: Arg (R) in position 238 has been replaced by Gln (Q); Asp (D) in position 239 has been replaced by Glu (E); Lys (K) in position 292 has been replaced by Arg (R); Gln (Q) in position 302 has been replaced by Glu (E); and Pro (P) in position 328 has been replaced by Leu (L).

In a preferred embodiment, the first and/or second antibody comprises a CH3 region having the sequence as shown in FIG. 18 (SEQ ID NO: 19), wherein Lys (K) in position 292 has been replaced by Arg (R).

In another embodiment, the first and/or second antibody comprises a CH3 region having the sequence as shown in FIG. 18 (SEQ ID NO: 19), but wherein the Lys (K) in position 292 has been replaced by Tyr (W) or Phe (F).

In another further embodiment, the first and/or second antibody comprises a CH3 region having the sequence as shown in FIG. 18 (SEQ ID NO: 20), wherein the CH3 region has been modified so that one or more, or all five of the of the following amino acid substitutions have been made: Arg (R) in position 234 has been replaced by Gln (Q); Met (M) in position 276 has been replaced by Val (V); Lys (K) in position 288 has been replaced by Arg (R); Gln (Q) in position 298 has been replaced by Glu (E); and Pro (P) in position 324 has been replaced by Leu (L).

In a preferred embodiment, the first and/or second antibody comprises a CH3 region having the sequence as shown in FIG. 18 (SEQ ID NO: 20), wherein Arg (R) in position 234 has been replaced by Gln (Q).

In a further preferred embodiment, the first and/or second antibody comprises a CH3 region having the sequence as shown in FIG. 18 (SEQ ID NO: 20), wherein Arg (R) in position 234 has been replaced by Gln (Q); and Pro (P) in position 324 has been replaced by Leu (L).

In another further embodiment, the first and/or second antibody comprises a CH3 region having the sequence as shown in FIG. 18 (SEQ ID NO: 21), wherein the CH3 region has been modified so that one or more or all 10 of the of the following amino acid substitutions have been made: Arg (R) in position 285 has been replaced by Gln (Q); Ser (S) in position 314 has been replaced by Asn (N); Asn (N) in position 322 has been replaced by Lys (K); Met (M) in position 327 has been replaced by Val (V); Lys (K) in position 339 has been replaced by Arg (R); Gln (Q) in position 349 has been replaced by Glu (E); Ile (I) in position 352 has been replaced by Val (V); Arg (R) in position 365 has been replaced by His (H); Phe (F) in position 366 has been replaced by Tyr (Y); and Pro (P) in position 375 has been replaced by Leu (L).

In a preferred embodiment, the first and/or second antibody comprises a CH3 region having the sequence as shown in FIG. 18 (SEQ ID NO: 21), wherein Arg (R) in position 285 has been replaced by Gln (Q).

In a preferred embodiment, the first and/or second antibody comprises a CH3 region having the sequence as shown in FIG. 18 (SEQ ID NO: 21), wherein Arg (R) in position 285 has been replaced by Gln (Q); and Pro (P) in position 375 has been replaced by Leu (L).

In a further embodiment of the method of the invention, said first antibody comprises a CPPC (SEQ ID NO: 28) in the core hinge region and comprises an IgG4-like CH3 region and wherein said second antibody comprises a CPPC (SEQ ID NO: 28) in the core hinge region and comprises an IgG4-like CH3 region.

As explained above, in a main aspect, the invention relates to an ex vivo method for the generation of a bispecific antibody, said method comprising the steps of:

a) providing a first antibody having a first binding specificity, wherein said first antibody comprises an IgG4-like CH3 region, b) providing a second antibody having a second binding specificity which differs from said first binding specificity, wherein said second antibody comprises an IgG4-like CH3 region, c) incubating said first and second antibodies together under reducing conditions which allow the cysteines in the core hinge region to undergo disulfide-bond isomerization, and d) obtaining a bispecific antibody.

In one embodiment of the method of the invention, the conditions in step c) are chosen such that no significant reduction or isomerization of disulfide bridges outside the core hinge region occurs.

In another embodiment, the reducing conditions in step c) are conditions that stimulate the intrinsic activity of the core hinge region to perform disulfide bond exchange.

In a further embodiment of the invention, step c) comprises the addition of a reducing agent. In a further embodiment, step c) comprises the addition of an agent selected from the group consisting of: glutathione, L-cysteine, dithiothreitol, beta-mercapto-ethanol and cysteamine.

In one embodiment of the method of the invention, the concentration of said reducing agent is such that the redox potential of the solution generated in step c) is equal to, or more reducing than, the redox potential generated by 1 microM of glutathione under the conditions described in Example 31, such as equal to, or more reducing than, the redox potential generated by 10 microM of glutathione, e.g. equal to, or more reducing than, the redox potential generated by 50 microM of glutathione, such as equal to, or more reducing than, the redox potential generated by 0.1 mM of glutathione, under the conditions described in Example 31.

In a further embodiment, the concentration of said reducing agent is such that the redox potential of the solution generated in step c) is equal to, or more reducing than, the redox potential generated by 1 microM of glutathione under the conditions described in Example 31, such as equal to, or more reducing than, the redox potential generated by 10 microM of glutathione, e.g. equal to, or more reducing than, the redox potential generated by 50 microM of glutathione, such as equal to, or more reducing than, the redox potential generated by 0.1 mM of glutathione, under the conditions described in Example 31, and is equal to, or less reducing than, the redox potential generated by 1 M of glutathione under the conditions described in Example 31, such as equal to, or less reducing than, the redox potential generated by 100 mM of glutathione equal to, or less reducing than, the redox potential generated by 15 mM of glutathione.

In an embodiment, wherein the first antibody has a CPPC sequence (SEQ ID NO: 28) in the core hinge region and/or the second antibody has a CPPC sequence (SEQ ID NO: 28) in the core hinge region, it is preferred that the redox potential of the solution generated in step c) is equal to, or more reducing than, the redox potential generated by 1 mM of glutathione, e.g. equal to, or more reducing than, the redox potential generated by 2 mM of glutathione, such as equal to, or more reducing than, the redox potential generated by 4 mM of glutathione, e.g. equal to, or more reducing than, the redox potential generated by 6 mM of glutathione, such as equal to, or more reducing than, the redox potential generated by 8 mM of glutathione, e.g. equal to, or more reducing than, the redox potential generated by 10 mM of glutathione, under the conditions described in Example 35.

In a further embodiment, the concentration of said reducing agent is such that the redox potential of the solution generated in step c) is equal to, or more reducing than, the redox potential generated by 1 mM of glutathione, e.g. equal to, or more reducing than, the redox potential generated by 2 mM of glutathione, such as equal to, or more reducing than, the redox potential generated by 4 mM of glutathione, e.g. equal to, or more reducing than, the redox potential generated by 6 mM of glutathione, such as equal to, or more reducing than, the redox potential generated by 8 mM of glutathione, e.g. equal to, or more reducing than, the redox potential generated by 10 mM of glutathione, under the conditions described in Example 35, and equal to, or less reducing than, the redox potential generated by 1 M of glutathione, such as equal to, or less reducing than, the redox potential generated by 100 mM of glutathione equal to, or less reducing than, the redox potential generated by 15 mM of glutathione.

In one embodiment of the method of the invention, step c) comprises the incubation of said antibodies in the presence of reduced glutathione for at least 1 hours, such as for at least 2 hours, e.g. for at least 5 hours, such as at least 10 hours at a temperature of 20° C. or more, such as 37° C.

In a further embodiment of the method of the invention, the conditions chosen in step c) are such that fewer than 10%, such as fewer than 5%, e.g. fewer than 2%, such as fewer than 1% of the antibody molecules in the resulting composition are in an aggregated state, as determined by size-exclusion chromatography as described herein (wherein a peak eluting earlier than the antibodies of the starting material is indicative of the formation of aggregates).

In one embodiment of the ex vivo method of the invention, the method comprises the addition of a protein having protein disulfide isomerase activity, such as PDI. In another embodiment of the ex vivo method of the invention, the method does not comprise the addition of a protein having protein disulfide isomerase activity, such as PDI.

In one embodiment of the ex vivo method of the invention, the method does not comprise the addition of living cells or cell extracts.

As explained above, the first and second antibody used in the method of the invention differ in binding specificity, i.e. bind different epitopes. In principle, any combination of specificities can be used as starting material in the method of the invention. The method of invention is also not limited to having only two different antibodies as starting material. Thus, the method of the invention may also be performed with three or more antibodies as starting material. In such an embodiment, the composition obtained in step d) of the method of invention will contain a plurality of bispecific antibodies.

In one embodiment of the method of the invention, the first antibody has binding specificity for a tumor cell or tumor cell protein, such as erbB1, erbB2, erbB3, erbB4, MUC-1, CD19, CD20, CD4, CD38 or CXCR5 or for the signaling components of the B cell receptor, CD79a or CD79b. In another embodiment, the first antibody has binding specificity for a tumor cell or tumor cell protein, such as erbB1, erbB2, erbB3, erbB4, MUC-1, CD19, CD20, CD4 or CXCR5, and the second antibody has binding specificity for a tumor cell protein, such as erbB1, erbB2, erbB3, erbB4, MUC-1, CD19, CD20, CD4 or CXCR5.

In a further embodiment, the first antibody has a binding specificity for erbB1 and the second antibody has a binding specificity for erbB2.

In another embodiment, the first antibody has a binding specificity for CD19 and the second antibody has a binding specificity for CD20.

In a further embodiment, the first antibody has a binding specificity for CD38 and the second antibody has a binding specificity for CD34.

In an even further embodiment, the first antibody has a binding specificity for CD4 and the second antibody has a binding specificity for CXCR5.

In another embodiment of the method of the invention, the first antibody has a binding specificity for a pathogenic microorganism. In a further embodiment, the first antibody has a binding specificity for a pathogenic microorganism and the second antibody has binding specificity for an effector cell protein, such as CD3, CD25, CD28, CD16, CD89, CD32 or CD1.

A bispecific antibody can also be used to target a chemotherapeutic agent more specifically to the cells on which the agent should act. Thus, in a further embodiment of the method of the invention, the first antibody has binding specificity for a tumor cell or tumor cell protein, such as erbB1, erbB2, erbB3, erbB4, MUC-1, CD19, CD20, CD4 or CXCR5 and the second antibody has a binding specificity for a chemotherapeutic agent.

Furthermore, serum half-life of an antibody may be altered by including in a bispecific antibody a binding specificity for a serum protein. For instance, serum half-life may be prolonged by including in a bispecific antibody, a binding specificity for serum albumin. Thus, in a further embodiment of the method of the invention, the first antibody has binding specificity for a tumor cell or tumor cell protein, such as erbB1, erbB2, erbB3, erbB4, MUC-1, CD19, CD20, CD4 or CXCR5 and the second antibody has a binding specificity for a blood protein, such as serum albumin A second binding specificity can also be used to target an antibody to a specific tissue, such as brain or liver. Thus, in a further embodiment of the method of the invention, the first antibody has binding specificity for a tumor cell or tumor cell protein, such as erbB1, erbB2, erbB3, erbB4, MUC-1, CD19, CD20, CD4 or CXCR5 and the second antibody has a binding specificity for a brain protein, such as transferrin or a liver protein.

Moreover, a second binding specificity can be used to target blood clotting factors to a particular desired site of action. For example, a bispecific antibody having a first binding specificity for a tumor cell and a second binding specificity for a blood clotting factor could direct blood clotting to a tumor, and thus stop tumor growth. Thus, in a further embodiment of the method of the invention, the first antibody has binding specificity for a tumor cell or tumor cell protein, such as erbB1, erbB2, erbB3, erbB4, MUC-1, CD19, CD20, CD4 or CXCR5 and the second antibody has a binding specificity for a protein involved in blood clotting, such as tissue factor.

In further embodiments of the invention, the first and/or second antibody is linked to a compound selected from the group consisting of: a cytotoxic agent; a radioisotope; a prodrug or drug, such as a taxane; a cytokine; a chemokine and complement, such as C1q. Such compound may make killing of target cells more effective, e.g. in cancer therapy. The compound may alternatively be coupled to the resulting bispecific antibody, i.e. after the half-molecule exchange has taken place.

In a further embodiment of the method of the invention, the method comprises a further step of bringing the composition obtained in step c) to non-reducing or less-reducing conditions, in order to stop further half-molecule exchange. This can be done by various methods known in the art, e.g. dialysis of resulting composition or size-based chromatography to remove a small molecule reducing agent.

In an even further embodiment of the method of the invention, the resulting bispecific antibodies are stabilized by performing a chemical cross-linking of the two half-molecules, thus preventing any further exchange, even when the bispecific antibody is subsequently used under conditions, such as in vivo conditions, where the antibody could otherwise undergo half-molecule exchange. Thus, in one embodiment, the method of the invention comprises the further step of:

a) chemically cross-linking the cysteines in the hinge region, e.g. using compounds containing maleimide, such as bis-maleimidohexane, b) chemically cross-linking of the carbohydrate side-chains on the half-molecules, e.g. via periodate oxidation followed by a reaction of the aldehyde groups with suitable cross-linkers, such as adipine dihydrazide, or c) cross-linking of asymmetrically introduced cysteines in the CH3 region, e.g. as described in Merchant et al. (36) (incorporated herein by reference), for example using one or more of the following combinations (reference to SEQ ID NO:19):

D282C in the first antibody with K275C in the second antibody,

D282S in the first antibody with K275S in the second antibody,

Y232C in the first antibody with S237C in the second antibody,

Y232C in the first antibody with D239C in the second antibody,

Y232C in the first antibody with E240C in the second antibody,

L234C in the first antibody with S237C in the second antibody,

T277C in the first antibody with V280C in the second antibody,

V280C in the first antibody with K275C in the second antibody.

In a further aspect, the invention relates to stabilized bispecific antibodies obtained or obtainable by cross-linking methods, e.g. by any of the three cross-linking methods described above.

Regardless of whether or not the resulting bispecific antibody has been stabilized by cross-linking, the method of the invention may, in some embodiments, comprise a further step of purifying the bispecific antibody. Mixtures containing bispecific antibodies can be purified using standard chromatography techniques, such as (but not limited to) standard Protein A chromatography, Protein G, Protein L, cationic/anionic exchange chromatography, size exclusion chromatography, hydrophobic interaction chromatography, thiophilic chromatography or using ligands designed to capture IgG molecules (Protein A mimetics, Llama $V_{HH}$ ligands and the like). Alternatively, the IgG mixtures can be precipitated using standard techniques such as salt-induced precipitation (ammonium sulphate), addition of organic solvents (DMSO, ethanol), changing pH or non-ionic polymers (Polyethylene Glycol). In another setting, mixtures can be applied to filtration techniques using membranes allowing concentration of the IgG molecules. Combinations of all these techniques may be required to purify a bispecific antibody to full homogeneity as certain mixtures may still contain the parent IgG molecules next to the bispecific antibody. Additional purification steps may then be required to separate the bispecific antibody from the parent monospecific IgG molecules. This could e.g. be done by purification by binding and elution using an affinity column for the first binding specificity followed by binding and elution using an affinity column for the second binding specificity. In a preferred embodiment, in particular when no chemical cross-linking has been performed, the purification is done under conditions that prevent further half-molecule exchange, such as non-reducing conditions.

The quantity, quality and purity of (purified) bispecific antibodies can be analyzed using routine biochemical techniques such as absorbance measurements, HP-SEC, SDS-PAGE, native PAGE and RP-HPLC. Of particular interest are techniques that can discriminate bispecific antibodies from the parent IgG molecules. Examples of such techniques are (but not limited to) IEF, cIEF, CIEX and Mass spectrometry (ESI, MALDI), allowing highly accurate separation and detection of the molecules on the basis of charge and/or mass. Dual binding specificity of the bispecific antibody can be assessed using a variety of different binding assay formats using for instance ELISA, RIA, Surface plasma resonance (SPR), Bio-layer Interferometry, DELFIA, FRET, ECL, Gyros and AlfaScreen.

In one embodiment, half molecule exchange may be performed under conditions that favour formation of bispecific antibodies directed against one of the two antigens of interest. For example, consider antibodies against antigens X and Y. If exchange is performed using an excess of antibody against antigen X, such as a 5 fold excess or 10 fold excess, most or all antibodies against antibody Y will become bispecific (i.e. recognizing antigens X and Y).

This procedure may be followed by purification of bispecific antibodies on matrix-immobilized antigen Y and affinity column chromatography. The bound antibodies are highly enriched for the desired bispecific antibody. The unbound antibodies against antigen X may be used to repeat the cycle above.

In case stabilization to prevent exchange in vivo is required, the bispecific antibodies can be cross-linked as described above. Following chemical cross-linking, non-stabilized antibodies can be purified from stabilized antibody by performing an additional exchange reaction with an excess of antibody against antigen Z followed by absorption of anti-Z containing antibody against matrix-immobilized antigen Z (such as by affinity columns chromatography). The non-bound fraction then contains the desired stabilized bispecific antibody.

In an even further embodiment of the method of the invention, the method comprises the further step of formulating the resulting bispecific antibodies for therapeutic use. This comprises the formulation of a therapeutically effective amount of the bispecific antibody in an aqueous solution that is suitable for human use, in particular suitable for parenteral, such as intravenous administration.

In a further aspect, the invention relates to an ex vivo method for the generation of a bispecific antibody, said method comprising the steps of:

a) providing a first antibody having a first binding specificity, wherein said first antibody comprises a CPPC sequence (SEQ ID NO: 28) in the core hinge region and an IgG4 CH3 region, b) providing a second antibody having a second binding specificity which differs from said first binding specificity, wherein said second antibody comprises a CPPC sequence (SEQ ID NO: 28) in the core hinge region and an IgG4 CH3 region, and c) incubating said first and second antibodies together under reducing conditions which allow the cysteines in the core hinge region to undergo disulfide-bond isomerization, and d) obtaining a bispecific antibody.

Preferably, in step c) a reducing agent has been added wherein the concentration of said agent is such that the redox potential of the solution generated in step c) is equal to, or more reducing than, the redox potential generated by 1 mM of glutathione, e.g. equal to, or more reducing than, the redox potential generated by 2 mM of glutathione, such as equal to, or more reducing than, the redox potential generated by 4 mM of glutathione, e.g. equal to, or more reducing than, the redox potential generated by 6 mM of glutathione, such as equal to, or more reducing than, the redox potential generated by 8 mM of glutathione, e.g. equal to, or more reducing than, the redox potential generated by 10 mM of glutathione, under the conditions described in Example 35.

In a further aspect, the invention relates to a composition comprising bispecific antibodies obtained or obtainable by any of the method of the invention as described herein.

In a further main aspect, the invention relates to an isolated bispecific antibody comprising two IgG4-like CH3 regions.

In one embodiment, said antibody comprises one or two CPPC sequences (SEQ ID NO: 28) in the core hinge region.

In another embodiment, said antibody comprises one or two $CX_1X_2C$ sequences in the core hinge region, wherein $X_1$ and $X_2$ can be any amino acid, provided that $X_1$ and $X_2$ are not both proline.

In a further embodiment, said the antibody comprises one or two $CX_3PC$ or $CPX_3C$ sequences in the core hinge region, wherein $X_3$ can be any amino acid except for proline.

In an even further embodiment, said antibody comprises one or two CSPC (SEQ ID NO: 30), CPSC (SEQ ID NO: 29), CRPC (SEQ ID NO: 31) or CPRC (SEQ ID NO: 32) sequences in the core hinge region.

In some embodiments of the isolated bispecific antibody, the first and/or the second CH3 region is of a non-IgG4 isotype, wherein the CH3 sequence is such, or has been modified such, that it does not comprise any amino acid residues which participate in the formation of disulfide bonds or covalent or stable non-covalent inter-heavy chain bonds with other peptides comprising an identical amino acid sequence of the CH3 region.

In one further embodiment thereof, the first and/or the second CH3 region has the sequence as shown in FIG. 18 (SEQ ID NO: 19), wherein the CH3 region has been modified so that one or more of the following amino acid substitutions have been made: Arg (R) in position 238 has been replaced by Gln (Q); Asp (D) in position 239 has been replaced by Glu (E); Lys (K) in position 292 has been replaced by Arg (R); Gln (Q) in position 302 has been replaced by Glu (E); and Pro (P) in position 328 has been replaced by Leu (L).

In another further embodiment, said first and/or the second CH3 region has the sequence as shown in FIG. 18 (SEQ ID NO: 20), wherein the CH3 region has been modified so that one or more of the of the following amino acid substitutions have been made: Arg (R) in position 234 has been replaced by Gln (Q); Met (M) in position 276 has been replaced by Val (V); Lys (K) in position 288 has been replaced by Arg (R); Gln (Q) in position 298 has been replaced by Glu (E); and Pro (P) in position 324 has been replaced by Leu (L).

In a yet further embodiment, said first and/or the second CH3 region has the sequence as shown in FIG. 18 (SEQ ID NO: 21), wherein the CH3 region has been modified so that one or more of the of the following amino acid substitutions have been made: Arg (R) in position 285 has been replaced by Gln (Q); Ser (5) in position 314 has been replaced by Asn (N); Asn (N) in position 322 has been replaced by Lys (K); Met (M) in position 327 has been replaced by Val (V); Lys (K) in position 339 has been replaced by Arg (R); Gln (Q) in position 349 has been replaced by Glu (E); Ile (I) in position 352 has been replaced by Val (V); Arg (R) in position 365 has been replaced by H is (H); Phe (F) in position 366 has been replaced by Tyr (Y); and Pro (P) in position 375 has been replaced by Leu (L).

In an even further embodiment, the first and/or the second CH3 region of the antibody of the invention is an IgG4 CH3 region.

In an even further aspect, invention relates to a composition, such as a pharmaceutical composition comprising bispecific antibodies of the invention or bispecific antibodies obtained or obtainable by any of the method of the invention as described herein for use as a medicament, such as for use as a medicament for the treatment of cancer or infectious diseases.

In an even further aspect, invention relates to the use of a composition comprising bispecific antibodies of the invention or bispecific antibodies obtained or obtainable by any of the method of the invention for the preparation of a medicament for the treatment of cancer or infectious diseases.

The method of the invention can also be used to select particularly interesting or effective combinations of target binding specificities. For instance, using the method of the invention, a set or "matrix" of different bispecific antibodies can be made from a set of antibodies having different binding specificities. The resulting bispecific antibody set or matrix can then be tested for a desired biological property to select the best combination.

Thus, in a yet further aspect, the invention relates to a method for the selection of a bispecific antibody having a desired property, said method comprising the steps of:
 a) providing a set of antibodies, wherein each antibody has a different target specificity and wherein each antibody comprises an IgG4-like CH3 region,
 b) incubating each antibody of said set of antibodies with another antibody of said set under reducing conditions, thus generating a set of antibody mixtures, wherein each mixture contains a different bispecific antibody,
 c) assaying the resulting set of antibody mixtures for a given desired property, and
 d) selecting a bispecific antibody mixture having the desired property.

Step b) in the method above can be performed as previously described above for step c).

In one embodiment, the desired property to be tested is tumor cell killing.

References
1. Aalberse, R. C., R. van der Gaag, and J. van Leeuwen. 1983. Serologic aspects of IgG4 antibodies. I. Prolonged immunization results in an IgG4-restricted response. *J Immunol* 130:722.
2. van der Zee, J. S., P. van Swieten, and R. C. Aalberse. 1986. Serologic aspects of IgG4 antibodies. II. IgG4 antibodies form small, nonprecipitating immune complexes due to functional monovalency. *J Immunol* 137:3566.
3. Schuurman, J., R. Van Ree, G. J. Perdok, H. R. Van Doorn, K. Y. Tan, and R. C. Aalberse. 1999. Normal human immunoglobulin G4 is bispecific: it has two different antigen-combining sites. *Immunology* 97:693.
4. Aalberse, R. C., and J. Schuurman. 2002. IgG4 breaking the rules. *Immunology* 105:9.
5. Aalberse, R. C., J. Schuurman, and R. van Ree. 1999. The apparent monovalency of human IgG4 is due to bispecificity. *Int Arch Allergy Immunol* 118:187.
6. Schuurman, J., G. J. Perdok, A. D. Goiter, and R. C. Aalberse. 2001. The inter-heavy chain disulfide bonds of IgG4 are in equilibrium with intra-chain disulfide bonds. *Mol Immunol* 38:1.
7. Bloom, J. W., M. S. Madanat, D. Marriott, T. Wong, and S. Y. Chan. 1997. Intrachain disulfide bond in the core hinge region of human IgG4. *Protein Sci* 6:407.
8. Gregory, L., K. G. Davis, B. Sheth, J. Boyd, R. Jefferis, C. Nave, and D. R. Burton. 1987. The solution conformations of the subclasses of human IgG deduced from sedimentation and small angle X-ray scattering studies. *Mol Immunol* 24:821.
9. Deng, L., D. Wylie, Y. S. Tsao, B. Larkin, M. Voloch, and W. L. Ling. 2004. Detection and quantification of the human IgG4 half-molecule, HL, from unpurified cell-culture supernatants. *Biotechnol Appl Biochem* 40:261.
10. Marcin and Zhu (2005) Acta Pharmacol Sin. 26:649
11. Fundamental Immunology Ch. 7 (Paul, W., ed., 2nd ed. Raven Press, N.Y. (1989))
12. Chothia and Lesk J. Mol. Biol. 196, 901-917 (1987)
13. Kabat et al., Sequences of Proteins of Immunological Interest, 5th Ed. Public Health Service, National Institutes of Health, Bethesda, Md. (1991)
14. Kohler et al., Nature 256, 495 (1975)
15. Clackson et al., Nature 352, 624-628 (1991)
16. Marks et al., J. Mol. Biol. 222, 581-597 (1991)
17. Lonberg, N. et al., Nature 368, 856-859 (1994)
18. Lonberg, N. Handbook of Experimental Pharmacology 113, 49-101 (1994)
19. Lonberg, N. and Huszar, D., Intern. Rev. Immunol. Vol. 13 65-93 (1995)
20. Harding, F. and Lonberg, N. Ann. N.Y. Acad. Sci. 764 536-546 (1995)).
21. Taylor, L. et al., Nucleic Acids Research 20, 6287-6295 (1992)
22. Chen, J. et al., International Immunology 5, 647-656 (1993)
23. Tuaillon et al., J. Immunol. 152, 2912-2920 (1994)
24. Taylor, L. et al., International Immunology 6, 579-591 (1994)
25. Fishwild, D. et al., Nature Biotechnology 14, 845-851 (1996)
26. Chen et al., EMBO J. 12, 821-830 (1993)
27. Hoogenboom et al., J. Mol. Biol. 227, 381 (1991)
28. Vaughan et al., Nature Biotech 14, 309 (1996)
29. Hanes and Plucthau, PNAS USA 94, 4937-4942 (1997)
30. Parmley and Smith, Gene 73, 305-318 (1988)
31. Scott TIBS 17, 241-245 (1992)
32. Cwirla et al., PNAS USA 87, 6378-6382 (1990)
33. Russel et al., Nucl. Acids Research 21, 1081-1085 (1993),
34. Hoogenboom et al., Immunol. Reviews 130, 43-68 (1992)
35. Chiswell and McCafferty TIBTECH 10, 80-84 (1992)
36. Merchant et al. (1998) Nature Biotech 16:677-681
37. Sambrook, Russell et al. 2000 Molecular cloning. A laboratory manual (third edition), Cold Spring Harbor Laboratory Press
38. Akkerdaas, van Ree et al. 1995 Allergy 50(3), 215-220
39. de Groot et al. 1988 J. Allergy Clin. Immunol. 82, 778

The present invention is further illustrated by the following examples which should not be construed as further limiting.

EXAMPLES

Example 1

Oligonucleotide Primers and PCR Amplification

Oligonucleotide primers were synthesized and quantified by Isogen Bioscience (Maarssen, The Netherlands). Primers were dissolved in $H_2O$ to 100 µmol/µl and stored at −20° C. A summary of all PCR and sequencing primers is given below. For PCR, PfuTurbo® Hotstart DNA polymerase (Stratagene, Amsterdam, The Netherlands) was used according to the manufacturer's instructions. Each reaction mix contained 200 µM mixed dNTPs (Roche Diagnostics, Almere, The Netherlands), 6.7 µmol of both the forward and reverse primer, 100 ng of genomic DNA or 1 ng of plasmid DNA and 1 unit of PfuTurbo® Hotstart DNA polymerase in PCR reaction buffer (supplied with polymerase) in a total volume of 20 µl. PCR reactions were carried out with a TGradient Thermocycler 96 (Whatman Biometra, Goettingen, Germany) using a 32-cycle program: denaturing at 95° C. for 2 min; 30 cycles of 95° C. for 30 sec, a 60-70° C. gradient (or another specific annealing temperature) for 30 sec, and 72° C. for 3 min; final extension at 72° C. for 10 min. If appropriate, the PCR mixtures were stored at 4° C. until further analysis or processing.

Example 2

Agarose Gel Electrophoresis

Agarose gel electrophoresis was performed according to Sambrook (37) using gels of 50 ml, in 1×Tris Acetate EDTA buffer. DNA was visualized by the inclusion of ethidium bromide in the gel and observation under UV light. Gel images were recorded by a CCD camera and an image analysis system (GeneGnome; Syngene, via Westburg B.V., Leusden, The Netherlands).

Example 3

Analysis and Purification of PCR Products and Enzymatic Digestion

Purification of desired PCR fragments was carried out using a MinElute PCR Purification Kit (Qiagen, via Westburg, Leusden, The Netherlands; product # 28006), according to the manufacturer's instructions. Isolated DNA was quantified by UV spectroscopy and the quality was assessed by agarose gel electrophoresis.

Alternatively, PCR or digestion products were separated by agarose gel electrophoresis (e.g. when multiple fragments were present) using a 1% Tris Acetate EDTA agarose gel. The desired fragment was excised from the gel and recovered using the QIAEX II Gel Extraction Kit (Qiagen; product # 20051), according to the manufacturer's instructions.

Example 4

Quantification of DNA by UV Spectroscopy

Optical density of nucleic acids was determined using a NanoDrop ND-1000 Spectrophotometer (Isogen Life Science, Maarssen, The Netherlands) according to the manufacturer's instructions. The DNA concentration was measured by analysis of the optical density (OD) at 260 nm (one $OD_{260nm}$ unit=50 µg/ml). For all samples, the buffer in which the nucleic acids were dissolved was used as a reference.

Example 5

Restriction Enzyme Digestions

Restriction enzymes and supplements were obtained from New England Biolabs (Beverly, Mass., USA) or Fermetas (Vilnius, Lithuania) and used according to the manufacturer's instructions.

DNA (100 ng) was digested with 5 units of enzyme(s) in the appropriate buffer in a final volume of 10 µl (reaction volumes were scaled up as appropriate). Digestions were incubated at the recommended temperature for a minimum of 60 min. For fragments requiring double digestions with restriction enzymes which involve incompatible buffers or temperature requirements, digestions were performed sequentially. If necessary digestion products were purified by agarose gel electrophoresis and gel extraction.

Example 6

Ligation of DNA Fragments

Ligations of DNA fragments were performed with the Quick Ligation Kit (New England Biolabs) according to the manufacturer's instructions. For each ligation, vector DNA was mixed with approximately three-fold molar excess of insert DNA.

Example 7

Transformation of *E. coli*

Plasmid DNA (1-5 µl of DNA solution, typically 2 µl of DNA ligation mix) was transformed into One Shot DH5α-$T1^R$ or MACH-1 $T1^R$ competent *E. coli* cells (Invitrogen, Breda, The Netherlands; product # 12297-016) using the heat-shock method, according to the manufacturer's instructions. Next, cells were plated on Luria-Bertani (LB) agar plates containing 50 µg/ml ampicillin. Plates were incubated for 16-18 h at 37° C. until bacterial colonies became evident.

Example 8

Screening of Bacterial Colonies by PCR

Bacterial colonies were screened for the presence of vectors containing the desired sequences via colony PCR using the HotStarTaq Master Mix Kit (Qiagen; product # 203445) and the appropriate forward and reverse primers (Appendix 1). Selected colonies were lightly touched with a 20 µl pipette tip and touched briefly in 2 ml LB for small scale culture, and then resuspended in the PCR mix. PCR was performed with a TGradient Thermocycler 96 using a 35-cycle program: denaturation at 95° C. for 15 min; 35 cycles of 94° C. for 30 sec, 55° C. for 30 sec and 72° C. for 2 min; followed by a final extension step of 10 min at 72° C. If appropriate, the PCR mixtures were stored at 4° C. until analysis by agarose gel electrophoresis.

Example 9

Plasmid DNA Isolation from *E. coli* Culture

Plasmid DNA was isolated from *E. coli* cultures using the following kits from Qiagen (via Westburg, Leusden, The Netherlands), according to the manufacturer's instructions. For bulk plasmid preparation (50-150 ml culture), either a HiSpeed Plasmid Maxi Kit (product # 12663) or a HiSpeed Plasmid Midi Kit (product # 12643) was used. For small scale plasmid preparation (±2 ml culture) a Qiaprep Spin Miniprep Kit (product # 27106) was used and DNA was eluted in 50 μl elution buffer (supplied with kit).

Example 10

DNA Sequencing

Plasmid DNA was sequenced using standard procedures known in the art. Sequences were analyzed using Vector NTI software (Informax, Oxford, UK).

Example 11

Transient Expression in HEK-293F Cells

Freestyle™ 293-F (a HEK-293 subclone adapted to suspension growth and chemically defined Freestyle medium, e.g. HEK-293F) cells were obtained from Invitrogen and transfected according to the manufacturer's protocol using 293fectin (Invitrogen).

Example 12

Construction of pTomG4

A Vector for the Expression of Variable Heavy Chain Regions with the Constant Region of Human IgG4

Genomic DNA was isolated from a blood sample of a volunteer and used as a template in a PCR with primers IGG4gene2f and IGG4gene2r (see table below), amplifying the complete genomic constant region of the heavy chain of IgG4 and introducing suitable restriction sites for cloning into the mammalian expression vector pEE6.4 (Lonza Biologics). The PCR fragment was purified and cloned into pEE6.4. For this the PCR product was digested with HindIII and EcoRI, followed by heat inactivation of the restriction enzymes. The pEE6.4 vector was digested HindIII and EcoRI, followed by heat inactivation of the restriction enzymes and dephosphorylation of the vector fragment with shrimp alkaline phosphatase, followed by heat inactivation of the phosphatase. The IgG4 fragment and the pEE6.4HindIII/EcoRI dephosphorylated vector were ligated and transformed into competent MACH1-T1$^R$ cells (Invitrogen). Three clones were grown in LB and plasmid DNA was isolated from a small culture (1.5 mL). Restriction digestion revealed a pattern consistent with the cloning of the IgG4 fragment in the pEE6.4 vector. Plasmid DNA from two clones was transformed in DH5α-T1$^R$ E. coli and plasmid DNA was isolated and the constructs were checked by sequence analysis of the insert and one clone was found to be identical to a genomic IgG4 clone from the Genbank database, apart from some minor differences in introns. These differences are presumably either polymorphisms or sequence faults in the Genbank sequence. The plasmid was named pTomG4.

TABLE 1 primer sequences

| Name | Oligo Sequence |
|---|---|
| VLexbetv1rev | AGCCACCGTACGTTTGATTTCCAGCTTGGTGCCTCC (SEQ ID NO: 1) |
| VLex betv1for | GATGCAAGCTTGCCGCCACCATGGAGTCACAGATTCAGGCATTT (SEQ ID NO: 2) |
| VHexbetv1rev | CGATGGGCCCTTGGTGCTGGCTGAGGAGACGGTGACTGAGGT (SEQ ID NO: 3) |
| VLexbetv1for | GATGCAAGCTTGCCGCCACCATGAAATGCAGCTGGGTTATCTTC (SEQ ID NO: 4) |
| VLexfeld1rev | AGCCACCGTACGTTTTATTTCCAACTTTGTCCCCGA (SEQ ID NO: 5) |
| VLex feld1for | GATGCAAGCTTGCCGCCACCATGGAATCACAGACTCAGGTCCTC (SEQ ID NO: 6) |
| VHexfeld1rev | CGATGGGCCCTTGGTGCTGGCTGCAGAGAAAGTGACCAGAGT (SEQ ID NO: 7) |
| VHexfeld1for | GATGCAAGCTTGCCGCCACCATGGGATGGAGCTATATCATCCTC (SEQ ID NO: 8) |
| IGG4gene2r | TGAGAATTCGGTGGGTGCTTTATTTCCATGCT (SEQ ID NO: 9) |
| IGG4gene2f | GTAGAAGCTTACCATCGCGGATAGACAAGAACC (SEQ ID NO: 10) |
| RACEKmm1 | TGTTAACTGCTCACTGGATGGTGGGA (SEQ ID NO: 11) |
| RACEG1mm1 | TCCCTGGGCACAATTTTCTTGTCCACC (SEQ ID NO: 12) |
| ShortUPMH3 | TGAAAGCTTCTAATACGACTCACTATAGGGC (SEQ ID NO: 13) |
| LongUPMH3 | TGAAAGCTTCTAATACGACTCACTATAGGGCAAGCAGTGGTATCAACGCAGAGT (SEQ ID NO: 14) |

Example 13

Cloning of the Variable Regions of the Mouse Anti-Betv1 and Anti-Feld1 Antibodies Total RNA was prepared from 0.3×10$^5$ (Betv1) or 0.9×10$^5$ (Feld1) mouse hybridoma cells (For Betv1: clone 2H8 from ref. 38 and for Feld1: clone 4F7 from ref. 39 with the RNeasy kit (Qiagen, Westburg, Leusden, Netherlands) according to the manufacturer's protocol.

5'-RACE-Complementary DNA (cDNA) of RNA was prepared from approximately 100 ng total RNA, using the SMART RACE cDNA Amplification kit (BD Biosciences Clontech, Mountain View, Calif., USA), following the manufacturer's protocol.

The VL and VH regions of the Betv1 and Feld1 antibody were amplified by PCR. For this PfuTurbo® Hotstart DNA polymerase (Stratagene) was used according to the manufacturer's instructions. Each reaction mix contained 200 μM mixed dNTPs (Roche Diagnostics), 12 μmol of the reverse primer (RACEG1mm1 for the VH region and RACEKmm1 for the VL region), 7.2 μmol UPM-Mix (UPM-Mix: 2 μM ShortUPMH3 and 0.4 μM LongUPMH3 oligonucleotide), 0.6 μl of the 5'RACE cDNA template as described above, and 1.5 unit of PfuTurbo® Hotstart DNA polymerase in PCR reaction buffer (supplied with polymerase) in a total volume of 30 μl.

PCR reactions were carried out with a TGradient Thermocycler 96 (Whatman Biometra) using a 35-cycle program: denaturing at 95° C. for 2 min; 35 cycles of 95° C. for 30 sec, a 55° C. for 30 sec, and 72° C. for 1.5 min; final extension at 72° C. for 10 min. The reaction products were separated by agarose gel electrophoresis on a 1% TAE agarose gel and stained with ethidium bromide. Bands of the correct size were cut from the gels and the DNA was isolated from the agarose using the QiaexII gel extraction kit (Qiagen).

Gel isolated PCR fragments were A tailed by a 10 min 72° C. incubation with 200 μM dATP and 2.5 units Amplitaq (Perkin Elmer) and purified using minielute columns (Qiagen). A-tailed PCR fragments were cloned into the pGEMTeasy vector (Promega) using the pGEMT easy vector system II kit (Promega), following the manufacturer's protocol. 2 μl of the ligation mixture was transformed into OneShot DH5αT1R competent *E. Coli* (Invitrogen) and plated on LB/Amp/IPTG/Xgal plates. Four, insert containing, white colonies each for the VH and VL sequences were picked and the inserts were sequenced. The deduced amino acid sequences of the VH and VL of Betv1 are given in SEQ ID NO:15 and 16 and the deduced amino acid sequences of Feld1 are depicted in SEQ ID NO:17 and 18.

```
VH sequence Betv1 (SEQ ID NO: 15):
mkcswviffflmavvtgvnsevqlqqsgaelvkpgasvklsctasgfnikd
tyihwvkqrpeqglewvgridpatgntrydpkfqgkatitadtssntayl
qlssltsedtavyycasfrpgyaldywgqgtsvtvss VL sequence Betv1 (SEQ ID NO: 16):
mesqiqafvfvflwlsgvdgdivmtqshkfmstsvgdrvsftckasqdvf
tavawyqqkpgqspklliywastrrtgvpdrftgsgsgtdytltissvqa
edlalyycqqhfstpptfgggtkleik VH sequence Feld1 (SEQ ID NO: 17):
mgwsyiilflvatatdvhsqvqlqqpgaelvkpgasvklsckasgysfts
ywmhwlkqrpgqglewigeinpnngrtyynekfktkatltvdkssstaym
qlnsltsedsavyycarrltmvesfaywgqgtlvtfsa VL sequence Feld1 (SEQ ID NO: 18):
mesqtqvlmsllfwvsgtcgdivmtqspssltvtagekvtmsckssqsll
nsgnqknyltwyqqkpgqppklliywastresgvpdrftgsgsgtdfslt
issvqaedlaiyycqndysypftfgsgtkleik
```

Example 14

Construction of pConG1fBetV1

A Vector for the Production of the Heavy Chain of Betv1-IgG1

The $V_H$ coding region of mouse anti-BetV1 antibody was amplified by PCR from a plasmid containing this region (example 13) using the primers VHexbetv1for and VHexbetv1rev, introducing suitable restriction sites for cloning into pConG1f0.4 and an ideal Kozak sequence. The VH fragment was gel purified and cloned into pConG1f0.4. For this the PCR product and the pConKappa0.4 vector were digested with HindIII and ApaI and purified. The $V_H$ fragment and the pConG1f0.4HindIII-ApaI digested vector were ligated and transformed into competent DH5α-T1$^R$ cells. A clone was selected containing the correct insert size and the correct sequence was confirmed. This plasmid was named pConG1fBetv1.

Example 15

Construction of pConKBetv1

A Vector for the Production of the Light Chain of Betv1

The $V_L$ coding region mouse anti-BetV1 antibody was amplified from a plasmid containing this region (example 13) using the primers VLexbetv1for and VLexbetv1rev, introducing suitable restriction sites for cloning into pConK0.4 and an ideal Kozak sequence. The PCR product and the pConKappa0.4 vector were digested with HindIII and BsiWI and purified. The $V_L$ fragment and the pConKappa0.4HindIII-BsiWI digested vector were ligated and transformed into competent DH5α T1$^R$ *E. coli*. A clone was selected containing the correct insert size and the sequence was confirmed. This plasmid was named pConKBetv1.

Example 16

Construction of pTomG4Betv1

A Vector for the Production of the Heavy Chain of Betv1-IgG4

To construct a vector for expression of Betv1-IgG4, the VH region of BetV1 was cloned in pTomG4. For this, pTomG4 and pConG1fBetv1 were digested with HindIII and ApaI and the relevant fragments were isolated. The Betv1 $V_H$ fragment and the pTomG4HindIII-ApaI digested vector were ligated and transformed into competent DH5α-T1$^R$ cells. A clone was selected containing the correct insert size and the sequence was confirmed. This plasmid, was named pTomG4Betv1.

Example 17

Construction of pConG1fFeld1

A Vector for the Production of the Heavy Chain of Feld1-IgG1

The $V_H$ coding region of mouse anti-Feld1 antibody was amplified by PCR from a plasmid containing this region (example 13) using the primers VHexfeld1for and VHexfeld1rev, introducing suitable restriction sites for cloning into pConG1f0.4 and an ideal Kozak sequence. The VH fragment was gel purified and cloned into pConG1f0.4. For this the PCR product and the pConKappa0.4 vector were digested with HindIII and ApaI and purified. The $V_H$ fragment and the pConG1f0.4HindIII-ApaI digested vector were ligated and transformed into competent DH5α-T1$^R$ cells. A clone was selected containing the correct insert size and the correct sequence was confirmed. This plasmid was named pConG1fFeld1.

Example 18

Construction of pConKFeld1

A Vector for the Production of the Light Chain of Feld1

The $V_L$ coding region mouse anti-'Feld1 antibody was amplified from a plasmid containing this region (example 13) using the primers VLexfeld1for and VLexfeld1rev, introducing suitable restriction sites for cloning into pConK0.4 and an ideal Kozak sequence. The PCR product and the pConKappa0.4 vector were digested with HindIII and BsiWI and purified. The $V_L$ fragment and the pConKappa0.4HindIII-BsiWI digested vector were ligated and transformed into competent DH5α T1$^R$ E. coli. A clone was selected containing the correct insert size and the sequence was confirmed. This plasmid was named pConKFeld1.

Example 19

Construction of pTomG4Feld1

A Vector for the Production of the Heavy Chain of Feld1-IgG4

To construct a vector for expression of Feld1-IgG4, the VH region of Feld1 was cloned in pTomG4. For this, pTomG4 and pConG1fFeld1 were digested with HindIII and ApaI and the relevant fragments were isolated. The Feld1 $V_H$ fragment and the pTomG4HindIII-ApaI digested vector were ligated and transformed into competent DH5α-T1$^R$ cells. A clone was selected containing the correct insert size and the sequence was confirmed. This plasmid was named pTomG4Feld1 .

Example 20

Construction of Antibody Expression Vectors for the Expression of 2F8-IgG4 and 7D8-IgG4

Expression vectors for the expression of HuMab 2F8 (IgG1-EGFR) and HuMab 7D8 (IgG1-CD20) were constructed. The VH and VL coding regions of HuMab 2F8 (WO 02/100348) and HuMab 7D8 (WO 04/035607) were cloned in the expression vector pConG1f (Lonza Biologics) for the production of the IgG1 heavy chain and pConKappa for the production of the kappa light chain, yielding the vectors pConG1f2F8, pConG1f7D8, pConKappa2F8 and pConKappa7D8. The VH regions of pConG1f2F8 and pConG1f7D8 were removed from these vectors by a HindIII/ApaI digestion and inserted into a HindIII/ApaI digested pTomG4 vector, resulting in pTomG42F8 and pTomG47D8 respectively.

Example 21

Production of Betv1-IgG1, Betv1-IgG4, Feld1-IgG1 and Feld1-IgG4 by Transient Expression in HEK-293F Cells Antibodies were produced from all constructs by cotransfecting the relevant heavy and light chain vectors in HEK-293F cells using 293fectin according to the manufacturer's instructions. For Betv1-IgG1, pConG1Betv1 and pConKBetv1 were coexpressed. For Betv1-IgG4, pTomG4Betv1 and pConKBetv1 were coexpressed. For Feld1-IgG1, pConG1Feld1 and pConKFeld1 were coexpressed. For Feld1-IgG4, pTomG4Feld1 and pConKFeld1 were coexpressed. For IgG1-EGFr, pConG1f2F8 and pConKappa2F8 were coexpressed. For IgG4-EGFr, pTomG42F8 and pConKappa2F8 were coexpressed. For IgG1-CD20, pConG1f7D8 and pConKappa7D8 were coexpressed. For IgG4-CD20, pTomG47D8 and pConkappa7D8 were coexpressed.

Example 22

Purification of IgG1 and IgG4 Antibodies

IgG1 and IgG4 antibodies were purified by protein A affinity chromatography. The cell culture supernatants were filtered over a 0.20 μM dead-end filter, followed by loading on a 5 ml Protein A column (rProtein A FF, GE Healthvcare) and elution of the IgG with 0.1 M citric acid-NaOH, pH 3. The eluate was immediately neutralized with 2 M Tris-HCl, pH 9 and dialyzed overnight to 12.6 mM sodium phosphate, 140 mM NaCl, pH 7.4 (B. Braun, Oss, The Netherlands). After dialysis, samples were sterile filtered over a 0.20 μM dead-end filter. Concentration of the purified IgGs was determined by nephelometry and absorbance at 280 nm. Purified proteins were analyzed by SDS-PAGE, IEF, Mass spectrometry and Glycoanalysis.

Example 23

SDS-PAGE Analysis of Purified IgGs

After purification, the Betv1 and Feld1, IgG1 and IgG4 antibodies were analyzed on non-reducing SDS-PAGE. The Bis-Tris electrophoresis method used is a modification of the Laemmli method (Laemmli 1970 *Nature* 227(5259): 680-5), where the samples were run at neutral pH. The SDS-PAGE gels were stained with Coomassie and digitally imaged using the GeneGenius (Synoptics, Cambridge, UK).

Figure 1:
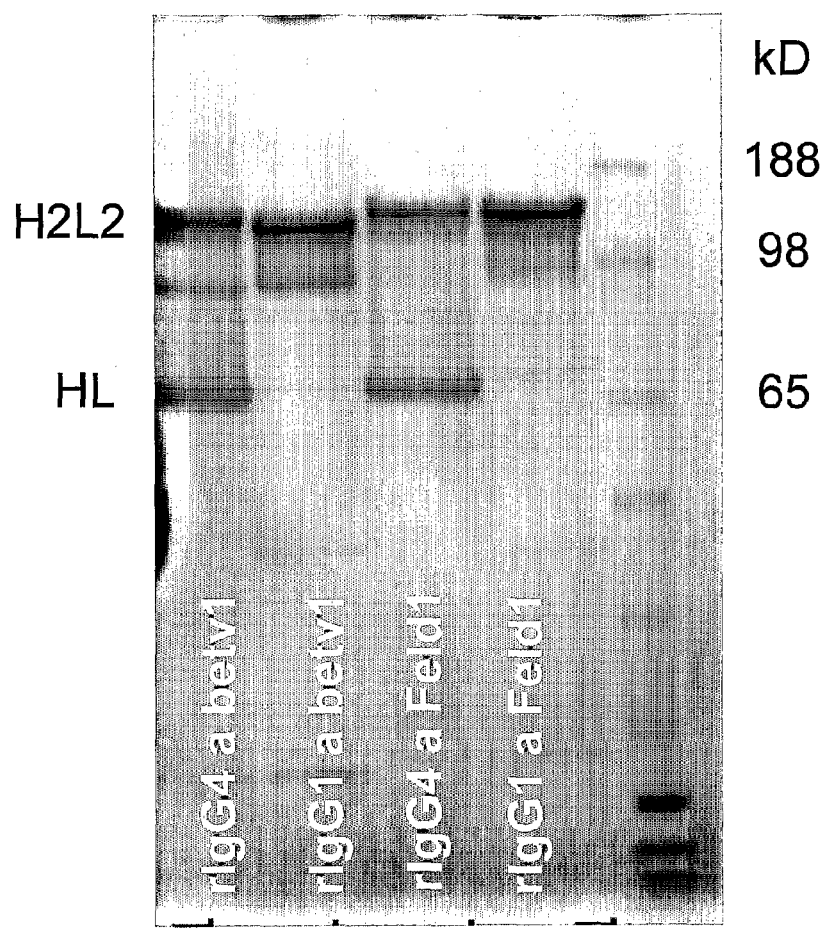
FIG. 1. SDS-Page analysis of purified recombinant IgG1 and IgG4. After purification, the Betv1 and Feld1, IgG1 and IgG4 antibodies were analyzed on non-reducing SDS-PAGE.

As can be seen in FIG. 1, Betv1 and Feld1 IgG1 showed 1 major band representing the full length tetrameric (2 heavy and two light chains) Feld1 and Betv1 IgG1 molecules. Betv1 and Feld1 IgG4 showed to have, besides the major band representing the tetrameric IgG4 molecule, substantial amounts of half-molecules (i.e. one heavy band one light chain).

Example 24

Evaluation of IgG4 Half Molecule Exchange in Mice

Five nu/nu Balb/c mice 6-8 weeks of age were used to follow the exchange of IgG4 half molecules. The mice were housed in a barrier unit of the Central Laboratory Animal Facility (Utrecht, The Netherlands) and kept in filter-top cages with water and food provided ad libitum. All experiments were approved by the Utrecht University animal ethics committee.

Chimeric antibodies were administered intraperitoneally. Blood samples (75-100 μl) were drawn at 4.25 hours, 24 hours, 48 hours and 72 hours after administration. Blood was collected in heparin-containing vials and centrifuged for 5 minutes at 10.000 g to separate plasma from cells. Plasma was stored at −20° C. for determination of antigen specific antibody and bispecific antibody levels.

In this experiment the exchange of chimeric IgG4 half molecules (n=2) was compared with the exchange of IgG1 half molecules (n=3). Mixtures of Bet v 1 and Fel d 1 specific antibodies (IgG1 or IgG4) were administered to the mice at a dose of 600 µg (300 µg of each antigen specific antibody) in 200 µl per mouse.

Plasma concentrations of Bet v 1 or Fel d 1 binding antibodies were measured in the antigen binding test. To this end, plasma samples were incubated with 0.75 mg of protein G Sepharose (Amersham Biosciences, Uppsala, Sweden) in 750 µl PBS-IAT (PBS supplemented with 1 µg/ml IVIg, 0.3% bovine serum albumin, 0.1% Tween-20 and 0.05% (w/v) $NaN_3$) in the presence of $^{125}$I-labeled Bet v 1 or $^{125}$I-labeled Fel d 1 for 24 h. Next, the Sepharose was washed with PBS-T (PBS supplemented with 0.1% Tween-20 and 0.05% (w/v) $NaN_3$) and the amount of radioactivity bound relative to the amount of radioactivity added was measured. The concentration of Bet v 1 or Fel d 1 specific IgG was calculated using purified Bet v 1 specific antibodies or Fel d 1 specific antibodies as a standard (range 0-200 ng per test as determined by nephelometer). The concentration of bispecific IgG was measured in two variants of the heterologous cross-linking assay. In the first assay, plasma was incubated for 24 h with Sepharose-coupled Bet v 1 (0.5 mg) in a total volume of 300 µl in PBS-IAT. Subsequently, the Sepharose was washed with PBS-T and incubated for 24 h with $^{125}$I-labeled Fel d 1, after which the Sepharose was washed with PBS-T and the amount of radioactivity bound relative to the amount of radioactivity added was measured. The concentration of bispecific IgG (Bet v 1-Fel d 1) was calculated using the calibration curve of the Fel d 1 binding test, which was obtained from purified Fel d 1 binding rIgG. In the second assay Fel d 1-Bet v 1 cross-linking activity was measured in a similar procedure using Sepharose-coupled rFel d 1 (0.5 mg) and $^{125}$I-labeled Bet v 1. The concentration of bispecific IgG (Fel d 1-Bet v 1) was calculated using purified Bet v 1 specific rIgG as a standard (same curve as in Bet v 1 binding test).

Figure 2:
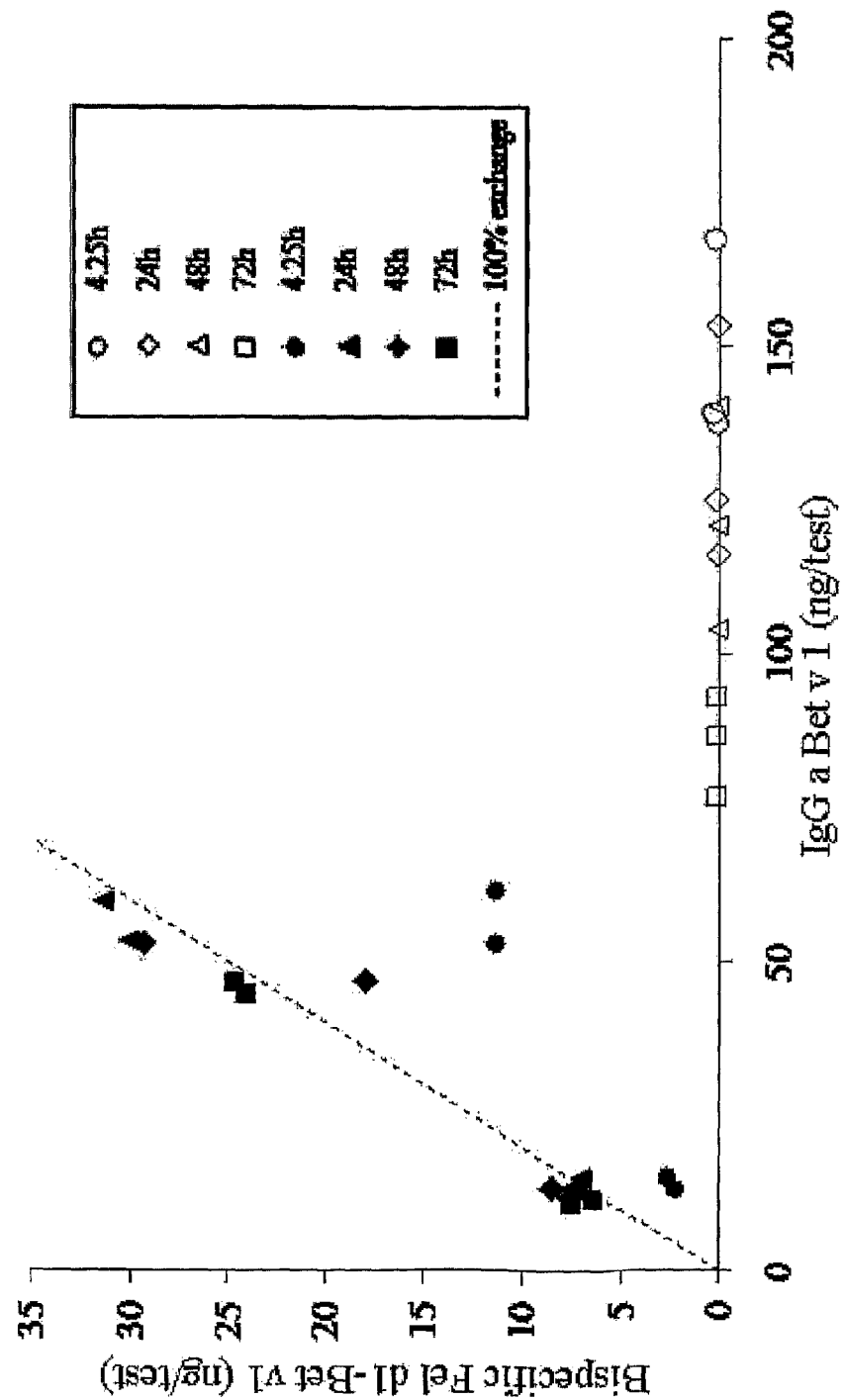
FIG. 2. Bispecific IgG levels in nu/nu Balb/c mice at different time points. The amount of bispecific IgG as determined in the heterologous cross-linking assay was plotted versus the amount of Bet v 1 specific IgG as determined in the Bet v 1 binding test. Data from IgG1 and IgG4 containing plasma samples are represented by open symbols and closed symbols, respectively. The dashed line represents the calculated amount of bispecific IgG, if the exchange of IgG half molecules is random and complete.

In FIG. 2 the concentration of bispecific IgG (Fel d 1-Bet v 1) is plotted versus the concentration of Bet v 1 binding IgG at different time points. No bispecific IgG was observed in the mice dosed with IgG1 mixes in contrast to the mice dosed with IgG4. After 24 h the generation of bispecific IgG4 was maximal and corresponded to an exchange of 100%.

Figure 3A:
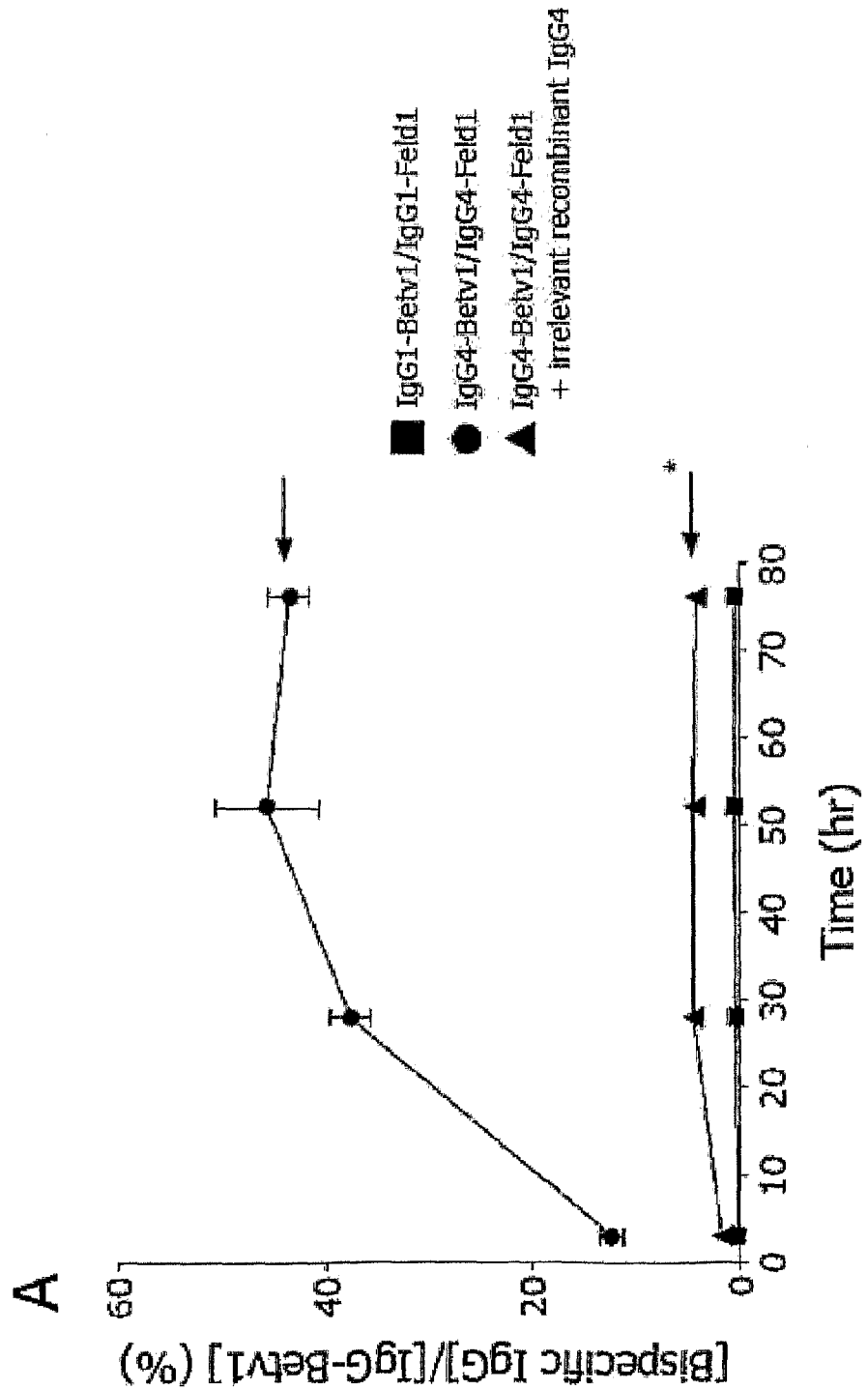
FIG. 3. Bispecific human IgG4 molecules are generated in vivo. (A) Groups (n=5) of SCID mice were injected with chimeric antibody mixtures: 100 μg IgG1-Betv1/100 μg IgG1-Feld1 (squares), 100 μg IgG4-Betv1/100 μg IgG4-Feld1 (circles), or 3) 100 μg IgG4-Betv1/100 μg IgG4-Feld1+ 2,000 μg irrelevant recombinant IgG4 (IgG4-EGFR; triangles). Generation of bispecific antibodies was followed in time by assessing the bispecific activity to Bet v 1 and Fel d 1 in plasma. The fraction of bispecific IgG relative to the total IgG-Bet v 1 concentration was expressed as percentage. The arrow with asterisk indicates the bispecific reactivity level expected in mice receiving IgG4-Betv1/IgG4-Feld1 in the presence of excess irrelevant IgG4 (4%), the arrow without asterisk that in mice receiving IgG4-Betv1/IgG4-Feld1 mixture (50%). Error bars represent SEM. (B) Monospecific cross-linking activity was tested by assessing cross-linking of radiolabeled Fel d 1 to Fel d 1-coupled Sepharose in mouse plasma. Monospecific reactivity was expressed as the ratio between the amount of radiolabeled Fel d 1 bound by cross-linking and total IgG-Feld1 in order to correct for the clearance of IgG. Error bars represent SEM.

In FIG. 3A the formation of bispecific human IgG4 is followed in time. Bispecific antibodies appeared in time in the plasma of mice injected with mixtures of IgG4, but not IgG1, with bispecific reactivity achieving a maximum of almost 50% after 1-2 days incubation (note: if equal amounts of IgG4-Betv1 and IgG4-Feld1 are exchanged, maximal 50% of the IgG4-Betv1 half-antibodies will be incorporated in the bispecific fraction after random and complete exchange of half-antibodies). A random Fab arm exchange between equal amounts of IgG4-Betv1 and IgG4-Feld1, would be consistent with approximately half of the IgG4 molecules acquiring bispecificity. As a control, a 20-fold-excess of an additional IgG4 directed against an irrelevant antigen (IgG4 generated from anti-EGFr antibody 2F8) was injected in mice together with IgG4-Betv1 and IgG4-Feld1. The excess irrelevant IgG4 competed with the generation of Betv1-Feld1-bispecific IgG4.

Figure 3B:
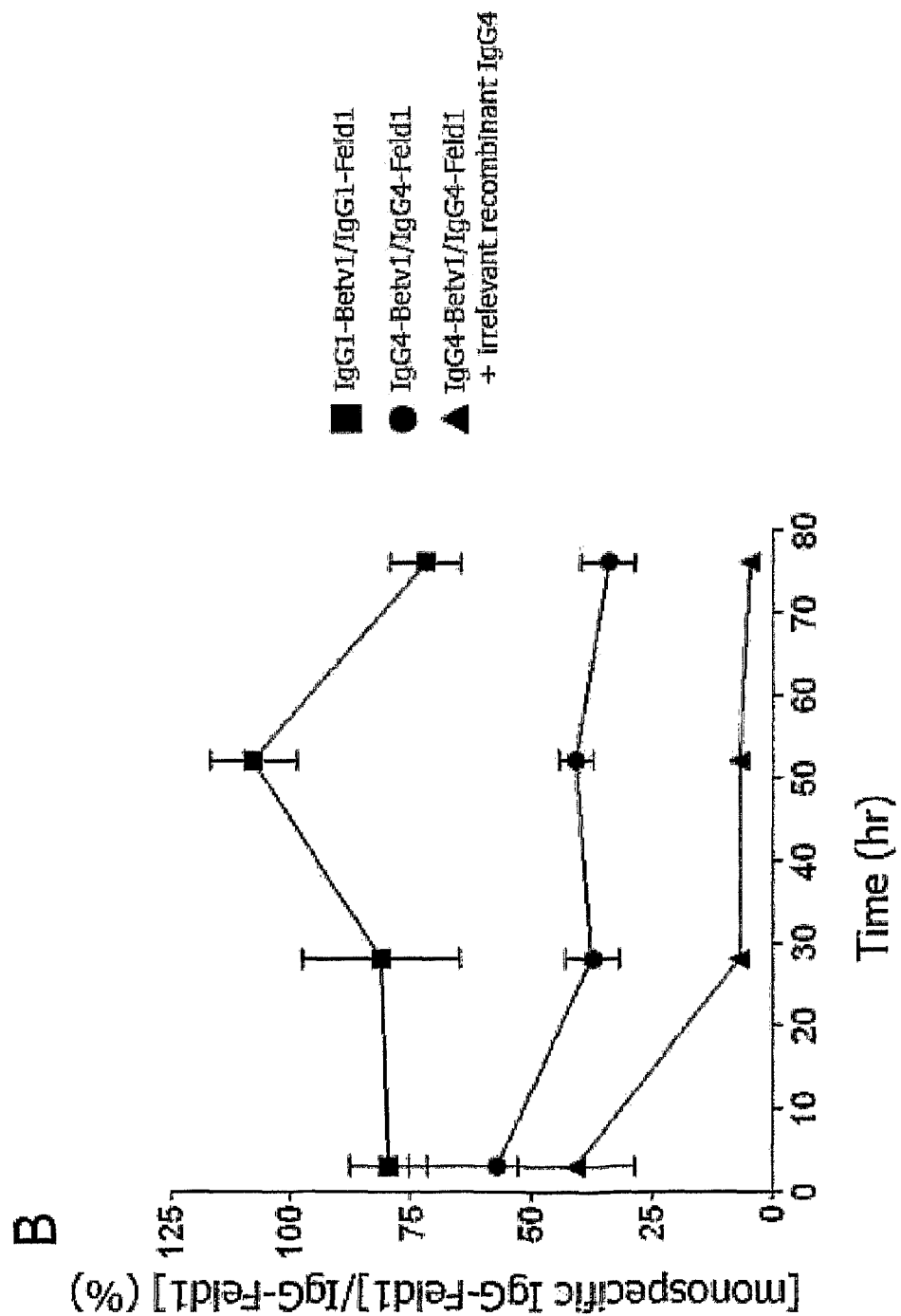

In another experiment (FIG. 3B) the same murine plasma samples were tested for their ability to cross-link radio-labeled soluble Fel d 1 to Sepharose-immobilized Fel d 1. It was found that the monospecific cross-linking activity was decreased in mice dosed with an equal mixture of IgG4s but not IgG1 s, indicating a loss of monospecific cross-linking activity. A maximal reduction of ~50% was reached after about one day. In mice dosed with the additional excess of irrelevant IgG4, monospecific cross-linking activity almost completely disappeared with similar kinetics.

Figure 4:
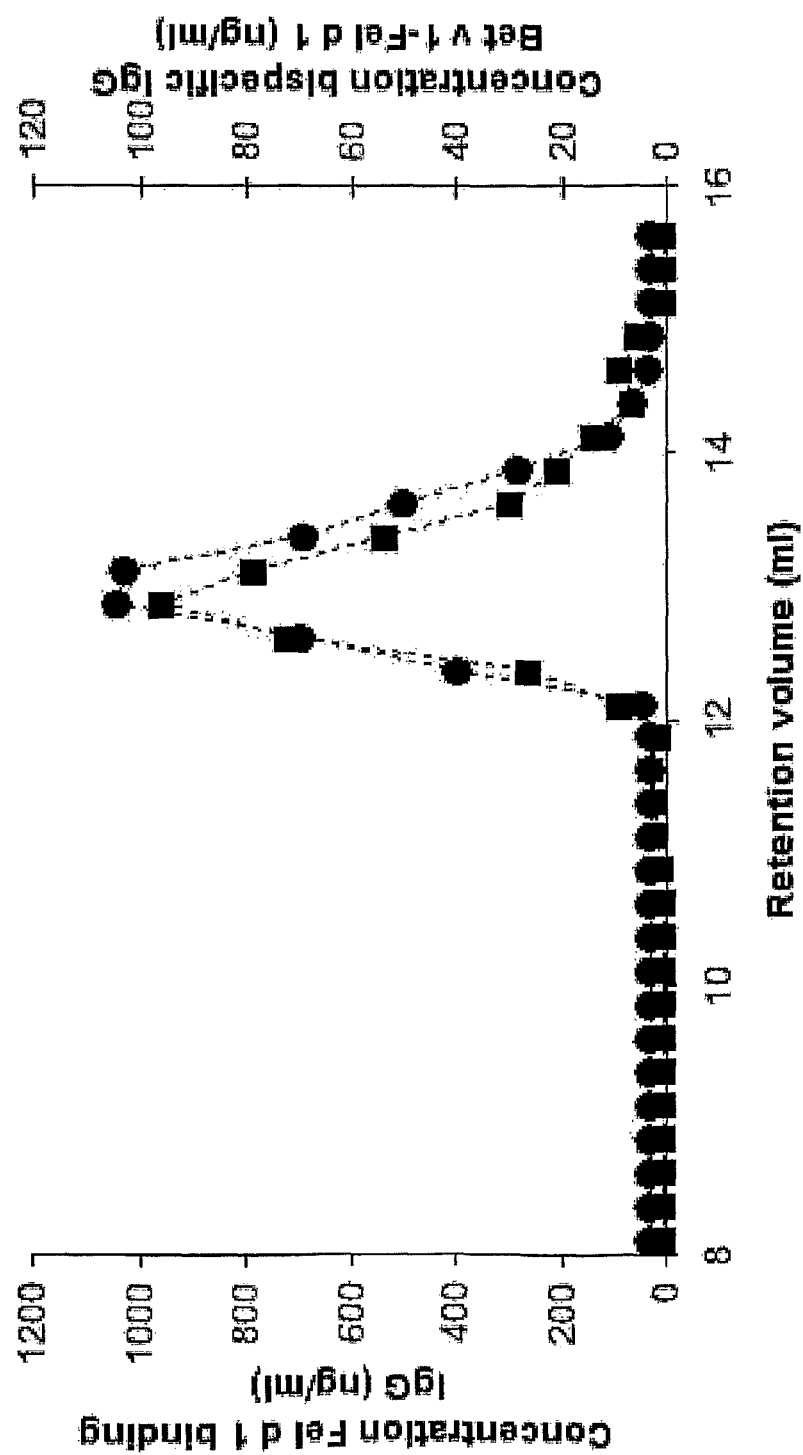
FIG. 4. SEC analysis of bispecific activity in murine plasma.

Size-exclusion chromatography was performed to exclude the possibility that bispecific activity observed in the mice dosed with IgG4 was the result of IgG aggregation (see FIG. 4). For this purpose, a plasma sample (drawn at t=24 h) was fractionated on a Superdex200 column, after which Fel d 1 binding IgG and Bet v 1-Fel d 1 cross-linking IgG were measured in the fractions. Fel d 1 binding antibodies eluted in one peak with a retention volume of ~12.9 ml, which corresponds to the retention volume of monomeric IgG. The heterologous Bet v 1-Fel d 1 cross-linking activity was detected in the same fractions indicating that bispecific activity was associated with monomeric IgG. In the rIgG1 containing plasma no Bet v 1-Fel d 1 cross-linking activity was present before fractionation. Also in the eluted fractions no heterologous cross-linking activity was measured (data not shown).

Example 25

Evaluation of Exchange Activity in Whole Blood (Components)

Chimeric antibodies were mixed and subsequently incubated with whole blood, blood cells, plasma or serum to investigate the exchange activity of whole blood (components).

In this experiment the exchange of IgG4 half molecules was evaluated in whole blood from two healthy blood donors, A and B, in which the endogenous plasma level of IgG4 was determined by nephelometry (being 346 and 554 µg/ml, respectively). Whole blood was obtained in vacutainers supplemented with TFPI (Tissue Factor Pathway Inhibitor from Chiron Corporation, Emeryville, Calif.) in a final concentration of 40 µg/ml. Blood cells and plasma were obtained by centrifugation of whole blood. The cellular fraction was washed 3 times with Optimem (Invitrogen, Breda, The Netherlands) and subsequently resuspended in Optimem. Serum was obtained by incubating whole blood in a glass vacutainer with clot activator for 30 min at 37° C., after which the clotted blood was spinned down. The exchange of IgG4 half molecules was evaluated and compared to the exchange of IgG1 half molecules. As a control the blood samples were also incubated in the absence of chimeric antibodies. The following antibodies mixtures were prepared in PBS:
1. Bet v 1 specific IgG4 (10 µg) and Fel d 1 specific IgG4 (10 µg)
2. Bet v 1 specific IgG1 (10 µg) and Fel d 1 specific IgG1 (10 µg)

These antibody mixtures were incubated with blood, blood cells, plasma or serum in a total volume of 100 µl (final concentration for each antibody was 0.1 µg/ml) on a horizontal orbital shaker (125 rpm) at 37° C. Final hematocrit in the incubation mixtures with whole blood and blood cells was around ~40%. After 24 h the incubation mixtures were centrifuged for 1 min at 2800 rpm in an Eppendorf centrifuge, after which a sample of 10 µl was drawn in 500 µl PBS-AT (PBS supplemented with 0.3% bovine serum albumin, 0.1% Tween-20 and 0.05% (w/v) $NaN_3$). Samples were stored, if necessary, at 4° C.

Bispecific activity (i.e. Fel d 1-Bet v 1 cross-linking activity) was measured in the heterologous cross-linking assay. In this assay, a sample was incubated for 24 h with 0.5 mg Sepharose-coupled recombinant Fel d 1 in a total volume of 300 µl in PBS-IAT (PBS-AT supplemented with 1 µg/ml IVIg). Subsequently, the Sepharose was washed with PBS-T and incubated for 24 h with $^{125}$I-labeled Bet v 1, after which the Sepharose was washed with PBS-T and the amount of radioactivity bound relative to the amount of radioactivity added was measured.

Figure 5A:
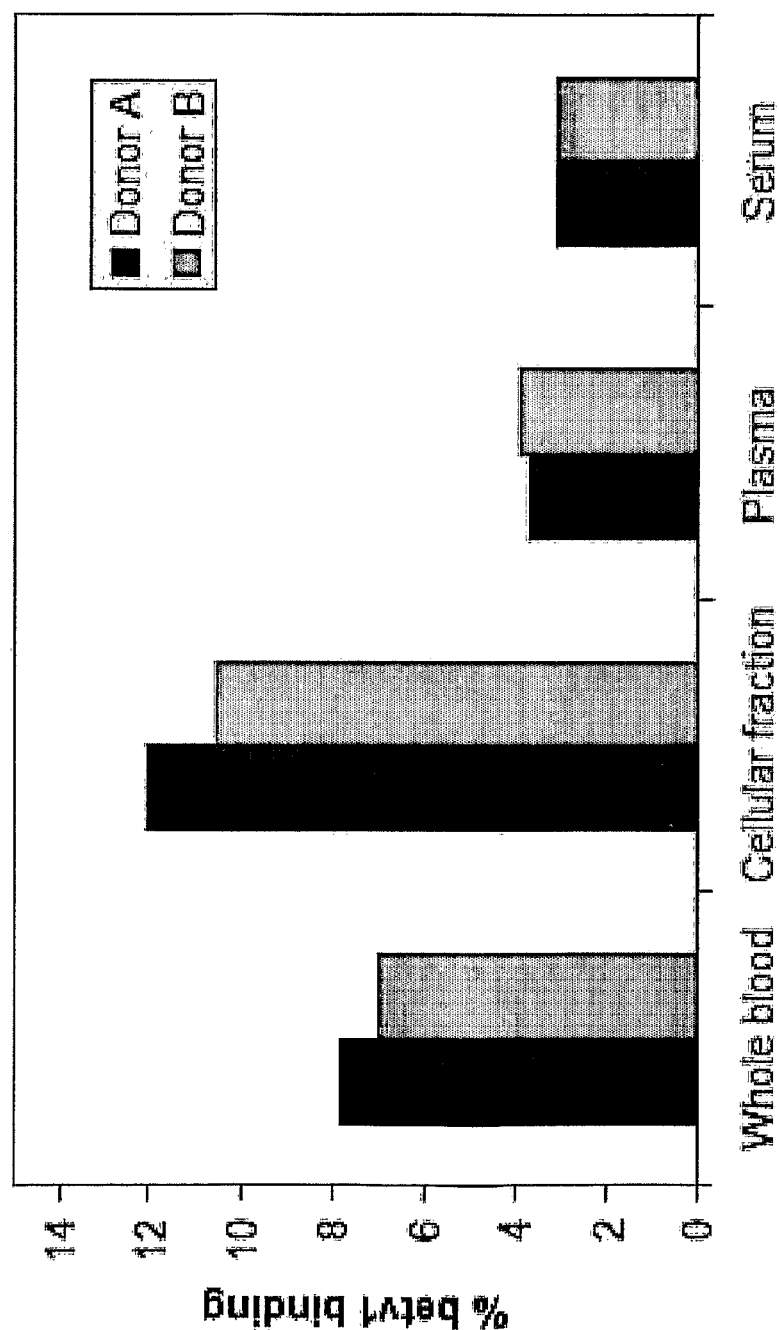
Figure 5B:
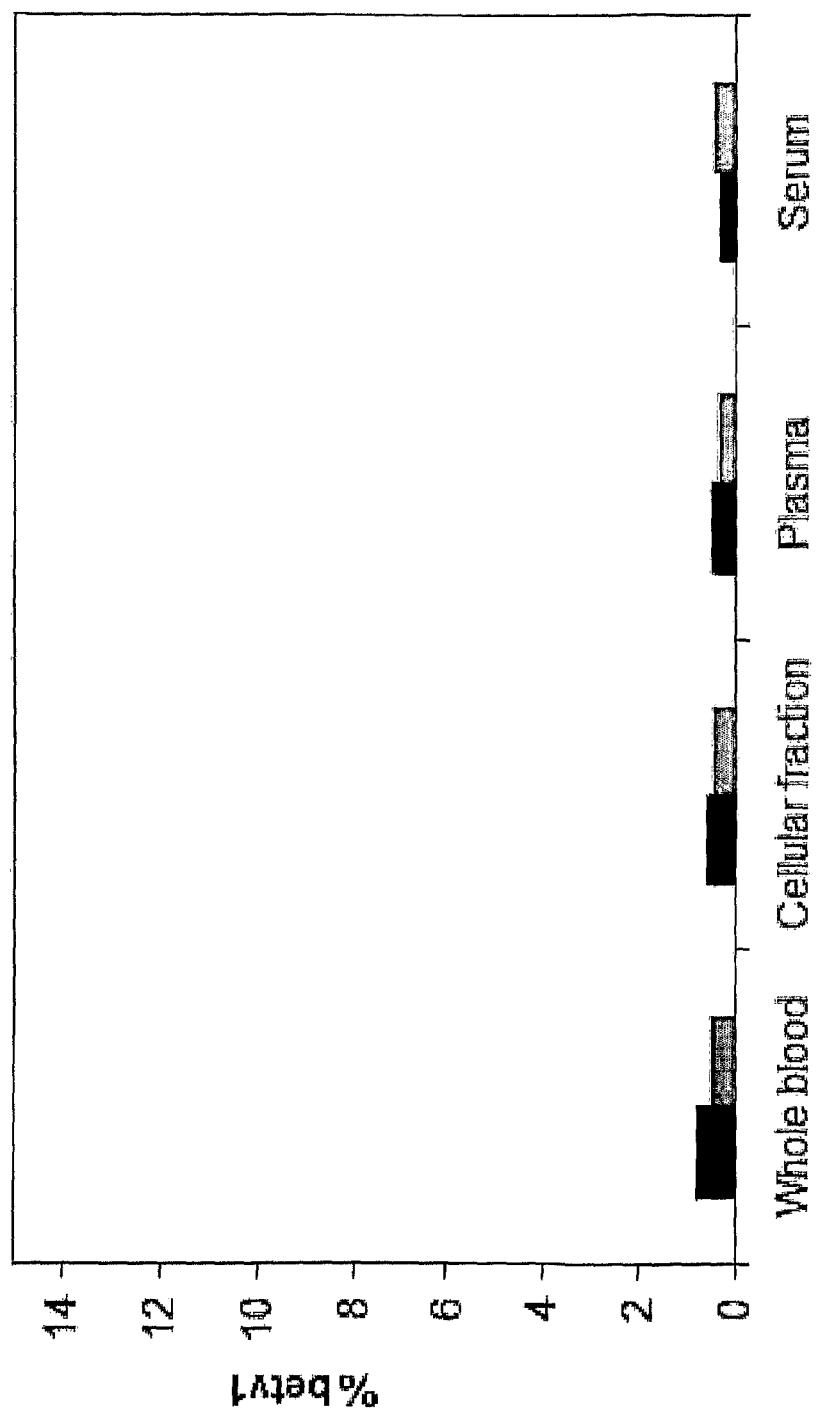
Figure 5C:
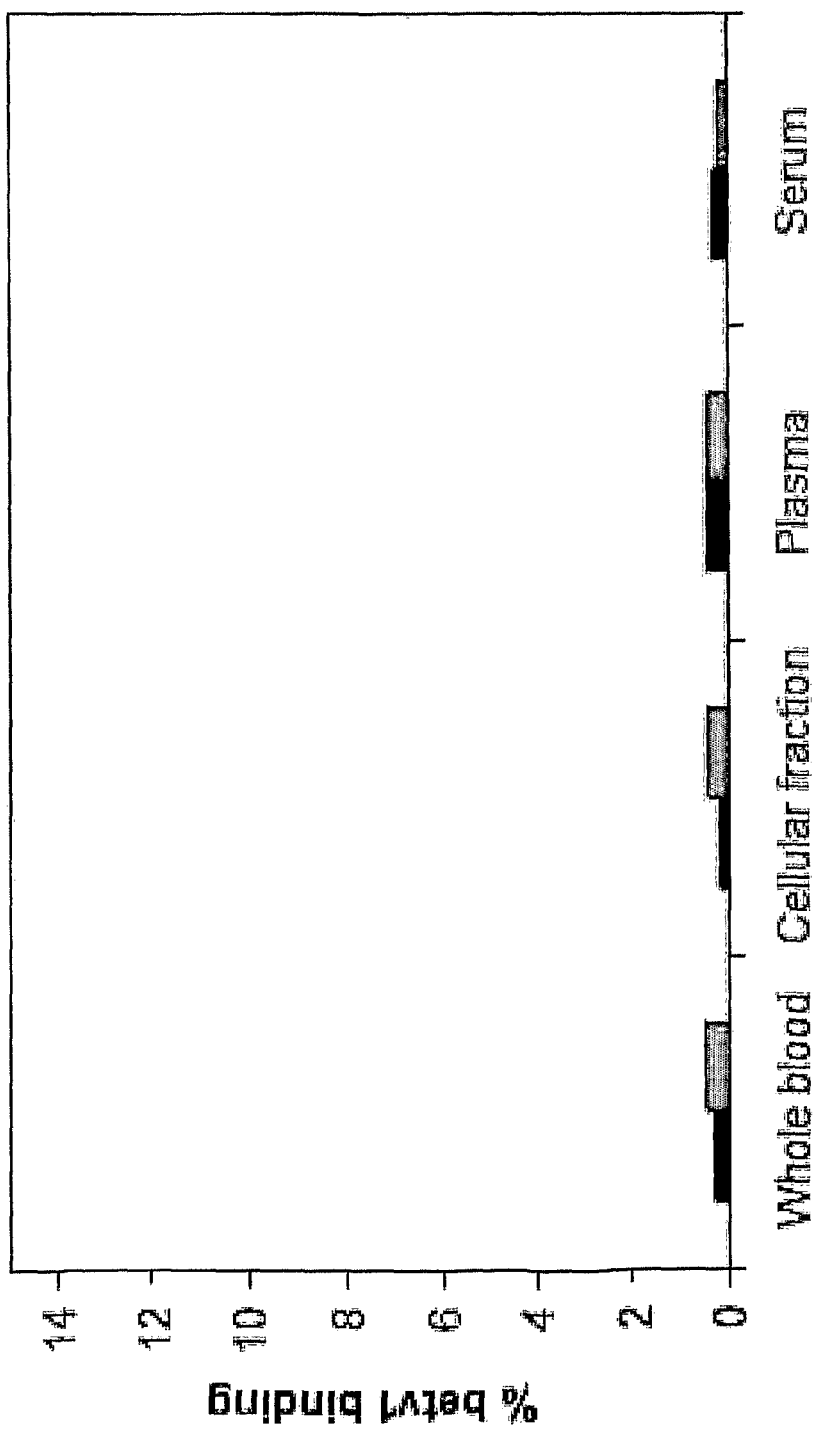

In FIG. 5 bispecific activity is represented as percentage bound $^{125}$I-labeled Bet v 1, which was determined in the heterologous cross-linking assay. Bispecific activity is a measure for the exchange of IgG4 half molecules, which was primarily observed in whole blood and the cellular fraction of whole blood (FIG. 5a). Bispecific levels in the cellular fraction were even higher than in whole blood. This is most likely explained by the fact that in the cellular fraction endogenous IgG4, which can also be exchanged with the added chimeric IgG4 antibodies, is no longer present. Some bispecific activity was also observed in plasma and serum, but this activity was much lower than observed in whole blood and only slightly higher than background level, being 1.7%, which was obtained by incubating the IgG4 mixture in Optimem. No bispecific activity was observed in any of the incubations containing IgG1 (FIG. 5b). Also in the control incubations without chimeric antibodies no bispecific activity was observed (FIG. 5c). Size-exclusion chromatography was performed to exclude the possibility that bispecific activity observed in the IgG4 mix was the result of IgG aggregation. For this purpose, a sample (drawn at t=24 h) was fractionated on a Superdex200 column, after which Fel d 1 binding IgG and Bet v 1-Fel d 1 cross-linking IgG were measured in the fractions. Fel d 1 binding antibodies eluted in one peak with a retention volume of ~12.9 ml, which corresponds to the retention volume of monomeric IgG. The heterologous Bet v 1-Fel d 1 cross-linking activity was detected in the same fractions indicating that bispecific activity was associated with monomeric IgG (data not shown).

Example 26

Evaluation of Blood Cell Mediated IgG4 Exchange Activity

Chimeric antibodies were mixed and subsequently incubated with three different types of human blood cells (i.e. mononuclear cells (MNC), erythrocytes and platelets) to investigate IgG4 exchange activity.

Whole blood from an anonymous donor was drawn in a heparin containing vacutainer and subsequently centrifuged in Percoll (Pharmacia Fine Chemicals, Uppsala, Sweden) to isolate MNCs. The isolated MNCs were resuspended in Optimem serum free culture medium (Invitrogen, Breda, The Netherlands) before use. Freshly purified erythrocytes and platelets (provided by the Blood Cell Research Department of Sanquin) were obtained from two different anonymous donors. These cells were also resuspended in Optimem after being washed 3 times. In addition, platelets were supplemented with 10 mM glucose.

The exchange of IgG4 half molecules was evaluated and compared to the exchange of IgG1 half molecules. The following antibodies mixtures were prepared in PBS:

Bet v 1 specific IgG4 (10 µg) and Fel d 1 specific IgG4 (10 µg)

Bet v 1 specific IgG1 (10 µg) and Fel d 1 specific IgG1 (10 µg)

These antibody mixtures were incubated with $1.8 \times 10^4$ MNCs, $4.0 \times 10^8$ erythrocytes or $3.5 \times 10^4$ platelets in a total volume of 100 µl (final concentration for each antibody was 0.1 µg/ml) on a horizontal orbital shaker (125 rpm) at 37° C. After 48 h the incubation mixtures were centrifuged for 1 min at 2800 rpm in an Eppendorf centrifuge, after which a sample of 10 µl was drawn in 500 µl PBS-AT (PBS supplemented with 0.3% bovine serum albumin, 0.1% Tween-20 and 0.05% (w/v) NaN$_3$). Samples were stored, if necessary, at 4° C.

Bispecific activity (i.e. Fel d 1-Bet v 1 cross-linking activity) was measured in the heterologous cross-linking assay. In this assay, a sample was incubated for 24 h with 0.5 mg Sepharose-coupled recombinant Fel d 1 in a total volume of 300 µl in PBS-IAT (PBS-AT supplemented with 1 µg/ml IVIg). Subsequently, the Sepharose was washed with PBS-T and incubated for 24 h with $^{125}$I-labeled Bet v 1, after which the Sepharose was washed with PBS-T and the amount of radioactivity bound relative to the amount of radioactivity added was measured.

In FIG. 6 bispecific activity is shown as percentage bound $^{125}$I-labeled Bet v 1, which was determined in the heterologous cross-linking assay. All three cell types were able to induce bispecific activity. Some bispecific activity was also observed in Optimem serum free medium, but this activity was much lower than observed in the presence of blood cells. None of the tested cells was able to exchange IgG1 half molecules.

Example 27

Evaluation of IgG4 Exchange by Human and Murine Cell Lines

Chimeric IgG4 antibodies were mixed and subsequently incubated with three different cell lines (i.e. Human Embryo Kidney (HEK) cells, murine B cells or hybridomas) to investigate IgG4 exchange activity.

Cell line J558 (provided by the Antigen Presentation Research Group of Sanquin) was chosen as a source of murine B cells. Hybridomas, which produce an anti-C1 esterase inhibitor, were obtained from the Autoimmune Research Group of Sanquin. Suspension HEK (293F) cells were from Invitrogen, Breda, The Netherlands. All cells were washed three times with PBS, after which the cells were resuspended in PBS.

The exchange of IgG4 half molecules was evaluated by incubating an IgG4 antibody mixture consisting of Bet v 1 specific IgG4 (2 µg) and Fel d 1 specific IgG4 (2 µg) with the aforementioned cells. The antibody mixture was incubated with $24 \times 10^5$ HEK cells, $25 \times 10^5$ murine B cells or $21 \times 10^5$ hybridomas in a total volume of 50 µl (final concentration for each antibody was 80 µg/ml) on a horizontal orbital shaker (125 rpm) at 37° C. After 0 h and 24 h the incubation mixtures were centrifuged for 1 min at 2800 rpm in an Eppendorf centrifuge, after which a sample was drawn in PBS-AT (PBS supplemented with 0.3% bovine serum albumin, 0.1% Tween-20 and 0.05% (w/v) NaN$_3$). Samples were stored, if necessary, at 4° C.

Bispecific activity (i.e. Fel d 1-Bet v 1 cross-linking activity) was measured in the heterologous cross-linking assay. In this assay, sample dilutions were incubated for 24 h with 0.5 mg Sepharose-coupled recombinant Fel d 1 in a total volume of 300 µl in PBS-IAT (PBS-AT supplemented with 1 µg/ml IVIg). Subsequently, the Sepharose was washed with PBS-T and incubated for 24 h with $^{125}$I-labeled Bet v 1, after which the Sepharose was washed with PBS-T and the amount of radioactivity bound relative to the amount of radioactivity added was measured.

In FIG. 7 bispecific activity is shown as percentage bound $^{125}$I-labeled Bet v 1, which was determined in the heterologous cross-linking assay. All three cell types were able to exchange IgG4 half molecules.

Example 28

Evaluation of IgG4 Half Molecule Exchange by Erythrocytes

Chimeric antibodies were mixed and subsequently incubated with human erythrocytes to investigate the exchange of IgG4 half molecules. Erythrocytes were purified from a single donor and stored at 4° C. in SAGM (Saline Adenine Glucose Mannitol) buffer. Before use the cells were washed three times with PBS.

In this experiment the exchange of IgG4 half molecules was compared with the exchange of IgG1. Also, the exchange of IgG4 in the presence of excess irrelevant IgG4 was evaluated. The following antibodies mixtures were prepared in PBS:

Bet v 1 specific IgG4 (4 μg) and Fel d 1 specific IgG4 (4 μg)
Bet v 1 specific IgG1 (4 μg) and Fel d 1 specific IgG1 (4 μg)
Bet v 1 specific IgG4 (4 μg), Fel d 1 specific IgG4 (4 μg) and irrelevant IgG4 specific for antigen X (80 μg)

These mixtures were incubated with erythrocytes in PBS supplemented with 0.05% (w/v) $NaN_3$ in a total volume of 100 μl (final hematocrit was around ~40%) and subsequently incubated on a horizontal orbital shaker (125 rpm) at 37° C. At indicated time points the erythrocytes were centrifuged for 1 min at 2800 rpm in an Eppendorf centrifuge, after which a sample of 10 μl was drawn in 500 μl PBS-AT (PBS supplemented with 0.3% bovine serum albumin, 0.1% Tween-20 and 0.05% (w/v) $NaN_3$). Samples were stored at 4° C. before measuring bispecific activity, bivalency and antigen binding. As a control the same mixtures were also incubated in PBS without erythrocytes.

Levels of Bet v 1 binding antibodies were measured in the antigen binding test. To this end, samples were incubated with 0.75 mg of protein G Sepharose (Amersham Biosciences, Uppsala, Sweden) in 750 μl PBS-IAT (PBS-AT supplemented with 1 μg/ml IVIg) in the presence of $^{125}$I-labeled Bet v 1 for 24 h. Next, the Sepharose was washed with PBS-T (PBS supplemented with 0.1% Tween-20 and 0.05% (w/v) $NaN_3$) and the amount of radioactivity bound relative to the amount of radioactivity added was measured. The concentration of Bet v 1 specific IgG was calculated using purified Bet v 1 specific antibodies as a standard (range 0-200 ng per test as determined by nephelometer). Bispecific activity in experiments using Fel d 1 and Bet v 1 specific antibodies was measured in the Feld1-Betv1 cross-linking assay. In this assay, IgG containing sample was incubated for 24 h with Sepharose-coupled cat extract (0.5 mg) in a total volume of 300 μl in PBS-AT. Subsequently, the Sepharose was washed with PBS-T and incubated for 24 h with $^{125}$I-labeled Bet v 1, after which the Sepharose was washed with PBS-T and the amount of radioactivity bound relative to the amount of radioactivity added was measured. The concentration of bispecific IgG (Feld1-Betv1) was calculated using purified IgG1-Betv1 as a standard (obtained in Bet v 1 binding test using Prot G sepharose).

In FIG. 8 data obtained from the erythrocyte-mediated exchange are presented. No exchange of IgG1 half molecules was observed in the presence of erythocytes, whereas about maximum exchange of IgG4 half molecules was observed after 72 h (panel A) (note: if equal amounts of IgG4-Betv1 and IgG4-Feld1 are exchanged, at most 50% of the IgG4-Betv1 half-antibodies will be incorporated in the bispecific fraction after random and complete exchange of half-antibodies). In the presence of excess irrelevant IgG4 almost no exchange of IgG4 half molecules was measured, which is in line with the expected exchange of Bet v 1 and Fel d 1 specific IgG4 with irrelevant IgG4. Size-exclusion chromatography was performed to exclude the possibility that bispecific activity observed in the IgG4 mix was the result of IgG aggregation. For this purpose, a sample (drawn at t=72 h) was fractionated on a Superdex200 column, after which Fel d 1 binding IgG and Bet v 1-Fel d 1 cross-linking IgG were measured in the fractions. Fel d 1 binding antibodies eluted in one peak with a retention volume of ~12.9 ml, which corresponds to the retention volume of monomeric IgG. The heterologous Bet v 1-Fel d 1 cross-linking activity was detected in the same fractions indicating that bispecific activity was associated with monomeric IgG (data not shown).

In theory, the exchange of IgG4 half molecules is also associated with a decrease in bivalency. To test this, bivalency in the incubation mixtures was measured. Almost no reduction of Fel d 1 bivalency was observed in the IgG1 mix, whereas a reduction of ~50% was observed in the IgG4 mix. This reduction is in agreement with the maximal exchange of two different IgG4 molecules mixed in a 1 to 1 ratio. As expected, the reduction of bivalency in the IgG4 mix with excess irrelevant IgG4 was higher (~80%), which is due to the low probability of rehybridisation of two homologous half molecules (Bet v 1 or Fel dl specific) in the presence of excess irrelevant IgG4 half molecules. The strong reduction in bivalency was not the result of loss of antigen binding during the incubation, because the antigen binding was only slightly (~10%) decreased after 72 h of incubation (data not shown).

Figure 9B:
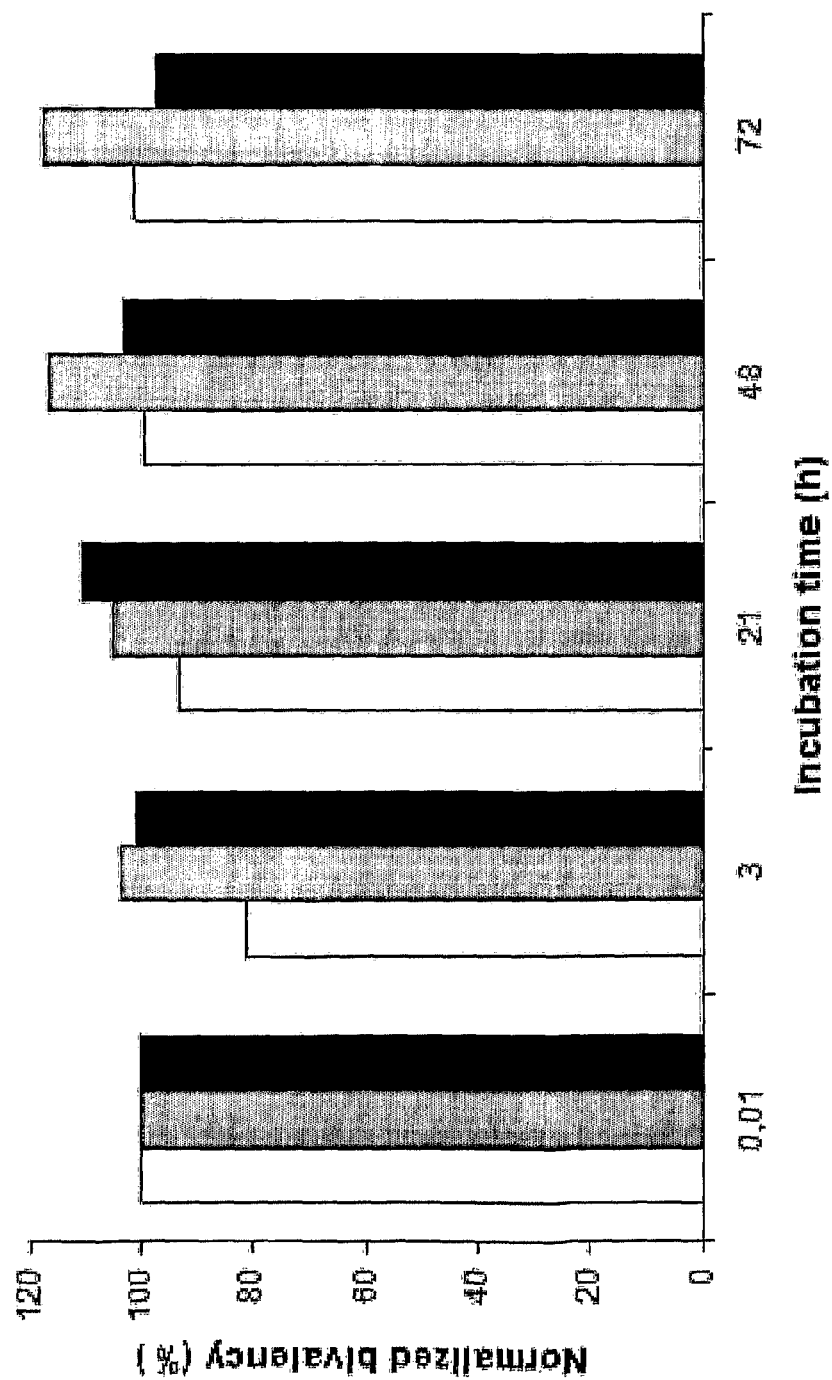

The exchange of IgG in PBS (supplemented with 0.05% (w/v) $NaN_3$) was also evaluated to investigate whether IgG4 half molecules can be exchanged spontaneously. The set-up of this experiment was similar to the exchange in the presence of erythrocytes with the exception that no erythrocytes were added. No spontaneous exchange of IgG1 or IgG4 half molecules was observed during the incubation in PBS at 37° C. as is demonstrated FIG. 9A. However, some background was observed in the IgG4 mix, which was also present during the incubation with erythrocytes. No decrease of bivalency was observed during the incubation in PBS (FIG. 9B).

Example 29

Evaluation of IgG4 Exchange by Erythrocyte Lysate

Chimeric IgG4 antibodies were mixed and subsequently incubated with increasing dilutions of erythrocyte lysate. Erythrocytes were isolated from a healthy donor and stored at 4° C. in SAGM (Saline Adenine Glucose Mannitol) buffer with a hematocrit of 60.7%. To obtain lysate the cells were washed three times with PBS-Azide (PBS supplemented with 0.05% (w/v) $NaN_3$) and resuspended in water with a volume that was two fold higher than the volume of the storage buffer. As a result, undiluted erythrocyte lysate was equivalent to a hematocrit of 30%.

The exchange of IgG4 half molecules was evaluated by incubating an IgG4 antibody mixture consisting of Bet v 1 specific IgG4 (1 μg) and Fel d 1 specific IgG4 (1 μg) with 50 μl of freshly prepared lysate (supplemented with PBS/Azide to a total volume of 100 μl) at 37° C. Final concentration of each antibody was 10 μg/ml. At indicated time points a sample was drawn from the incubation mix in PBS-AT (PBS supplemented with 0.3% bovine serum albumin, 0.1% Tween-20 and 0.05% (w/v) $NaN_3$) to measure bispecific activity. Samples were stored, if necessary, at 4° C.

Bispecific activity (i.e. Bet v 1-Fel d 1 cross-linking activity) was measured in the heterologous cross-linking assay. In this assay, sample dilutions were incubated for 24 h with 0.5 mg Sepharose-coupled birch extract in a total volume of 300

μl in PBS-IAT (PBS-AT supplemented with 1 μg/ml IVIg). Subsequently, the Sepharose was washed with PBS-T and incubated for 24 h with $^{125}$I-labeled Fel d 1, after which the Sepharose was washed with PBS-T and the amount of radioactivity bound relative to the amount of radioactivity added was measured. The concentration of bispecific IgG (Bet v 1-Fel d 1) was calculated using the calibration curve of the Fel d 1 binding test, which was obtained from purified Fel d 1 binding rIgG.

In FIG. 10 generation of bispecific activity in time is shown as percentage bound $^{125}$I-labeled Fel d 1, which was determined in the heterologous cross-linking assay. From these data it is evident that lysate of erythrocytes contains exchange activity. Highest exchange rate was observed in undiluted lysate, whereas higher dilutions resulted in lower exchange rates. Practically no bispecific activity was observed in the control incubation in PBS.

Size-exclusion chromatography was performed to exclude the possibility that bispecific activity induced by erythrocyte lysate was the result of IgG aggregation (FIG. 11). For this purpose, an incubation mixture was prepared consisting of 10 μg Bet v 1 binding IgG4, 10 μg Fel d 1 binding IgG4 and 50 μl erythrocyte lysate, which was supplemented with PBS/Azide to final volume of 100 μl. This mixture was incubated at 37° C. for 24 h, after which 70 μl was fractionated on a Superdex200 column. In the fractions Bet v 1 binding IgG and Fel d 1-Bet v 1 cross-linking IgG were measured. Levels of Bet v 1 binding antibodies were measured in the antigen binding test. Samples were incubated with 0.75 mg of protein G Sepharose (Amersham Biosciences, Uppsala, Sweden) in 750 μl PBS-IAT (PBS supplemented with 1 μg/ml IVIg, 0.3% bovine serum albumin, 0.1% Tween-20 and 0.05% (w/v) $NaN_3$) in the presence of $^{125}$I-labeled Bet v 1 for 24 h. Next, the Sepharose was washed with PBS-T (PBS supplemented with 0.1% Tween-20 and 0.05% (w/v) $NaN_3$) and the amount of radioactivity bound relative to the amount of radioactivity added was measured. The concentration of Bet v 1 specific IgG was calculated using purified Bet v 1 specific antibodies as a standard (range 0-200 ng per test as determined by nephelometer). The concentration of bispecific IgG (i.e. Fel d 1-Bet v 1 cross-linking activity) was measured in the heterologous cross-linking assay. In this assay, a sample was incubated for 24 h with 0.5 mg Sepharose-coupled cat extract, in which Fel d 1 antigen is present, in a total volume of 300 μl in PBS-IAT. Subsequently, the Sepharose was washed with PBS-T and incubated for 24 h with $^{125}$I-labeled Bet v 1, after which the Sepharose was washed with PBS-T and the amount of radioactivity bound relative to the amount of radioactivity added was measured. The concentration of bispecific IgG (Fel d 1-Bet v 1) was calculated using the same calibration curve as used in the Bet v 1 binding test, which was obtained from purified Bet v 1 binding rIgG.

Bet v 1 binding antibodies eluted in one peak with a retention volume of ~12.6 ml, which corresponds to the retention volume of monomeric IgG (FIG. 11). The heterologous Fel d 1-Bet v 1 cross-linking activity was detected in the same fractions indicating that bispecific activity was associated with monomeric IgG.

Example 30

Evaluation of IgG4 Exchange Activity in Dialysed Erythrocyte Lysate

Erythrocytes were isolated from a healthy donor and stored at 4° C. in SAGM (Saline Adenine Glucose Mannitol) buffer with a hematocrit of 60.7%. To obtain lysate the cells were washed three times with PBS-Azide (PBS supplemented with 0.05% (w/v) $NaN_3$) and resuspended in water with a volume that was two-fold higher than the volume of the storage buffer. Therefore, undiluted erythrocyte lysate was equivalent to a hematocrit of 30%. Part of the lysate was dialysed against PBS-Azide using a dialysis membrane cassette from Pierce (3.5 kD cut-off). Ultrafiltrate was obtained by centrifugation of non-dialysed lysate in an Amicon filter (3.5 kD cut-off).

The exchange of IgG4 half molecules was evaluated by incubating an IgG4 antibody mixture (Bet v 1 specific IgG4 (0.5 μg) and Fel d 1 specific IgG4 (0.5 μg) with freshly prepared erythrocyte lysate (25 μl) or dialysed lysate (25 μl) at 37° C. Total volume of each incubation was 50 μl resulting in a final concentration of 10 μg/ml for each antibody. The following supplements were used: reduced glutathione (GSH) from Sigma, Glucose-6-phosphate (G-6-P) and NADPH (both from Roche). These compounds were dissolved in water before use. After 24 h of incubation a sample was drawn from the incubation mix in PBS-AT (PBS supplemented with 0.3% bovine serum albumin, 0.1% Tween-20 and 0.05% (w/v) $NaN_3$) to measure bispecific activity. Samples were stored, if necessary, at 4° C.

Bispecific activity (i.e. Fel d 1-Bet v 1 cross-linking activity) was measured in the heterologous cross-linking assay. In this assay, sample dilutions were incubated for 24 h with 0.5 mg Sepharose-coupled cat extract in a total volume of 300 μl in PBS-IAT (PBS-AT supplemented with 1 μg/ml IVIg). Subsequently, the Sepharose was washed with PBS-T and incubated for 24 h with $^{125}$I-labeled Bet v 1, after which the Sepharose was washed with PBS-T and the amount of radioactivity bound relative to the amount of radioactivity added was measured.

The exchange levels were compared with the bispecific activity generated by freshly prepared lysate (Table 2).

TABLE 2

Overview of factors that restore bispecificactivity in dialysed erythrocyte lysates. Exchange activity of dialysed erythrocyte lysate was compared with freshly prepared lysate. Dialysed lysate was supplemented with 5 □l of ultrafiltrate. Final concentrations of G-6-P, NADPH and GSH and GSH were 5 mM, 0.1 mM and 0.5 mM, respectively.

| Exchange source | Supplement | Exchange activity |
|---|---|---|
| Lysate | – | ++ |
| Dialysed lysate | – | – |
| Dialysed lysate | Ultrafiltrate | + |
| Dialysed lysate | G-6-P, NADPH, GSH | ++ |
| Dialysed lysate | G-6-P | – |
| Dialysed lysate | NADPH | – |
| Dialysed lysate | GSH | ++ |

From these data it is evident that the activity of erythrocyte lysate was lost after dialysis. Addition of ultrafiltrate restored the exchange for a large part. This result suggested that during dialysis a component (<3.5 kD) was lost, which is essential for the exchange reaction. Such a component is likely to be involved in the redox cycle, because disulfide bridge reduction and oxidation is required for the exchange of IgG4 half molecules. Therefore, three "co-factors" (G-6-P, NADPH and GSH) of the redox cycle were added to dialysed lysate to investigate whether these compounds could restore the exchange activity. The exchange activity could be restored if G-6-P, NADPH and GSH were supplemented together. Incubation of dialysed lysate in the presence of separate factors revealed that the exchange activity was restored by GSH, but not by G-6-P or NADPH.

Example 31

Evaluation of IgG4 Half Molecule Exchange by Reduced Glutathione

Chimeric antibodies were mixed and subsequently incubated with reduced glutathione (GSH) to investigate the exchange of IgG4 half molecules. GSH (Sigma-Aldrich, St. Louis, Mo.) was solved in water before use.

In this experiment the exchange of IgG4 half molecules was evaluated by incubating an IgG4 antibody mixture consisting of Bet v 1 specific IgG4 (1 µg) and Fel d 1 specific IgG4 (1 µg) in PBS/Azide containing GSH at 37° C. Total incubation volume was 100 µl resulting in a final concentration of 10 µg/ml for each antibody. At indicated time points a sample was drawn from the incubation mixture in PBS-AT (PBS supplemented with 0.3% bovine serum albumin, 0.1% Tween-20 and 0.05% (w/v) $NaN_3$). Samples were stored at 4° C. for measuring of antigen binding and bispecific activity Levels of Bet v 1 binding antibodies were measured in the antigen binding test. Samples were incubated with 0.75 mg of protein G Sepharose (Amersham Biosciences, Uppsala, Sweden) in 750 µl PBS-IAT (PBS-AT supplemented with 1 µg/ml IVIg) in the presence of $^{125}I$-labeled Bet v 1 for 24 h. Next, the Sepharose was washed with PBS-T (PBS supplemented with 0.1% Tween-20 and 0.05% (w/v) $NaN_3$) and the amount of radioactivity bound relative to the amount of radioactivity added was measured. The concentration of Bet v 1 specific IgG was calculated using purified Bet v 1 specific antibodies as a standard (range 0-200 ng per test as determined by nephelometer). The concentration of bispecific IgG (i.e. Fel d 1-Bet v 1 cross-linking activity) was measured in the heterologous cross-linking assay. In this assay, a sample was incubated for 24 h with 0.5 mg Sepharose-coupled cat extract, in which Fel d 1 antigen is present, in a total volume of 300 µl in PBS-IAT. Subsequently, the Sepharose was washed with PBS-T and incubated for 24 h with $^{125}I$-labeled Bet v 1, after which the Sepharose was washed with PBS-T and the amount of radioactivity bound relative to the amount of radioactivity added was measured. The concentration of bispecific IgG (Fel d 1-Bet v 1) was calculated using the same calibration curve as used in the Bet v 1 binding test, which was obtained from purified Bet v 1 binding IgG.

In FIG. 12 time courses of GSH mediated exchange of IgG4 half molecules are presented. From these data it is clear that IgG4 half molecules are exchanged in the presence of GSH. In this experiment optimal exchange was observed between 0.1 and 1 mM GSH and highest exchange (~90%) was reached after 24 h using 0.5 mM GSH.

Size-exclusion chromatography was performed to exclude the possibility that bispecific activity observed after GSH mediated exchange of IgG4 was the result of IgG aggregation (FIG. 13). For this purpose, a mixture of Bet v 1 binding IgG4 and Fel d 1 binding IgG4 (10 µg of each antibody) was incubated with 0.5 mM GSH in PBS/Azide. This mixture (final volume 100 µl) was incubated at 37° C. for 24 h, after which 70 µl was fractionated on a Superdex200 column. In the fractions Bet v 1 binding IgG and Fel d 1-Bet v 1 cross-linking IgG were measured. Bet v 1 binding antibodies eluted in one peak with a retention volume of ~12.6 ml, which corresponds to the retention volume of monomeric IgG. The heterologous Fel d 1-Bet v 1 cross-linking activity was detected in the same fractions indicating that bispecific activity was associated with monomeric IgG. The generation of bispecific IgG4 molecules in the presence of GSH was found to be temperature dependent, as exchange occurred more efficiently at 37° C. than at 4° C. (FIG. 14).

Example 32

Generation of Bispecific IgG in the Presence of Other Agents

IgG1-Betv1 and IgG1-Feld1 or IgG4-Betv1 and IgG4-Feld1 were mixed at a final concentration of 10 µg/ml for antibody and incubated with reducing agents in a total volume of 50 µl. Apart from GSH the following agents were tested (final concentration in incubation mixture): L-cysteine was from Sigma (100 µM), dithiothreitol (DTT) was from Biorad (50 µM), β-mercapto-ethanol (BME) was from Biorad (100 µM) and oxidized glutathione (GSSG, note that of the panel of agents this agent is not reducing, while all others are) was from Sigma (100 µM). The mixtures were incubated at 37° C. for 24 h and samples were drawn in PBS/AT, in which the (bi)specific IgG concentrations were measured. FIG. 15 shows that the addition of GSH or other reducing agents (but not of GSSG) to a mixture of purified IgG4-Betv1 and IgG4-Feld1 was sufficient to induce Fab arm exchange and the generation of bispecific IgG4. In contrast, no bispecific reactivity was induced in the control IgG1 mixture.

Example 33

Exchange of Fully Human IgG4 Antibodies Using GSH

IgG1-CD20, IgG4-CD20, IgG1-EGFr and IgG4-EGFr were mixed and incubated with GSH in a total volume of 1 ml. Final concentration of each antibody was 50 µg/ml; the final concentration of GSH was 0.5 mM. The mixtures were incubated at 37° C. for 24 h and samples were drawn in PBS-AT, in which the (bi)specific IgG concentrations were measured.

Bispecific activity was determined using a sandwich ELISA. For this assay an ELISA plate (Greiner bio-one, Frickenhausen, Germany) was coated overnight with 1 µg/ml (100 µl/well) of recombinant extracellular domain of EGFR in PBS at 4° C. The plate was washed 3 times with PBS/0.05% Tween 20 (PBT). Samples were diluted in PBT/0.2% BSA (PBTB) and transferred to the ELISA plate (100 µl/well). After incubation on a plate shaker (300 rpm) for 90 minutes at room temperature (RT), samples were discarded and the plate was washed 3 times with PBT. Next, 100 µl of the mouse anti-idiotypic monoclonal antibody 2F2 SAB1.1 (directed against the anti-CD20 antibody 7D8; Genmab) at 2 µg/ml in PBTB was added and incubated at RT for 90 minutes at a plate shaker (300 rpm). The anti-idiotypic antibody was discarded and the plate was washed 3 times with PBT, followed by the addition of 100 µl/well of a HRP conjugated goat anti-mouse IgG (Jackson ImmunoResearch Laboratories, Westgrove, Pa., USA) at a 1000× dilution in PBTB and incubation at RT for 90 minutes at a plate shaker (300 rpm). The detection antibody was discarded and the plate was washed 3 times with PBT. A 50 mg ABTS tablet (Roche Diagnostics GmbH, Mannheim, Germany) was dissolved in ABTS buffer (Roche) and added to the ELISA plate (100 µl/well). The ELISA plate was incubated for 30 min (or longer if desired) at RT on a plate shaker (300 rpm) covered with aluminum foil and the reaction was stopped with 100 µl oxalic acid (Riedel de Haen Seelze, Germany) per well. The ELISA plate was left at RT for 10 minutes before reading absorbance at 405 nm in an ELISA plate reader.

Figure 16A:
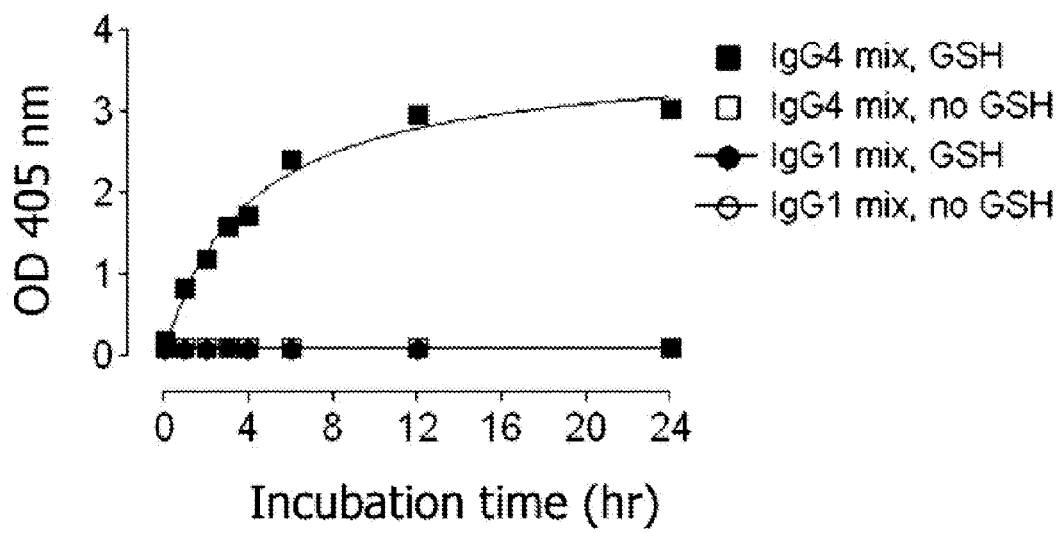

FIG. 16A shows that bispecific anti-EGFR/CD20 antibodies formed in time upon incubation of the mixture of IgG4-EGFr and IgG4-CD20 in the presence, but not in the absence, of GSH. Fab arm exchange did not occur in a mixture of IgG1 antibodies, neither in the presence or absence of GSH.

Figure 16B:
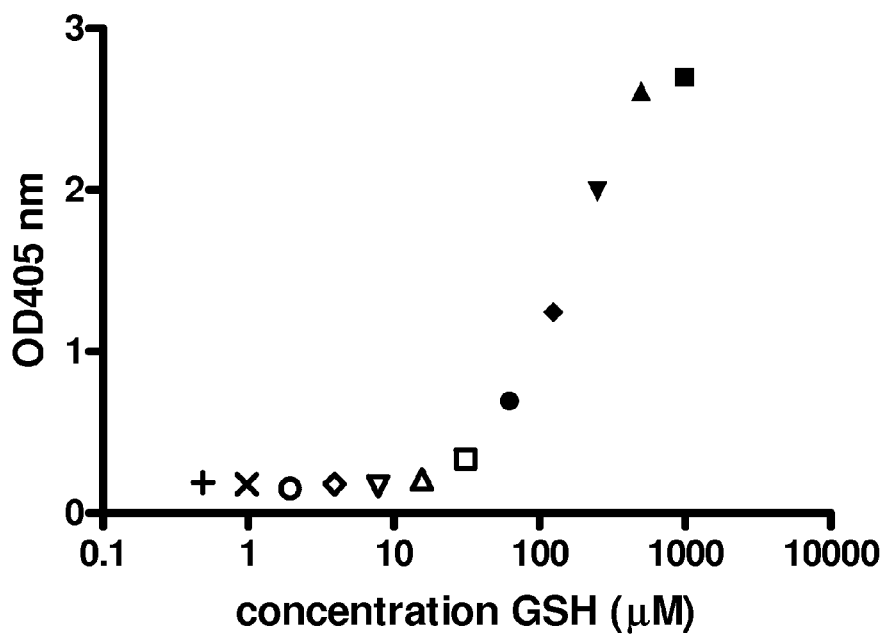

To explore the dynamic range of GSH mediated exchange of IgG4 half molecules, a full concentration curve of GSH (0.5-1,000 NM) was used to analyze exchange. IgG4-CD20 and IgG4-EGFr were mixed and incubated with GSH in a total volume of 1 ml. Final concentration of each antibody was 50 µg/ml; the final concentration of GSH were as indicated in FIG. 16B. The mixtures were incubated at 37° C. for 24 h and samples were drawn in PBS-AT, in which the (bi) specific IgG concentrations were measured.

Figure 16C:
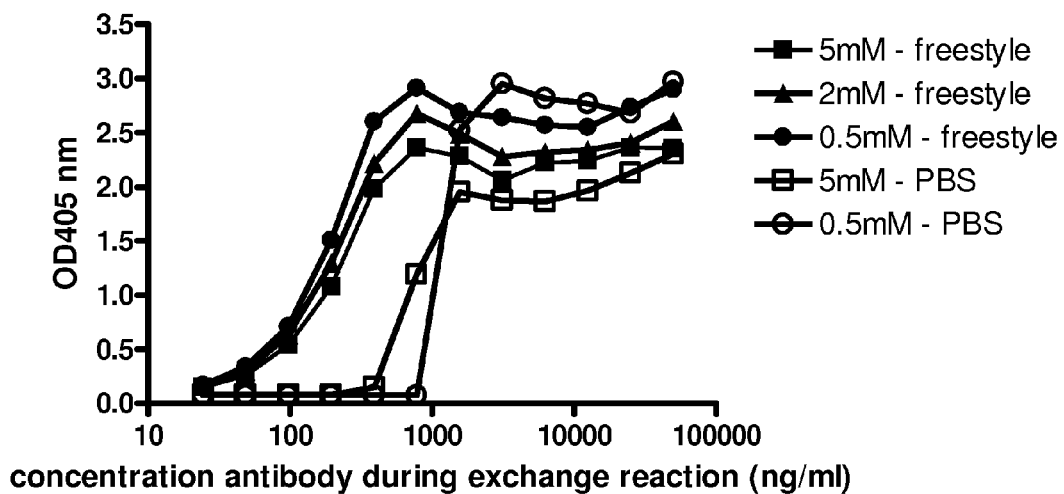
Figure 16D:
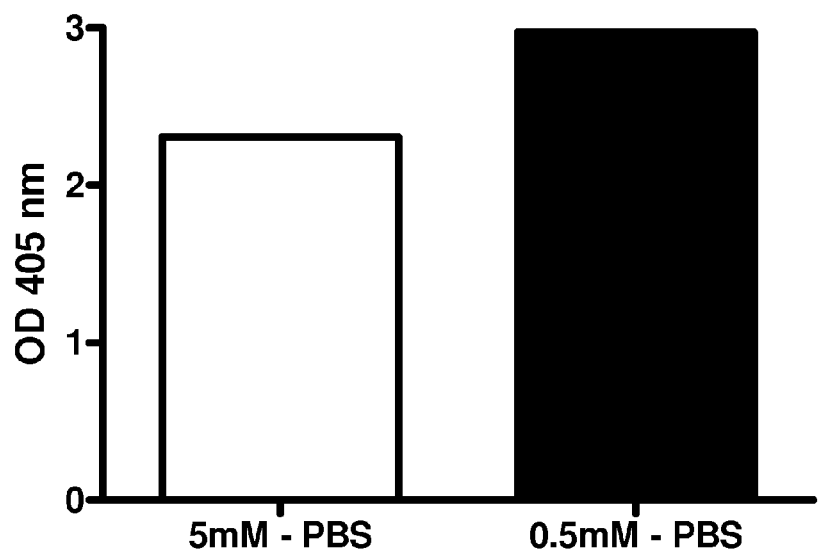

FIG. 16B shows a clear GSH-dose dependence of IgG4 half molecule exchange. To explore how reaction components influence the GSH-mediated IgG4 half molecule exchange, exchange was tested in PBS and serum- and protein free, chemically defined medium (FreeStyle 293 expression medium, GIBCO/Invitrogen Corporation). It was found that in this tissue culture medium, GSH-mediated exchange occurs at lower GSH-concentrations (FIG. 16C). It was also found that there is an optimum in GSH-mediated IgG4 half molecule exchange, as incubation with 5 mM GSH clearly resulted in lower exchange that with 0.5 mM (FIG. 16D).

A mixture of IgG4-EGFr and IgG4-CD20 was incubated for 24 h in the absence or presence of GSH and evaluated by mass spectrometry (ESI-TOF MS). Fifty µl samples containing 200 µg/ml of each antibody were deglycosylated overnight with 1 µl N-glycosidase F (Roche Diagnostics NL BV, Almere, The Netherlands). Samples were desalted on an Acquity HPLC™ (Waters, Milford, USA) with a BEH C8, 1.7 µm, 2.1×50 mm column at 60° C. Five µl was injected and eluted with a gradient from 5% to 95% eluent B. Eluent A was MilliQ water (Millipore Synthesis A10 apparatus) and eluent B was LC-MS grade acetonitrile (Biosolve, Valkenswaard, The Netherlands). Both eluents contained 0.05% formic acid as organic modifier (Fluka Riedel-de Haan, Buchs, Germany). Time-of-flight electrospray ionization mass spectra were recorded on-line on a micrOTOF™ mass spectrometer (Bruker, Bremen, Germany) operating in the positive ion mode. In each analysis, a 500-5000 m/z scale was internally calibrated with ES tuning mix (Agilent Technologies, Santa Clara, USA). Mass spectra were deconvoluted by using the Maximum Entropy algorithm, which is provided with DataAnalysis™ software v. 3.3 (Bruker).

Figure 16E:
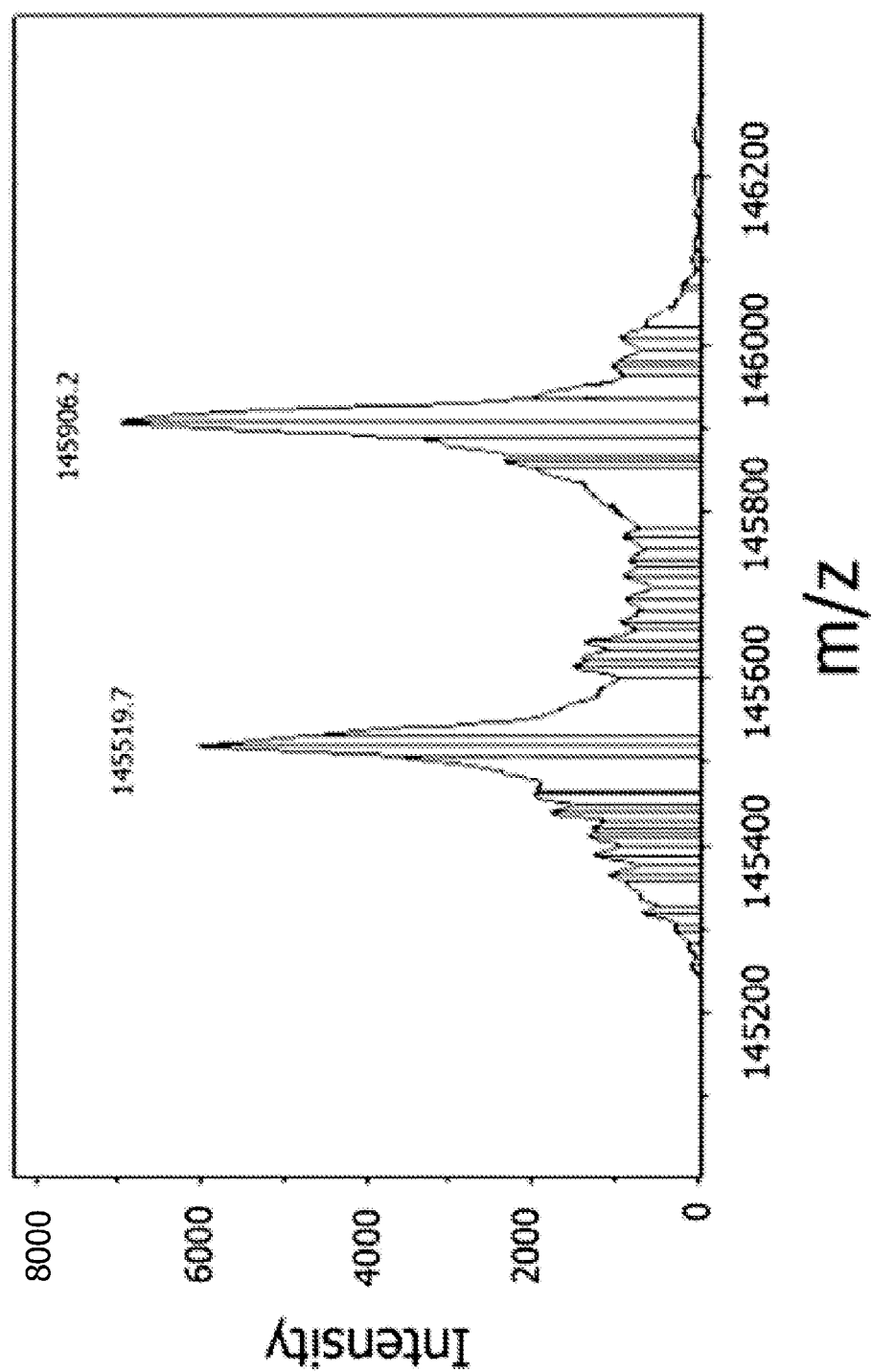
Figure 16F:
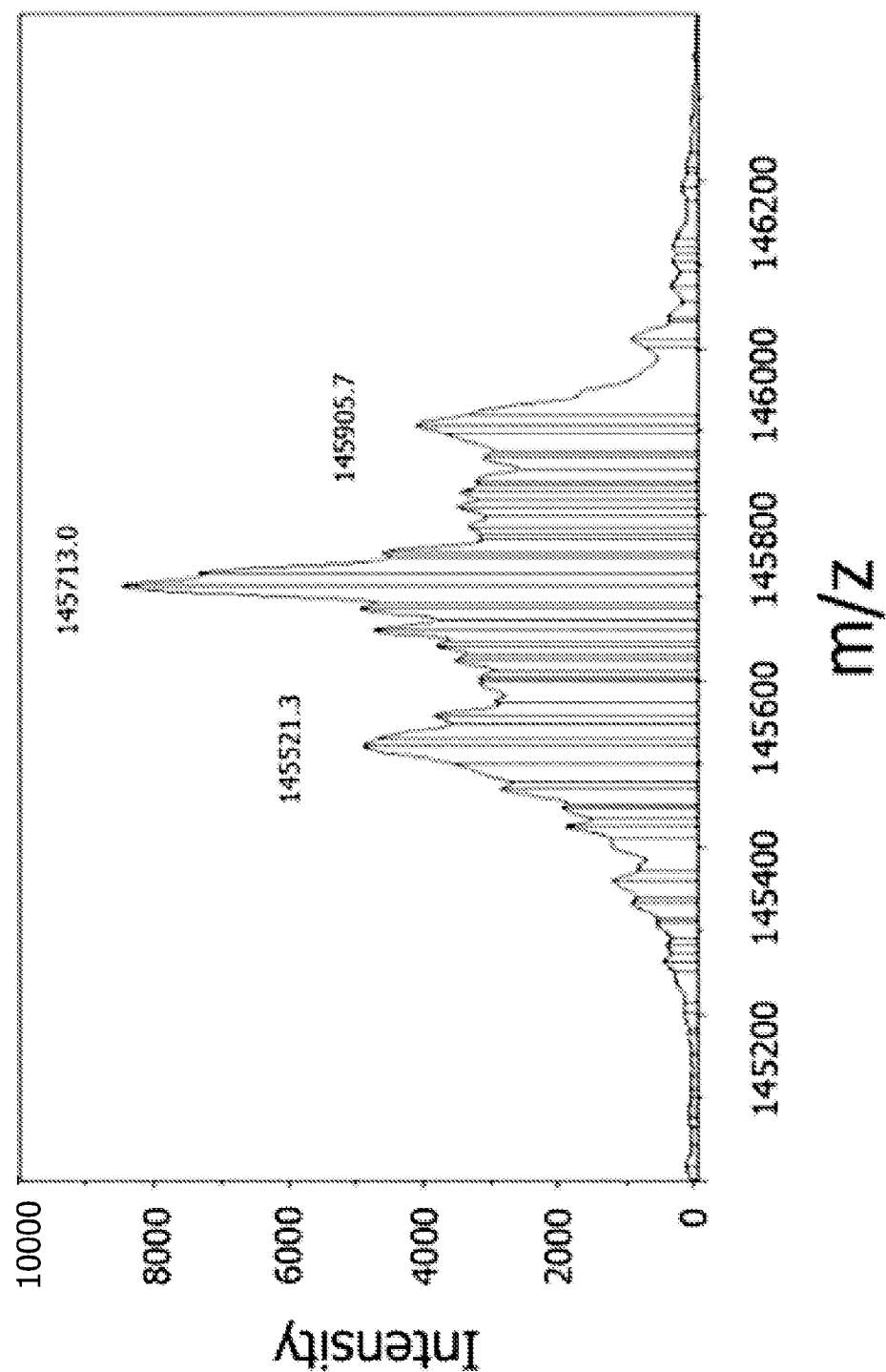

FIG. 16E shows that the molecular weights of IgG4-CD20 (145.5 kD) and IgG4-EGFR (145.9 kD) remained unchanged in the absence of GSH. In the presence of GSH (FIG. 16F), however, a new peak with a mass corresponding to a Fab arm exchanged molecule appeared (145.7 kD). The novel mass corresponded to the expected mass of the bispecific anti-EGFR/CD20 antibody. Moreover, from the peak heights of the MS spectra it could be estimated that the bispecific antibody represented 50% of the total antibody mass in the mixture indicating a random exchange which reached equilibrium within 24 hours.

Example 34

Polyclonal Immunoglobulins from Rhesus Monkey (and Other Species) Participate in Fab Arm Exchange of Recombinant Human IgG4 Antibodies Mixtures of two recombinant human IgG4 antibodies (IgG4-CD20 and IgG4-EGFr, as described above) were incubated with GSH for 24 h at 37° C., in the presence or absence of purified immunoglobulins from rhesus monkeys (6×), chimpanzees (2×), cynomolgus monkeys, Baboons, horse and swine or human IVIg. The formation of bispecific antibodies through Fab arm exchange was measured in a sandwich ELISA as described above. Additionally, goat, rabbit and sheep immunoglobulins were tested in this assay.

Figure 17A:
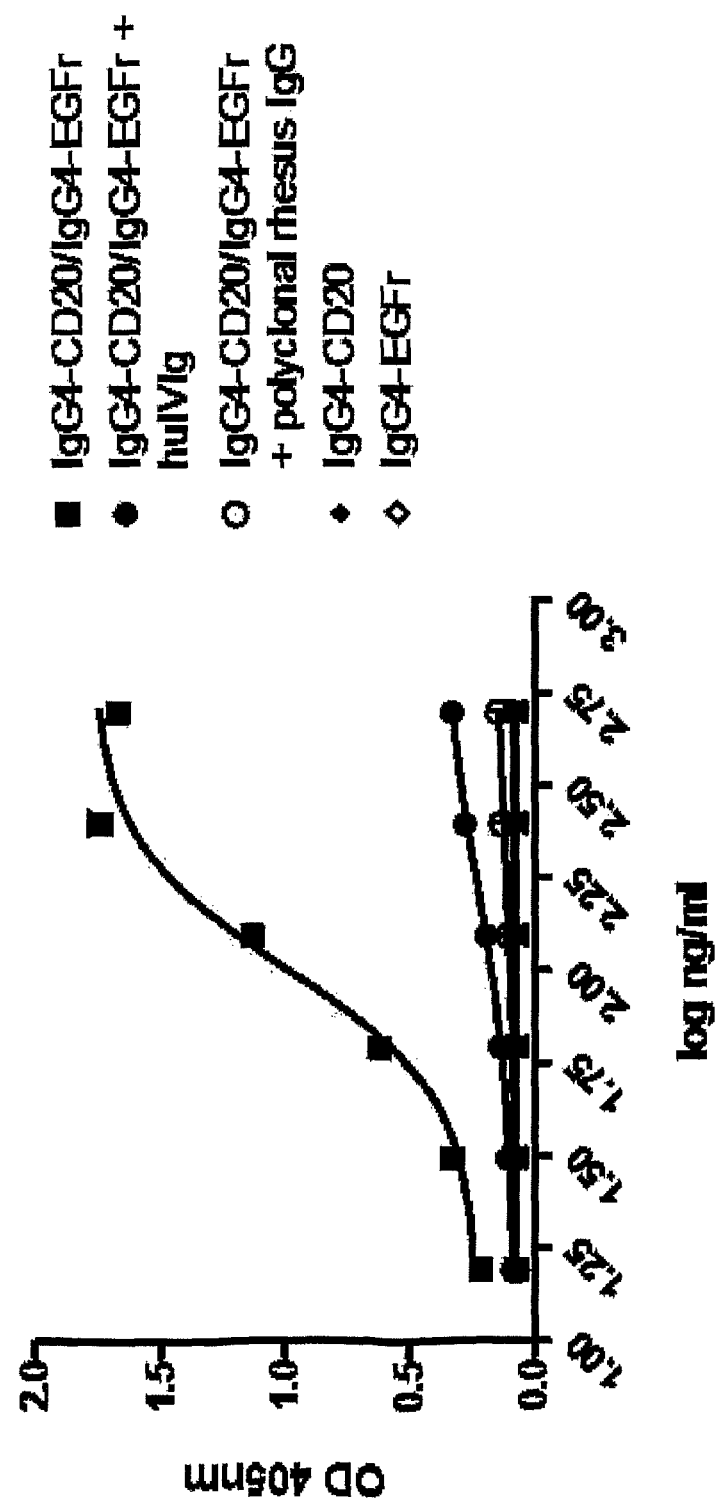

FIG. 17a shows that rhesus monkey polyclonal immunoglobulins compare to human polyclonal immunoglobulins (IVIg) in their ability to inhibit the exchange of Fab arms of the recombinant antibodies in vitro in the presence of reduced glutathione. This means that a component of rhesus immunoglobulin, participates in Fab arm exchange. Rhesus immunoglobulin, presumably rhesus IgG4, can exchange Fab arm with recombinant human IgG4.

Figure 17B:
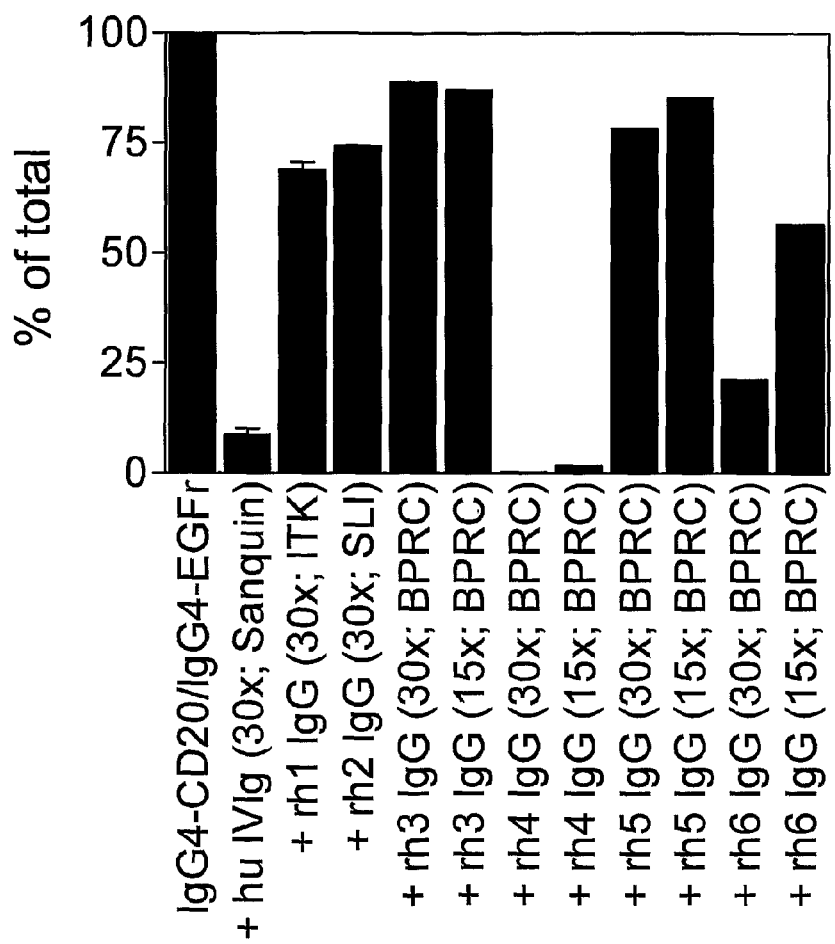

FIG. 17b shows that polyclonal immunoglobulins from several other rhesus monkeys inhibit the exchange of Fab arms of the recombinant antibodies in vitro in the presence of reduced glutathione with different potencies. This means that the component of rhesus immunoglobulin that participates in Fab arm exchange, is present in different concentrations or that the component is not present in all Rhesus monkeys.

Figure 17C:
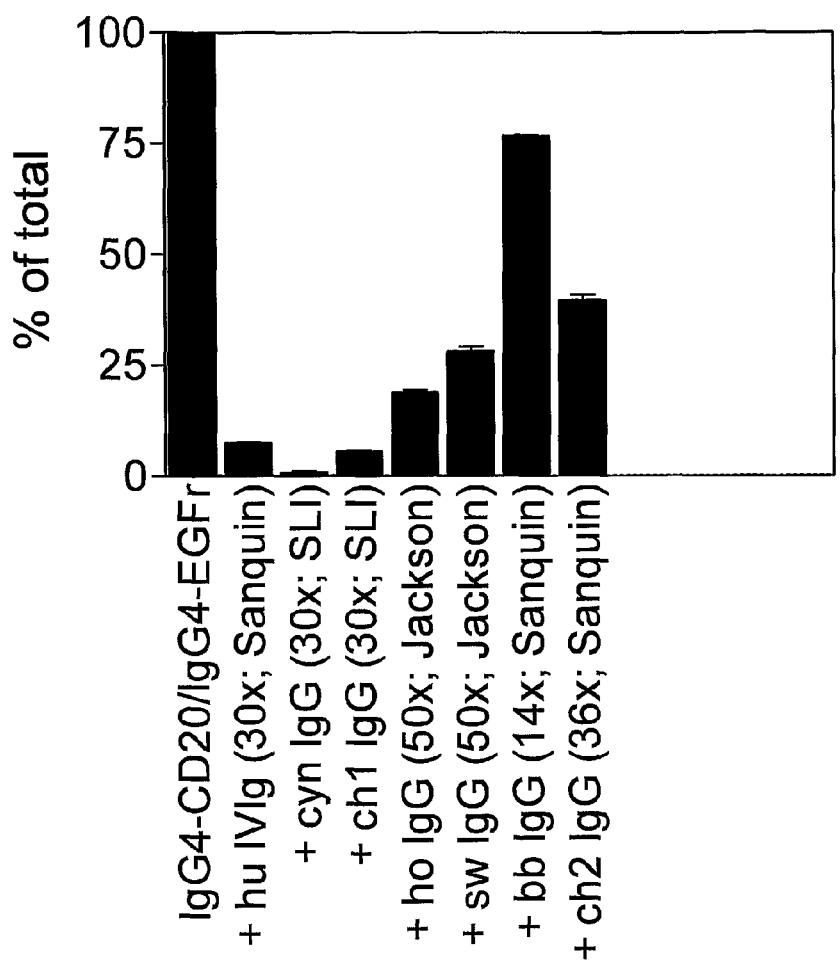

FIG. 17c shows that polyclonal immunoglobulins from several other monkey species (baboon, chimpanzee, cynomolgous) as well as immunoglobulins from horse and swine inhibit the exchange of Fab arms of the recombinant antibodies in vitro in the presence of reduced glutathione with different potencies. This means that the component that participates in Fab arm exchange is present in these species at different concentrations. Goat, rabbit and sheep immunoglobulins had no effect on the exchange of Fab arms of the recombinant antibodies in vitro in the presence of reduced glutathione (data not shown).

Example 35

Half Molecule Exchange of Hinge Region or CH3 Domain Mutants

Three IgG1 mutants were made: an IgG1 with an IgG4 core-hinge (IgG1-CPSC) and two CH3 domain swap mutants (IgG1-CH3(IgG4) and IgG1-CPSC-CH3(IgG4).

Site directed mutagenesis was used to introduce a P228S mutation in the hinge of IgG1 using pEE-G1-wt a Bet v 1 as a template (228 refers to the EU numbering of antibody amino acid residues. The same position has number 241 in the Kabat numbering, and number 111 in SEQ ID NO:19 (third position in the CPPC core-hinge sequence)). Mutagenic primers, forward and reverse, were designed with Vector NTI Advance 10:

P228S Mut primer-F: SEQ ID NO: 23

P228S Mut primer-R: SEQ ID NO: 24

P228S Mut primer-F
5'-CTTgTgACAAAACTCACACCTgCCCATCgTgCCCAggTAAgCCA
g-3'

P228S Mut primer-R
5'-CTggCTTACCTgggCACgATgggCAggTgTgAgTTTTgTCACAA
g-3'

Quickchange site-directed mutagenesis kit (Stratagene) was used to create the pEE-G1-CPSC mutant. The polymerase chain reaction (PCR) mix consisted of 5 µl pEE-G1 a Betv1 DNA template (~35 ng), 1.5 µl mutagenic primer-forward (~150 ng), 1.5 µl mutagenic primer-reverse (~150 ng), 1 µl dNTP mix, 5 µl reaction buffer (10×), 36 µl H2O and finally 1 µl Pfu Turbo DNA polymerase. Then the mix was applied to the PCR: 30" 95° C., 30" 95° C. (denaturating), 1' 55° C. (annealing) and 17 minutes 68° C. (elongating). This cycle was repeated 20 times.

DNA digesting and ligation was used to create CH3 domain swap mutant constructs IgG1-CH3(IgG4) and IgG1-CPSC-CH3(IgG4). Digestion reactions to obtain CH3 domains and vectors without CH3 domains were as follows: ~1500 ng DNA (pEE-G1-betv1, pEE-G1-CPSC and pEE-G4-betv1), 2 μl BSA, 2 μl Neb3 buffer, 1 μl SalI and H$_2$O added to a volume of 20 μl. Incubation at 37° C. for 30'. DNA was purified and eluted with 30 μl H$_2$O before 1 μl SanDI and 3 μl universal buffer was added and incubated at 37° C. for 30'. Fragments were subjected to gel electrophoresis on 1% agarose gels with ethidium bromide. Fragments were cut from the gel under ultraviolet light and dissolved using a DNA purification kit (Amersham). The pEE-G4-wt SalI/SanDI (which contained IgG4 CH3 domain) fragment was ligated into pEE-G1-wt and pEE-G1-CPSC using following procedure: 1 μl template DNA (SalI/SanDI digested pEE-G1-wt and pEE-G1-CPSC), 5 μl SalI/SanDI insert, 4 μl Ligate-it buffer, 9 μl H$_2$O and 1 μl ligase in a total volume of 20 μl. Ligation was stopped after 5'.

DNA digestion (using ApaI and HindIII) and ligation was used to replace the VH domain of the bet v 1 mutant antibodies with that of pEE-G4-a-feld1 wt, following a similar procedure as above.

Also, one IgG4 mutant was made: IgG4-S228Pnew. In this mutant, the hinge is stabilized by replacing serine at position 228 (position 111 in SEQ ID NO:19) for a proline (IgG1 core hinge). Site-directed mutagenesis was performed using the QuickChange II XL Site-Directed Mutagenesis Kit (Stratagene, Amsterdam, The Netherlands) according to the manufacturer's instructions. This method included the introduction of a silent extra XmaI site to screen for successful mutagenesis. Briefly, 5 μl 10× reaction buffer, 1 μl oligonucleotide S228Pfcorrect (100 pmol/μl), 1 μl oligonucleotide S228Prcorrect (100 pmol/μl), 1 μl dNTP mix, 3 μl Quicksolution, 1 μl plasmid pTomG42F8HG (50 ng/μl) (described in PCT application entitled "Recombinant monovalent antibodies and methods for production thereof", filed on 28 Nov. 2006 (RO/DK (Genmab)) and 1 μl PfuUltra HF DNA polymerase were mixed in a total volume of 50 μl and amplified with a TGradient Thermocycler 96 (Whatman Biometra, Goettingen, Germany; product # 050-801) using an 18-cycle program: denaturing at 95° C. for 1 min; 18 cycles of 95° C. for 50 sec, 60° C. for 50 sec, and 68° C. for 10 min. PCR mixtures were stored at 4° C. until further processing. Next, PCR mixtures were incubated with 1 μl DpnI for 60 min at 37° C. to digest the pTomG42F8HG vector and stored at 4° C. until further processing. The reaction mixture was precipitated with 5 μl 3 M NaAc and 125 μl Ethanol, incubated for 20 minutes at −20° C. and spun down for 20 minutes at 4° C. at 14000×g. The DNA pellet was washed with 70% ethanol, dried and dissolved in 4 μl water. The total 4 μl reaction volume was transformed in One Shot DNH5α T1$^R$ competent E. coli cells (Invitrogen, Breda, The Netherlands) according to the manufacturer's instructions (Invitrogen). Next, cells were plated on Luria-Bertani (LB) agar plates containing 50 μg/ml ampicillin. Plates were incubated for 16-18 hours at 37° C. until bacterial colonies became evident.

After screening by colony PCR and XmaI (mutagenesis will result in the loss of a XmaI site) digestion, plasmid was isolated from the bacteria and the mutation was confirmed by DNA sequencing. To check if no unwanted extra mutations were introduced the whole HC coding region was sequenced and did not contain any additional mutations. The final construct was named pTomG42F8S228PNew.

| Name | Oligo Sequence |
|---|---|
| S228Pfcorrect (SEQ ID NO: 25) | CCCCCATGCCCACCATGCCCAGGTAAGCCAACCC AGGCCTCGC |
| S228Prcorrect (SEQ ID NO: 26) | GCGAGGCCTGGGTTGGCTTACCTGGGCATGGTGG GCATGGGGG |

Recombinant antibodies from these constructs were transiently expressed in HEK 293 cells in 3 ml, 6-wells plates (NUNC) or in 125 ml erlenmeyers (Corning) with 293 Fectin (Invitrogen) as transfection reagent.

The following mixtures of unpurified antibodies (FreeStyle 293 expression medium, GIBCO/Invitrogen Corporation) were incubated with 0.1 mM GSH at 37° C. for 24 h and samples were drawn in PBS-AT, in which the (bi)specific IgG concentrations were measured as described in previous examples:

IgG4 a-feld1 wt with IgG4 a-betv1 wt
IgG1 a-feld1 wt with IgG4 a-betv1 wt
IgG1 a-feld1 CPSC with IgG1 a-betv1 CPSC (indicated as IgG1 CPSC-IgG1 CPSC below)
IgG1 a-feld1 CPSC with IgG1 a-betv1 CH3(IgG4) (IgG1 CPSC-IgG1 CH3(IgG4))
IgG1 a-feld1 CPSC with IgG1 a-betv1 CPSC/CH3(IgG4) (IgG1 CPSC-IgG1 CPSC/CH3(IgG4))
IgG1 a-feld1 CH3(IgG4) with IgG1 a-betv1 CH3(IgG4) (IgG1 CH3(IgG4)-IgG1 CH3(IgG4))
IgG1 a-feld1 CH3(IgG4) with IgG1 a-betv1 CPSC/CH3 (IgG4) (IgG1 CH3(IgG4)-IgG1 CPSC/CH3(IgG4))
IgG1 a-feld1 CPSC/CH3(IgG4) with a-betv1 IgG1 CPSC/CH3(IgG4) (IgG1 CPSC/CH3(IgG4)-IgG1 CPSC/CH3 (IgG4))
IgG1 a-feld1 CPSC/CH3(IgG4) with IgG4 a-betv1 wt (IgG1 CPSC/CH3(IgG4)-IgG4 wt)
IgG4 a-bet1 S228Pnew with IgG4 wt The results showed that under these in vitro conditions (0.1 mM GSH), half molecule exchange occurs when one of the antibodies contains the CPSC (SEQ ID NO: 29) hinge and both antibodies contain an IgG4-like CH3. Also, half molecule exchange occurs between an IgG4 molecule containing an IgG1 hinge and IgG4 wt molecules:

|  | IgG1 wt | IgG4 wt | IgG1 CH3(IgG4) | IgG1 CPSC | IgG1 CPSC/CH3 (IgG4) |
|---|---|---|---|---|---|
| IgG1 wt | − | − |  |  |  |
| IgG4 wt | − | + | + | − | + |
| IgG1 CH3(IgG4) |  | + | − | − | ± |
| IgG1 CPSC | − | − | − | − |  |
| IgG1 CPSC/CH3(IgG4) |  | + | ± | − | + |
| IgG4 S228Pnew | − | + |  |  |  |

− = no exchange
+ = exchange occurs
± = limited exchange (~5%)
Blank square = not tested The effect of GSH concentration on the half molecule exchange from the different mutants was tested using 0, 0.1, 1 and 10 mM GSH. Exchange was tested using the following mixtures:

IgG4 a-feld1 wt with IgG4 a-betv1 wt
IgG1 a-feld1 wt with IgG4 a-betv1 wt
IgG1 a-feld1 CPSC with IgG1 a-betv1 CPSC IgG1 a-feld1 CH3(IgG4) with IgG1 a-betv1 CH3(IgG4)
IgG1 a-feld1 CPSC/CH3(IgG4) with a-betv1 IgG1 CPSC/CH3(IgG4))

For GSH concentrations up to 1 mM, the results (FIG. 19A) confirmed those described above. At 10 mM GSH, half molecule exchange was also seen in the reaction containing IgG1 a-feld1 CH3(IgG4) and IgG1 a-betv1 CH3(IgG4).

Size-exclusion chromatography was performed to exclude the possibility that bispecific activity observed after GSH mediated exchange of the appropriate IgG1 mutants was the result of IgG aggregation as described in previous examples. The heterologous Fel d 1-Bet v 1 cross-linking activity was detected in the fractions corresponding to the retention volume of monomeric IgG.

Figure 19B:
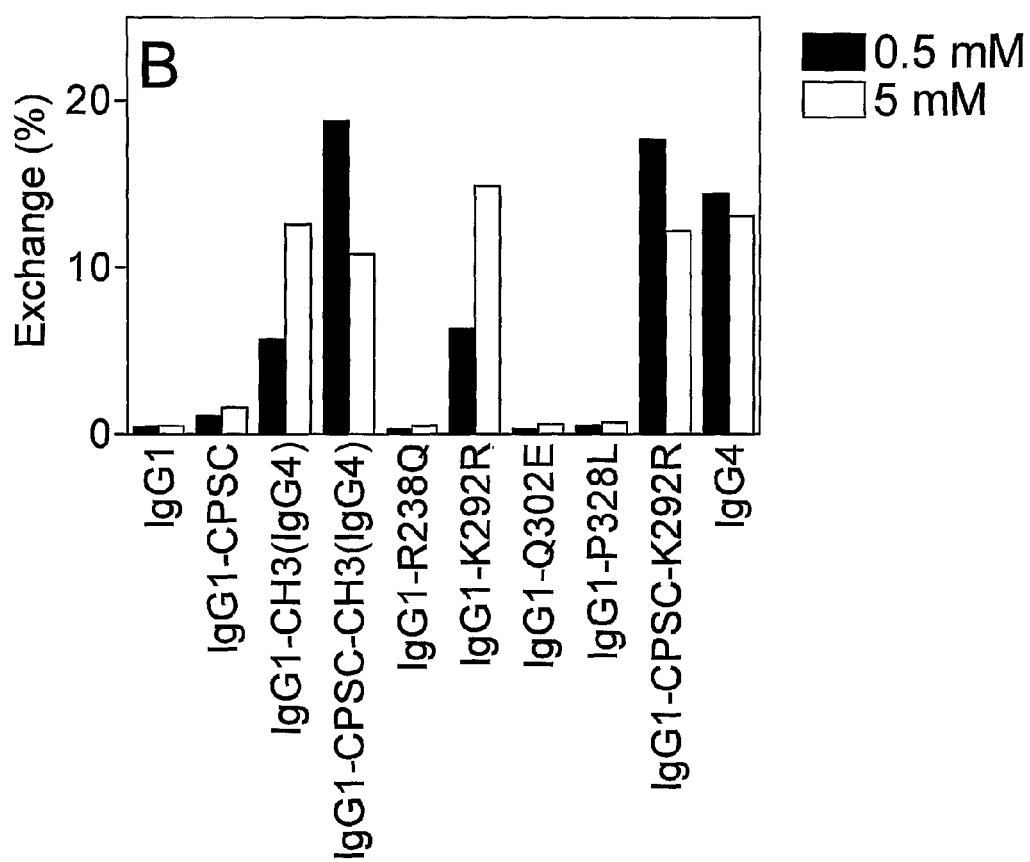
Figure 19C:
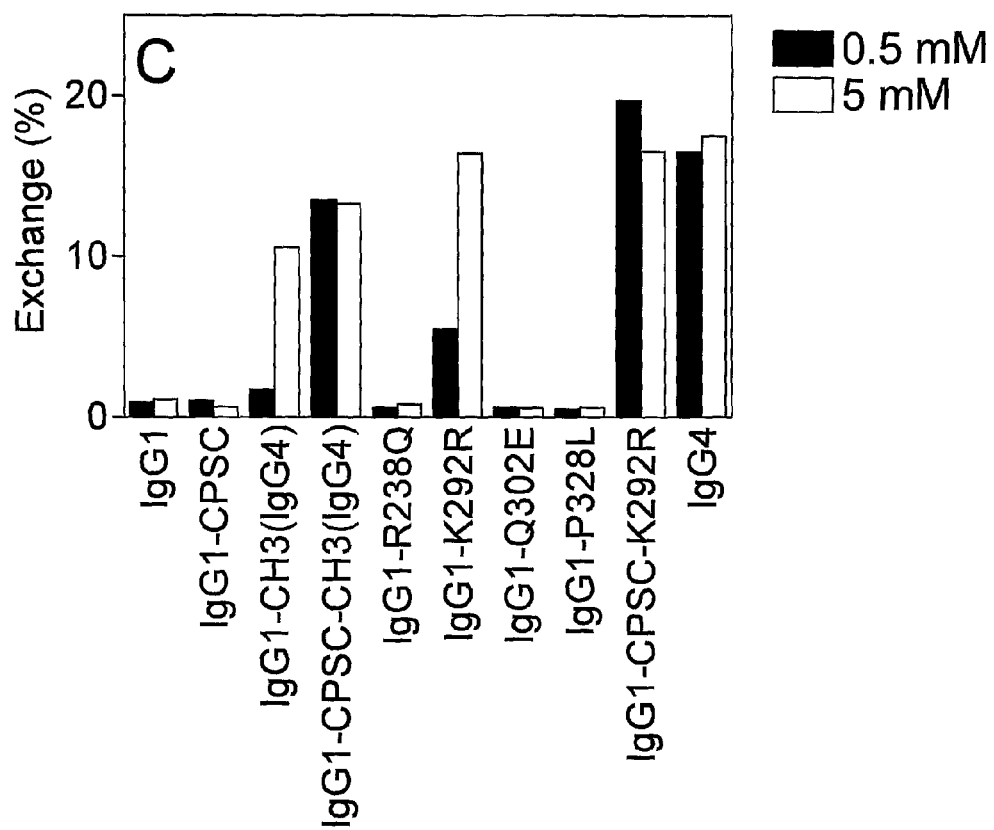

To identify amino-acid residues in the CH3 domain responsible for the ability to exchange half-molecules, IgG4-like residues were introduced into the CH3 of IgG1 at positions that differ between IgG1 and IgG4. Thus R238Q, K292R, Q302E or P328L mutations (numbers refer to SEQ ID NO:19) were introduced in the CH3 domain of IgG1 using pEE-G1-wt a Bet v 1 or pEE-G1-wt a Fel d 1 as a template, basically as described above. Moreover a K292R mutation was also introduced into the CH3 domain of IgG1 CPSC using the pEE-G1-CPSC betv1 or pEE-G1-CPSC feld1 as a template. In short, mutagenic primers, forward and reverse, were designed with Vector NTI Advance 10. Quickchange site-directed mutagenesis kit (Stratagene) was used to create the constructs. Recombinant antibodies from these constructs were transiently expressed in HEK 293 cells in 3 ml, 6-wells plates (NUNC) or in 125 ml erlenmeyers (Corning) with 293 Fectin (Invitrogen) as transfection reagent. The following mixtures of unpurified antibodies (FreeStyle 293 expression medium, GIBCO/Invitrogen Corporation) were incubated with 0.5 or 5 mM GSH at 37° C. for 24 h and samples were drawn in PBS-AT, in which the (bi)specific IgG concentrations were measured as described in previous examples:

IgG1 a-feld1 wt with IgG4 a-betv1 wt (indicated as IgG1 in FIG. 19B)
IgG1 a-feld1 CPSC with IgG4 a-betv1 wt (indicated as IgG1-CPSC in FIG. 19B)
IgG1 a-feld1 CH3(IgG4) with IgG4 a-betv1 wt (indicated as IgG1-CH3(G4) in FIG. 19B)
IgG1 a-feld1 CPSC/CH3(IgG4) with IgG4 a-betv1 wt (indicated as IgG1-CPSC/CH3(G4) in FIG. 19B)
IgG1 a-feld1 R238Q with IgG4 a-betv1 wt (indicated as IgG1-R238Q in FIG. 19B)
IgG1 a-feld1 K292R with IgG4 a-betv1 wt (indicated as IgG1-K292R in FIG. 19B)
IgG1 a-feld1 Q302E with IgG4 a-betv1 wt (indicated as IgG1-Q302E in FIG. 19B)
IgG1 a-feld1 P328L with IgG4 a-betv1 wt (indicated as IgG1-P328L in FIG. 19B)
IgG1 a-feld1 CPSC/K292R with IgG4 a-betv1 wt (indicated as IgG1-CPSC/K292R in FIG. 19B)
IgG4 a-feld1 wt with IgG4 a-betv1 wt (indicated as IgG4 in FIG. 19B)
IgG1 a-feld1 wt with IgG1 a-betv1 wt (indicated as IgG1 in FIG. 19C)
IgG1 a-feld1 CPSC with IgG1 a-betv1 CPSC (indicated as IgG1-CPSC in FIG. 19C)
IgG1 a-feld1 CH3(IgG4) with IgG1 a-betv1 CH3(IgG4) (indicated as IgG1-CH3(G4) in FIG. 19C)
IgG1 a-feld1 CPSC/CH3(IgG4) with IgG1 a-betv1 CPSC/CH3(IgG4) (indicated as IgG1-CPSC/CH3(G4) in FIG. 19C)
IgG1 a-feld1 R238Q with IgG1 a-betv1 R238Q (indicated as IgG1-R238Q in FIG. 19C)
IgG1 a-feld1 K292R with IgG1 a-betv1 K292R (indicated as IgG1-K292R in FIG. 19C)
IgG1 a-feld1 Q302E with IgG1 a-betv1 Q302E (indicated as IgG1-Q302E in FIG. 19C)
IgG1 a-feld1 P328L with IgG1 a-betv1 P328L (indicated as IgG1-P328L in FIG. 19C)
IgG1 a-feld1 CPSC/K292R with IgG1 a-betv1 CPSC/K292R (indicated as IgG1-CPSC/K292R in FIG. 19C)
IgG4 a-feld1 wt with IgG4 a-betv1 wt (indicated as IgG4 in FIG. 19C)

The results showed that under the tested in vitro conditions (0.5 mM and 5 mM GSH), half molecule exchange occurs when both antibodies contain an R at position 292 (FIG. 19B+C). An R or Q at position 238, an Q or E at position 302 and a P or L at position 328 do not influence the inability of and IgG1 to exchange half molecules in this experimental set up.

Example 36

At 0.5 mM GSH, IgG4 Molecules with a Stabilized, IgG1-Like Core-Hinge do not Participate in Fab-Arm Exchange Reaction of Recombinant Human IgG4 Antibodies Mixtures of two recombinant human IgG4 antibodies (IgG4-CD20 and IgG4-EGFr, as described above) were incubated with 0.5 mM GSH for 24 h at 37° C., in the presence or absence of an excess (10, 50 and 100 micrograms/ml) of Tysabri or (10 micrograms/ml) of Mylotarg. Tysabri is a commercially available humanized IgG4 antibody containing a wild-type IgG4 core-hinge, while Mylotarg is a commercially available humanized IgG4 antibody containing a stabilized, IgG1-like core-hinge. The formation of bispecific antibodies through Fab-arm exchange was measured in a sandwich ELISA as described above.

Figure 20A:
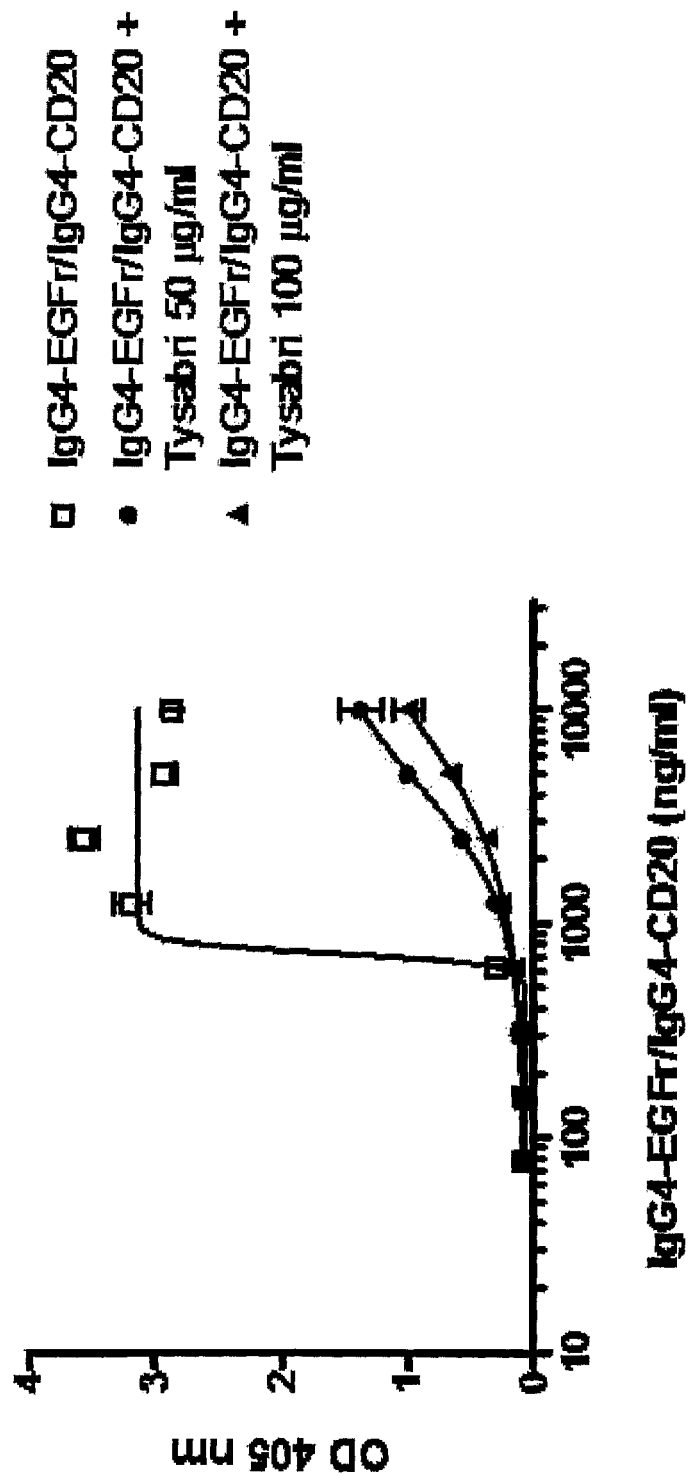

FIG. 20A shows that in the presence of an excess of Tysabri exchange of Fab arms of the recombinant CD20 and EGFr antibodies was inhibited.

Figure 20B:
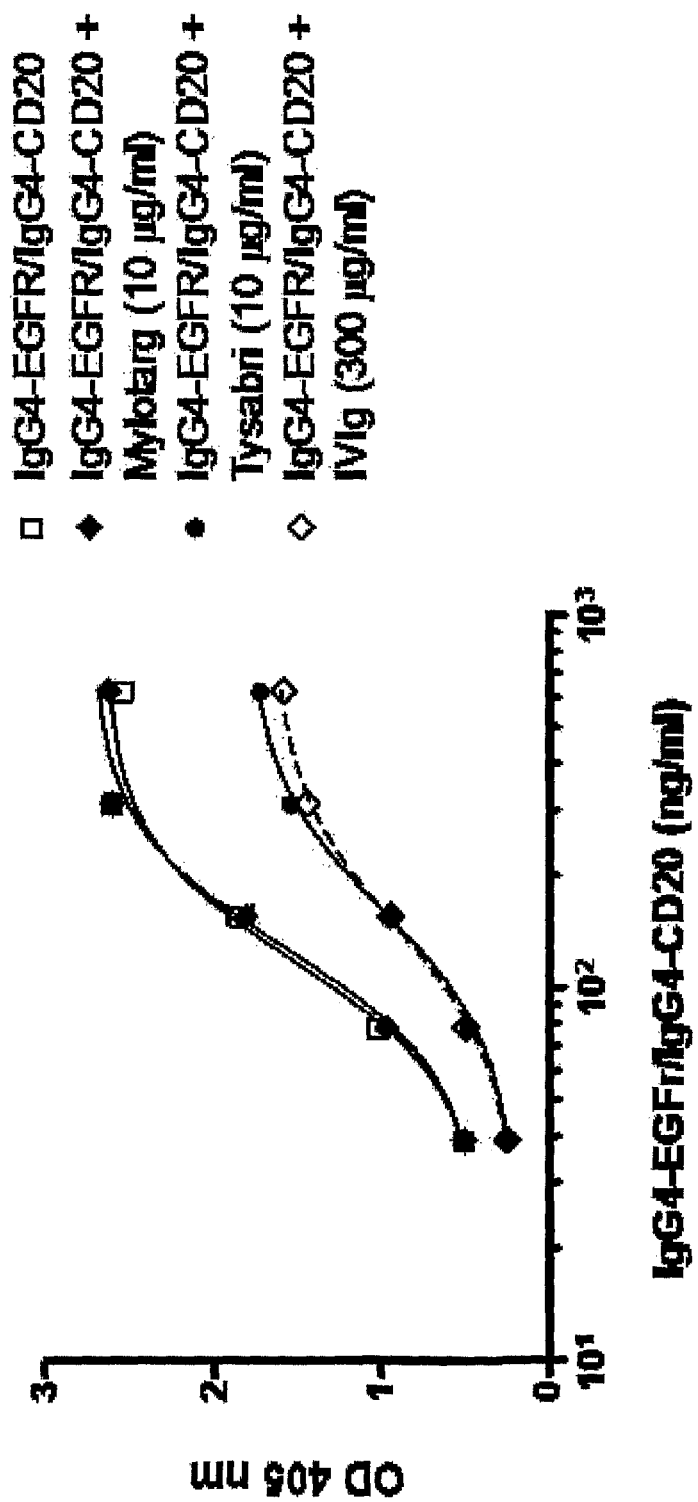

FIG. 20B shows that in the presence of an excess of Tysabri, but not Mylotarg, exchange of Fab arms of the recombinant CD20 and EGFr antibodies was inhibited.

This indicates that Tysabri, but not Mylotarg, participates in the Fab arm exchange reaction and that a stabilized, IgG1-like core-hinge does not participate in Fab-arm exchange under in vitro conditions where 0.5 mM GSH is used.

Example 37

Half Molecule Exchange of IgG1-CPSC Constructs with Additional Mutations at Position 292

Similar to Example 35, three IgG1 mutants were made in both pConG1f2F8 (specific for EGFR) and pConG1f7D8 (specific for CD20): an IgG1 with an IgG4 core-hinge (IgG1-CPSC) and two CH3 domain swap mutants (IgG1-CH3(IgG4) and IgG1-CPSC-CH3(IgG4) (i.e. constructs in which the CH3 region of IgG1 was replaced by the CH3 region of IgG4). This resulted in the following constructs pG1f-2F8CPSC, pG1f-7D8CPSC, pG1f-2F8-CH3(G4), pG1f-7D8-CH3(G4), pG1f-2F8CPSC-CH3(G4) and pG1f-7D8CPSC-CH3(G4)

Subsequently R238Q, K292R, K292Y, K292F, K292W, Q302E or P328L mutations (see SEQ ID NO: 19) were introduce in the CH3 domain of both the pG1f-2F8CPSC and pG1f-7D8CPSC constructs, basically as described above. In short, mutagenic primers, forward and reverse, were designed with Vector NTI Advance 10. Quickchange site-directed mutagenesis kit (Stratagene) was used to create the constructs.

Recombinant antibodies from these constructs were transiently expressed in HEK 293 cells in 3 ml, 6-wells plates (NUNC) or in 125 ml erlenmeyers (Corning) with 293 Fectin (Invitrogen) as transfection reagent. The culture supernatants were subsequently dialysed against PBS and concentration was measured by nephelometry (see above). The following mixtures of unpurified buffer exchanged antibodies were incubated with 0.5 GSH at 37° C. for 24 h and samples were drawn in PBS-AT, in which the (bi)specific IgG concentrations were measured as described in previous examples:

IgG1-2F8 wt with IgG1-7D8 wt (indicated as IgG1)
IgG1-2F8-CPSC with IgG1-7D8-CPSC (indicated as IgG1-CPSC)
IgG1-2F8-CH3(IgG4) with IgG1-7D8-CH3(IgG4) (indicated as IgG1-CH3(IgG4))
IgG1-2F8-CPSC-CH3(IgG4) with IgG1-7D8-CPSC-CH3(IgG4) (indicated as IgG1-CPSC-CH3(IgG4))
IgG1-2F8-CPSC-R238Q with IgG1-7D8-CPSC-R238Q (indicated as IgG1-CPSC-R238Q)
IgG1-2F8-CPSC-K292R with IgG1-7D8-CPSC-K292R (indicated as IgG1-CPSC-K292R)
IgG1-2F8-CPSC-K292Y with IgG1-7D8-CPSC-K292Y (indicated as IgG1-CPSC-K292Y)
IgG1-2F8-CPSC-K292F with IgG1-7D8-CPSC-K292F (indicated as IgG1-CPSC-K292F)
IgG1-2F8-CPSC-K292W with IgG1-7D8-CPSC-K292W (indicated as IgG1-CPSC-K292W)
IgG1-2F8-CPSC-Q302E with IgG1-7D8-CPSC-Q302E (indicated as IgG1-CPSC-Q302E)
IgG1-2F8-CPSC-P328L with IgG1-7D8-CPSC-P328L (indicated as IgG1-CPSC-P328L)
IgG4-2F8 wt with IgG4-7D8 wt (indicated as IgG4)

Figure 21:
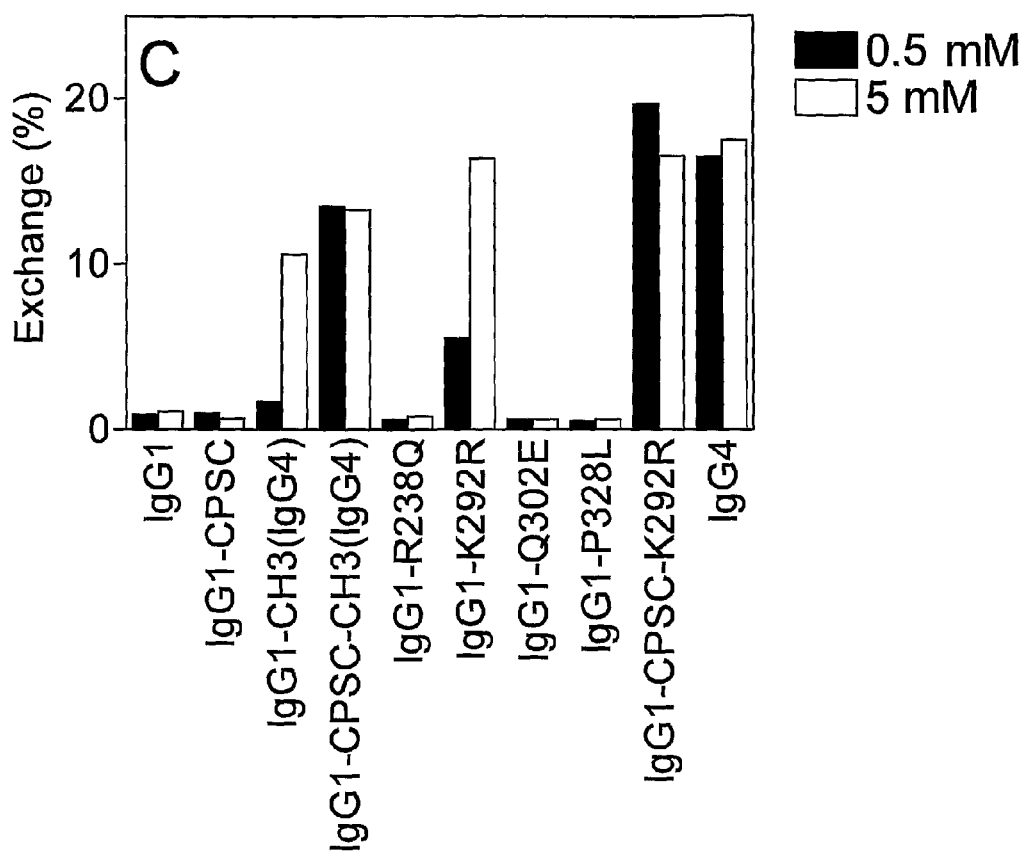

FIG. 21 shows that under the tested in vitro conditions (0.5 mM), half molecule exchange occurs when a CPSC hinge is present and an R at position 292. Additionally, the results show that a Y or F at position 292, but not a W, also facilitates half molecule exchange albeit to a lesser extent. An R or Q at position 238, an Q or E at position 302 and a P or L at position 328 do not influence the inability of and IgG1-CPSC to exchange half molecules.

Example 38

IgG4 Molecules with Stabilized CPPC Hinge can Fab-Arm Exchange In Vitro (with 5 mM GSH), but not In Vivo A mixture of IgG4-EGFR-CPPC and IgG4-CD20 was incubated for 24 h in the presence of 5 mM GSH and evaluated by mass spectrometry (ESI-TOF MS). Fifty µl samples containing 200 µg/ml of each antibody were deglycosylated overnight with 1 µl N-glycosidase F (Roche Diagnostics NL BV, Almere, The Netherlands). Samples were desalted on an Acquity UPLC™ (Waters, Milford, USA) with a BEH C8, 1.7 µm, 2.1×50 mm column at 60° C. Five µl was injected and eluted with a gradient from 5% to 95% eluent B. Eluent A was MilliQ water (Millipore Synthesis A10 apparatus) and eluent B was LC-MS grade acetonitrile (Biosolve, Valkenswaard, The Netherlands). Both eluents contained 0.05% formic acid as organic modifier (Fluka Riedel-de Haen, Buchs, Germany). Time-of-flight electrospray ionization mass spectra were recorded on-line on a micrOTOF™ mass spectrometer (Bruker, Bremen, Germany) operating in the positive ion mode. In each analysis, a 500-5000 m/z scale was internally calibrated with ES tuning mix (Agilent Technologies, Santa Clara, USA). Mass spectra were deconvoluted by using the Maximum Entropy algorithm, which is provided with DataAnalysis™ software v. 3.3 (Bruker).

Figure 22A:
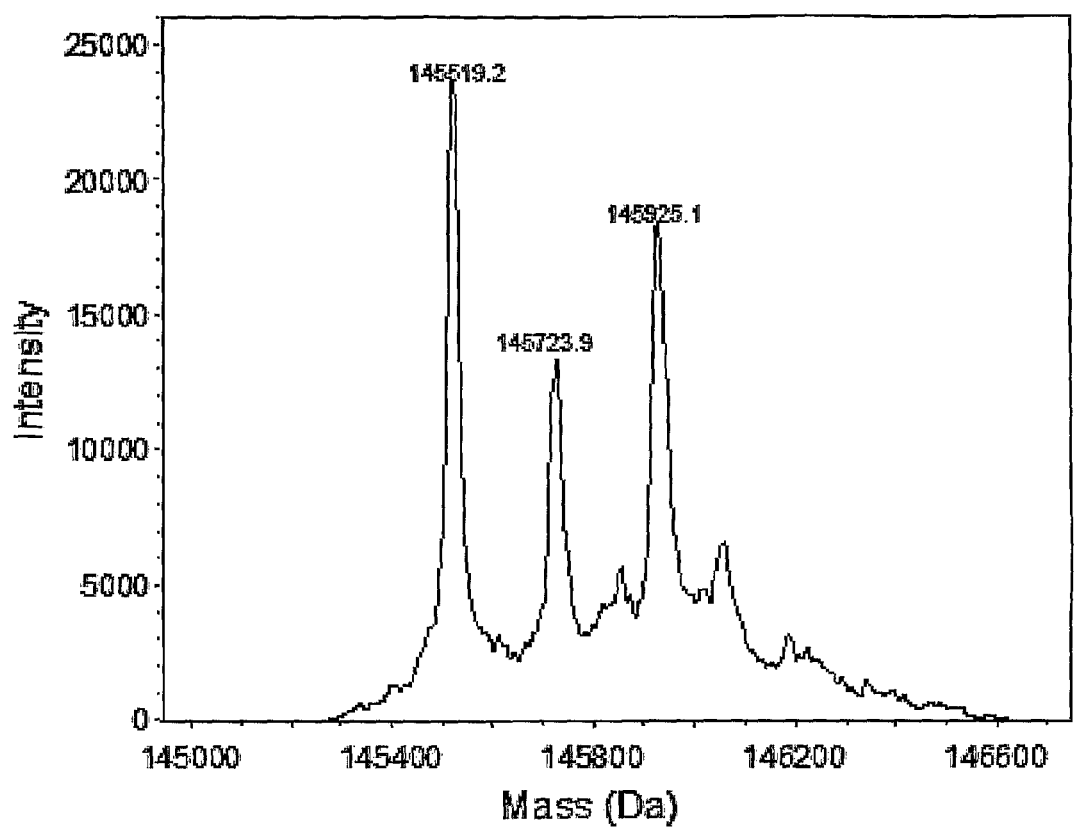

FIG. 22A shows that in the presence of 5 mM GSH a new peak with an intermediate mass corresponding to a Fab-arm exchanged molecule appeared (145.7 kDa). The novel mass corresponded to the expected mass of the bispecific anti-EGFR/CD20 antibody. No bispecific antibody peak appeared when no GSH or 0.5 mM GSH was used (data not shown). This indicates that a mutant containing an IgG1 like, CPPC hinge and a IgG4-like CH3 region can be made to exchange half-molecules in vitro at higher GSH concentrations (as also indicated in Example 35, 36, 37).

To study whether Fab-arm exchange of a stabilized hinge mutant containing an IgG1 like, CPPC hinge and a IgG4-like CH3 occurs in vivo, we injected equal mixtures of IgG4-CD20 with IgG1-EGFR, IgG4-EGFR, IgG4-EGFR-CPPC into immunodeficient mice. Blood samples were drawn at different time-points and bispecific antibodies were quantified in ELISA (as described above) using in vitro exchanged mixtures (IgG4-EGFR/IgG4-CD20) as reference standards.

Figure 22B:
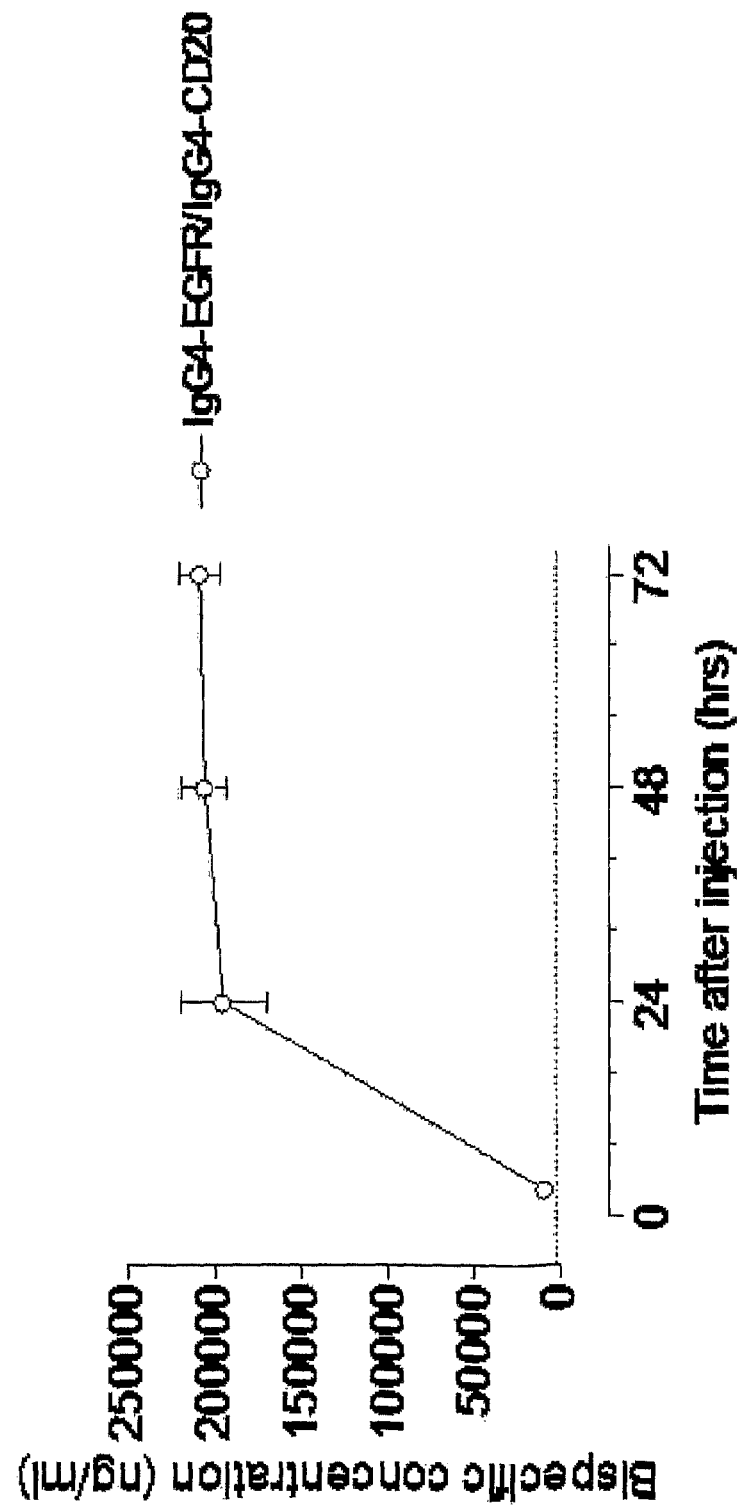

FIG. 22B shows that bispecific antibodies appeared in the blood of mice injected with mixtures containing wild-type IgG4 molecules (IgG4-EGFR). Bispecific antibodies were undetectable in mixtures containing hinge-stabilized IgG4 (IgG4-EGFR-CPPC) or IgG1 molecules (IgG1-EGFR) ((symbols not shown in figure)). This indicates that core-hinge stabilization prevents IgG4 Fab-arm exchange in vivo, but are not able to exchange half molecules in vivo (although we can not rule out that low-level exchange below the level of detection (<8% in 72 hrs) of hinge-stabilized IgG4 does occur).

This suggests that bispecific antibodies containing stabilized CPPC hinges can be obtained by Fab-arm exchange in vitro. After subsequent specific purification of these bispecific antibodies, these antibodies will remain stable (i.e will not Fab-arm exchange) upon injection in vivo.

Example 39

Fab Arm Exchange of CXXC-Mutants

The ability to exchange Fab arms of antibodies containing various CXXC-motifs in the core hinge was tested. The following CXXC-motifs were introduced into IgG4 bet v 1 and IgG4 feld 1, using site directed mutagenesis techniques as described above:

CGHC (SEQ ID NO: 33) (active site sequence described for protein-disulphide-isomerase, PDI)
CGC (peptide described to have disulfide reduction potential)
CPRC (SEQ ID NO: 32) (core-hinge sequence of Gorilla IgG4)
CPHC (SEQ ID NO: 34) (active site sequence described for human thioredoxin)

The following mixtures of purified antibodies were incubated with 0.5 mM GSH at 37° C. and samples were drawn in PBS-AT at different timepoints between 0 and 24 h, in which the (bi)specific IgG concentrations were measured as described in previous examples:

IgG1 a-feld1 wt with IgG1 a-betv1 wt (indicated as IgG1 in FIGS. 23 and 24)
IgG4 a-feld1 wt with IgG4 a-betv1 wt (indicated as IgG4 in FIGS. 23 and 24)
IgG4 a-feld1 CGHC with IgG4 a-betv1 CGHC (indicated as CGHC in FIGS. 23 and 24)

IgG4 a-feld1 CGC with IgG4 a-betv1 CGC (indicated as CGC in FIGS. 23 and 24)

IgG4 a-feld1 CPRC with IgG4 a-betv1 CPRC (indicated as CPRC in FIGS. 23 and 24)

IgG4 a-feld1 CPHC with IgG4 a-betv1 CPHC (indicated as CPHC in FIGS. 23 and 24)

The results (FIG. 23) showed that over time, no Fab arm exchange occurred of antibodies containing a CGC motif or a IgG1 core hinge. Fab arm exchange of antibodies containing a CGHC (SEQ ID NO: 33) motif was as effective as of IgG4 wt antibodies. Fab arm exchange also occurred of antibodies containing a CPRC (SEQ ID NO: 32) motif, albeit somewhat slower, and to a lesser extent also of antibodies containing a CPHC (SEQ ID NO: 34) motif.

Also, the effect of GSH concentration (1 to 20,000 μM) on the ability of these mixtures to undergo Fab arm exchange after 24 h incubation at 37° C. was tested. Fab arm exchange of CPHC-(SEQ ID NO: 34), CPRC-(SEQ ID NO: 32) and CGHC-(SEQ ID NO: 33) motif containing antibodies as well as IgG4 wt antibodies was found to be dependent on GSH concentration (FIG. 24), with an optimum between 100 and 1,000 μM GSH.

The invention claimed is:

1. An ex vivo method for the generation of a bispecific antibody, said method comprising the steps of: a) providing a first antibody having a first binding specificity and a second antibody having a second binding specificity which differs from said first binding specificity, wherein the first and/or second antibody comprises the CH3 region of SEQ ID NO: 19, but with a substitution selected from the group consisting of: Arg (R) in position 238 is replaced by Gln (Q); Lys (K) in position 292 is replaced by Arg (R); Gln (Q) in position 302 is replaced by Glu (E); and Pro (P) in position 328 is replaced by Leu (L), b) incubating said first and second antibodies together under reducing conditions which allow the cysteines in the core hinge region to undergo disulfide-bond isomerization, and c) obtaining a bispecific antibody.

2. The ex vivo method of claim 1, wherein the first and/or second antibody comprises an IgG1 hinge region.

3. The ex vivo method of claim 1, wherein the first and/or second antibody comprises a $CX_1X_2C$ sequence in the core hinge region, wherein X1 and X2 can be any amino acid, provided that $X_1$ and $X_2$ are not both proline.

4. The ex vivo method of claim 3, wherein the first and/or second antibody comprises a $CX_3PC$ or $CPX_3C$ sequence in the core hinge region, wherein $X_3$ can be any amino acid except for proline.

5. The ex vivo method of claim 3, wherein the first and/or second antibody comprises a CSPC (SEQ ID NO: 30), CPSC (SEQ ID NO: 27), CRPC (SEQ ID NO: 31), CPRC (SEQ ID NO: 32), CGHC (SEQ ID NO: 33) or CPHC (SEQ ID NO: 34) sequence in the core hinge region.

6. The ex vivo method of claim 1, wherein said CH3 region has Lys (K) in position 292 replaced by Arg (R).

7. An ex vivo method for the generation of a bispecific antibody, said method comprising the steps of: a) providing a first antibody having a first binding specificity and a second antibody having a second binding specificity which differs from said first binding specificity, wherein the first and/or second antibody comprises the CH3 region of SEQ ID NO: 19, except that Lys (K) in position 292 has been replaced by Arg (R), b) incubating said first and second antibodies together under reducing conditions which allow the cysteines in the core hinge region to undergo disulfide-bond isomerization, and c) obtaining a bispecific antibody.

8. The ex vivo method of claim 1 or 7, wherein said first antibody and/or said second antibody is a human antibody.

9. The ex vivo method of claim 1 or 7, wherein the conditions in step c) are chosen such that no significant reduction or isomerization of disulfide bridges outside the core hinge region occurs.

10. The ex vivo method of claim 1 or 7, wherein step c) comprises the addition of a reducing agent.

11. The ex vivo method of claim 1 or 7, wherein step c) comprises the addition of an agent selected from the group consisting of: glutathione, L-cysteine, dithiothreitol, beta-mercapto-ethanol, and cysteamine.

12. The ex vivo method of claim 10, wherein the concentration of said agent is such that the redox potential of the solution generated in step c) is equal to, or more reducing than, the redox potential generated by 1 microM of glutathione, under the conditions of: PBS (pH 7.4) supplemented with 0.05% (w/v) NaN3, containing 10 microgram/ml of each of the two antibodies at 37° C.

13. The ex vivo method of claim 10, wherein the concentration of said agent is such that the redox potential of the solution generated in step c) is equal to, or more reducing than, the redox potential generated by 1 mM of glutathione, under the conditions of: expression medium containing mixtures of unpurified antibodies at 37° C.

14. The ex vivo method of claim 12, wherein the concentration of said agent is such that the redox potential of the solution generated in step c) is equal to, or less reducing than, the redox potential generated by 1 M of glutathione.

15. The ex vivo method of claim 1 or 7, wherein fewer than 10% of the antibody molecules in the resulting composition are in an aggregated state.

16. The ex vivo method of claim 1 or 7, comprising the further step of bringing the composition obtained in step c) to non-reducing conditions, in order to stop further half-molecule exchange.

17. The ex vivo method of claim 1 or 7, comprising the further step of stabilizing the bispecific antibody by a method selected from: a) chemically cross-linking the cysteines in the hinge region, b) chemically cross-linking the carbohydrate side-chains on the half-molecules, and c) cross-linking the asymmetrically introduced cysteines in the CH3 region.

18. The ex vivo method of claim 1 or 7, comprising the further step of purifying the bispecific antibody.

19. The ex vivo method of claim 1 or 7, comprising the further step of formulating the resulting bispecific antibodies into a pharmaceutical composition for therapeutic use.

20. The ex vivo method of claim 1 or 7, wherein the first antibody has binding specificity for a tumor cell or tumor cell protein.

21. The ex vivo method of claim 20, wherein the second antibody has binding specificity for a tumor cell or tumor cell protein.

22. The ex vivo method of claim 1 or 7, wherein the first and/or second antibody is linked to a compound selected from the group consisting of: a cytotoxic agent; a radioisotope; a prodrug or drug; a cytokine; a chemokine and complement.

23. The ex vivo method of claim 1, wherein said CH3 region has Arg (R) in position 238 replaced by Gln (Q).

24. The ex vivo method of claim 1, wherein said CH3 region has Gln (Q) in position 302 replaced by Glu (E).

25. The ex vivo method of claim 1, wherein said CH3 region has Pro (P) in position 328 replaced by Leu (L).

26. The ex vivo method of claim 1, wherein said CH3 region has Glu (E) at position 239.

27. The ex vivo method of claim 1, wherein the CH3 region has two substitutions selected from the group consisting of: Arg (R) in position 238 is replaced by Gln (Q); Lys (K) in position 292 is replaced by Arg (R); Gln (Q) in position 302 is replaced by Glu (E); and Pro (P) in position 328 is replaced by Leu (L).

28. The ex vivo method of claim 1, wherein the CH3 region has three substitutions selected from the group consisting of: Arg (R) in position 238 is replaced by Gln (Q); Lys (K) in position 292 is replaced by Arg (R); Gln (Q) in position 302 is replaced by Glu (E); and Pro (P) in position 328 is replaced by Leu (L).

29. The ex vivo method of claim 1, wherein the CH3 region has the following substitutions: Arg (R) in position 238 is replaced by Gln (Q); Lys (K) in position 292 is replaced by Arg (R); Gln (Q) in position 302 is replaced by Glu (E); and Pro (P) in position 328 is replaced by Leu (L).

* * * * *

SEQUENCE LISTING

```
<160> NUMBER OF SEQ ID NOS: 34

<210> SEQ ID NO 1
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
agccaccgta cgtttgattt ccagcttggt gcctcc                              36

<210> SEQ ID NO 2
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gatgcaagct tgccgccacc atggagtcac agattcaggc attt                    44

<210> SEQ ID NO 3
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
cgatgggccc ttggtgctgg ctgaggagac ggtgactgag gt                      42

<210> SEQ ID NO 4
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gatgcaagct tgccgccacc atgaaatgca gctgggttat cttc                    44

<210> SEQ ID NO 5
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
```
agccaccgta cgttttattt ccaactttgt ccccga                                    36

<210> SEQ ID NO 6
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gatgcaagct tgccgccacc atggaatcac agactcaggt cctc                           44

<210> SEQ ID NO 7
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
cgatgggccc ttggtgctgg ctgcagagaa agtgaccaga gt                             42

<210> SEQ ID NO 8
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gatgcaagct tgccgccacc atgggatgga gctatatcat cctc                           44

<210> SEQ ID NO 9
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tgagaattcg gtgggtgctt tatttccatg ct                                        32

<210> SEQ ID NO 10
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gtagaagctt accatcgcgg atagacaaga acc                                       33

<210> SEQ ID NO 11
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tgttaactgc tcactggatg gtggga                                          26

<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tccctgggca caattttctt gtccacc                                         27

<210> SEQ ID NO 13
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
tgaaagcttc taatacgact cactataggg c                                    31

<210> SEQ ID NO 14
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
tgaaagcttc taatacgact cactataggg caagcagtgg tatcaacgca gagt           54

<210> SEQ ID NO 15
<211> LENGTH: 137
<212> TYPE: PRT
<213> ORGANISM: Artificial Sequence
<220> FEATURE:
<223> OTHER INFORMATION: Description of Artificial Sequence: Synthetic
      antibody variable region polypeptide

<400> SEQUENCE: 15

Met Lys Cys Ser Trp Val Ile Phe Phe Leu Met Ala Val Val Thr Gly
1               5                   10                  15

Val Asn Ser Glu Val Gln Leu Gln Gln Ser Gly Ala Glu Leu Val Lys
            20                  25                  30

Pro Gly Ala Ser Val Lys Leu Ser Cys Thr Ala Ser Gly Phe Asn Ile
        35                  40                  45

Lys Asp Thr Tyr Ile His Trp Val Lys Gln Arg Pro Glu Gln Gly Leu
    50                  55                  60

Glu Trp Val Gly Arg Ile Asp Pro Ala Thr Gly Asn Thr Arg Tyr Asp
65                  70                  75                  80

Pro Lys Phe Gln Gly Lys Ala Thr Ile Thr Ala Asp Thr Ser Ser Asn
                85                  90                  95

Thr Ala Tyr Leu Gln Leu Ser Ser Leu Thr Ser Glu Asp Thr Ala Val
            100                 105                 110

Tyr Tyr Cys Ala Ser Phe Arg Pro Gly Tyr Ala Leu Asp Tyr Trp Gly
        115                 120                 125

Gln Gly Thr Ser Val Thr Val Ser Ser
    130                 135

<210> SEQ ID NO 16
<211> LENGTH: 127
<212> TYPE: PRT
<213> ORGANISM: Artificial Sequence
<220> FEATURE:
<223> OTHER INFORMATION: Description of Artificial Sequence: Synthetic
      antibody variable region polypeptide

<400> SEQUENCE: 16

Met Glu Ser Gln Ile Gln Ala Phe Val Phe Val Phe Leu Trp Leu Ser
1               5                   10                  15

Gly Val Asp Gly Asp Ile Val Met Thr Gln Ser His Lys Phe Met Ser
            20                  25                  30

Thr Ser Val Gly Asp Arg Val Ser Phe Thr Cys Lys Ala Ser Gln Asp
        35                  40                  45

Val Phe Thr Ala Val Ala Trp Tyr Gln Gln Lys Pro Gly Gln Ser Pro
    50                  55                  60

Lys Leu Leu Ile Tyr Trp Ala Ser Thr Arg Arg Thr Gly Val Pro Asp
65                  70                  75                  80

Arg Phe Thr Gly Ser Gly Ser Gly Thr Asp Tyr Thr Leu Thr Ile Ser
                85                  90                  95

Ser Val Gln Ala Glu Asp Leu Ala Leu Tyr Tyr Cys Gln Gln His Phe
            100                 105                 110

Ser Thr Pro Pro Thr Phe Gly Gly Gly Thr Lys Leu Glu Ile Lys
        115                 120                 125

<210> SEQ ID NO 17
<211> LENGTH: 138
<212> TYPE: PRT
<213> ORGANISM: Artificial Sequence
<220> FEATURE:
<223> OTHER INFORMATION: Description of Artificial Sequence: Synthetic
      antibody variable region polypeptide

<400> SEQUENCE: 17

Met Gly Trp Ser Tyr Ile Ile Leu Phe Leu Val Ala Thr Ala Thr Asp
1               5                   10                  15

Val His Ser Gln Val Gln Leu Gln Gln Pro Gly Ala Glu Leu Val Lys
            20                  25                  30

Pro Gly Ala Ser Val Lys Leu Ser Cys Lys Ala Ser Gly Tyr Ser Phe
        35                  40                  45

Thr Ser Tyr Trp Met His Trp Leu Lys Gln Arg Pro Gly Gln Gly Leu
    50                  55                  60

Glu Trp Ile Gly Glu Ile Asn Pro Asn Asn Gly Arg Thr Tyr Tyr Asn
65                  70                  75                  80

Glu Lys Phe Lys Thr Lys Ala Thr Leu Thr Val Asp Lys Ser Ser Ser
                85                  90                  95

Thr Ala Tyr Met Gln Leu Asn Ser Leu Thr Ser Glu Asp Ser Ala Val
            100                 105                 110

Tyr Tyr Cys Ala Arg Arg Leu Thr Met Val Glu Ser Phe Ala Tyr Trp
        115                 120                 125

Gly Gln Gly Thr Leu Val Thr Phe Ser Ala
    130                 135

<210> SEQ ID NO 18
<211> LENGTH: 133
<212> TYPE: PRT
<213> ORGANISM: Artificial Sequence
<220> FEATURE:

<223> OTHER INFORMATION: Description of Artificial Sequence: Synthetic
      antibody variable region polypeptide

<400> SEQUENCE: 18

Met Glu Ser Gln Thr Gln Val Leu Met Ser Leu Leu Phe Trp Val Ser
1               5                   10                  15

Gly Thr Cys Gly Asp Ile Val Met Thr Gln Ser Pro Ser Ser Leu Thr
                20                  25                  30

Val Thr Ala Gly Glu Lys Val Thr Met Ser Cys Lys Ser Ser Gln Ser
            35                  40                  45

Leu Leu Asn Ser Gly Asn Gln Lys Asn Tyr Leu Thr Trp Tyr Gln Gln
        50                  55                  60

Lys Pro Gly Gln Pro Pro Lys Leu Leu Ile Tyr Trp Ala Ser Thr Arg
65                  70                  75                  80

Glu Ser Gly Val Pro Asp Arg Phe Thr Gly Ser Gly Ser Gly Thr Asp
                85                  90                  95

Phe Ser Leu Thr Ile Ser Ser Val Gln Ala Glu Asp Leu Ala Ile Tyr
            100                 105                 110

Tyr Cys Gln Asn Asp Tyr Ser Tyr Pro Phe Thr Phe Gly Ser Gly Thr
        115                 120                 125

Lys Leu Glu Ile Lys
    130

<210> SEQ ID NO 19
<211> LENGTH: 330
<212> TYPE: PRT
<213> ORGANISM: Homo sapiens
<220> FEATURE:
<221> NAME/KEY: MOD_RES
<222> LOCATION: (239)..(239)
<223> OTHER INFORMATION: Asp or Glu
<220> FEATURE:
<221> NAME/KEY: MOD_RES
<222> LOCATION: (241)..(241)
<223> OTHER INFORMATION: Leu or Met

<400> SEQUENCE: 19

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu

```
                      165                 170                 175
Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Xaa Glu
225                 230                 235                 240

Xaa Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 20
<211> LENGTH: 326
<212> TYPE: PRT
<213> ORGANISM: Homo sapiens

<400> SEQUENCE: 20

Ala Ser Thr Lys Gly Pro Ser Val Phe Pro Leu Ala Pro Cys Ser Arg
1               5                  10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205
```

```
Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 21
<211> LENGTH: 377
<212> TYPE: PRT
<213> ORGANISM: Homo sapiens

<400> SEQUENCE: 21

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
                100                 105                 110

Arg Cys Pro Glu Pro Lys Ser Cys Asp Thr Pro Pro Pro Cys Pro Arg
            115                 120                 125

Cys Pro Glu Pro Lys Ser Cys Asp Thr Pro Pro Pro Cys Pro Arg Cys
        130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255
```

```
Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
        355                 360                 365

Lys Ser Leu Ser Leu Ser Pro Gly Lys
    370                 375

<210> SEQ ID NO 22
<211> LENGTH: 327
<212> TYPE: PRT
<213> ORGANISM: Homo sapiens

<400> SEQUENCE: 22

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
```

```
                    245                 250                 255
Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
            325

<210> SEQ ID NO 23
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
cttgtgacaa aactcacacc tgcccatcgt gcccaggtaa gccag              45

<210> SEQ ID NO 24
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ctggcttacc tgggcacgat gggcaggtgt gagttttgtc acaag              45

<210> SEQ ID NO 25
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
cccccatgcc caccatgccc aggtaagcca acccaggcct cgc                43

<210> SEQ ID NO 26
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
gcgaggcctg ggttggctta cctgggcatg gtgggcatgg ggg                43

<210> SEQ ID NO 27
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27
```

Cys Pro Ser Cys
1

<210> SEQ ID NO 28
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Cys Pro Pro Cys
1

<210> SEQ ID NO 29
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Cys Pro Ser Cys
1

<210> SEQ ID NO 30
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Cys Ser Pro Cys
1

<210> SEQ ID NO 31
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Cys Arg Pro Cys
1

<210> SEQ ID NO 32
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Cys Pro Arg Cys
1

<210> SEQ ID NO 33
<211> LENGTH: 4
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 33

Cys Gly His Cys
1

<210> SEQ ID NO 34
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Cys Pro His Cys
1
```